United States Patent
Park et al.

(10) Patent No.: US 10,374,174 B2
(45) Date of Patent: Aug. 6, 2019

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Bumwoo Park, Seoul (KR); Yoonhyun Kwak, Seoul (KR); Hyun Koo, Seoul (KR); Jiwhan Kim, Seoul (KR); Sunyoung Lee, Seoul (KR); Jiyoun Lee, Incheon (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 619 days.

(21) Appl. No.: 14/931,270

(22) Filed: Nov. 3, 2015

(65) Prior Publication Data

US 2016/0204362 A1  Jul. 14, 2016

(30) Foreign Application Priority Data

Jan. 9, 2015  (KR) .................. 10-2015-0003471

(51) Int. Cl.
*C07F 15/00* (2006.01)
*C09K 11/06* (2006.01)
(Continued)

(52) U.S. Cl.
CPC ........ *H01L 51/0087* (2013.01); *C07F 15/004* (2013.01); *C07F 15/0026* (2013.01);
(Continued)

(58) Field of Classification Search
CPC ......... H01L 51/0084–51/0088; C07F 15/0026; C07F 15/004; C07F 15/0093; C09K 11/06

See application file for complete search history.

(56) References Cited

U.S. PATENT DOCUMENTS 6,830,828 B2   12/2004   Thompson et al.
7,329,898 B2   2/2008   Igarashi
(Continued)

FOREIGN PATENT DOCUMENTS

JP   2005314663 A   11/2005
JP   2009267245 A * 11/2009

OTHER PUBLICATIONS

Yang, et al. "Highly efficient phosphorescent materials based on platinum complexes and their application in organic light-emitting devices (OLEDs)." Platinum Metals Review 57.1 (2013): 2-16.*
(Continued)

*Primary Examiner* — Susan D Leong
*Assistant Examiner* — William E McClain
(74) *Attorney, Agent, or Firm* — Cantor Colburn LLP

(57) ABSTRACT

An organometallic compound represented by Formula 1:

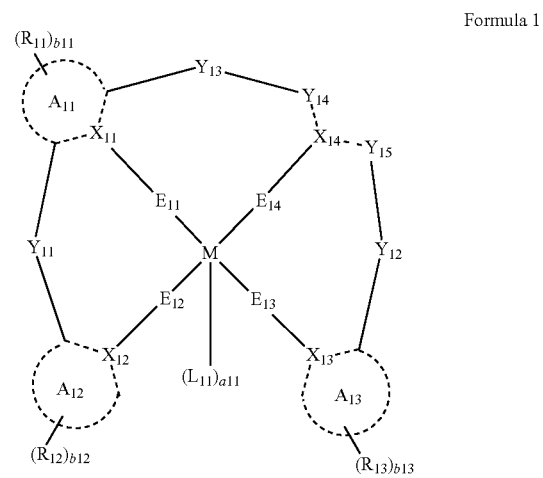

Formula 1 wherein in Formula 1, groups and variables are the same as described in the specification.

20 Claims, 1 Drawing Sheet

(51) Int. Cl.
*H01L 51/00* (2006.01)
*H01L 51/50* (2006.01)

(52) U.S. Cl.
CPC .......... *C07F 15/0093* (2013.01); *C09K 11/06* (2013.01); *H01L 51/0085* (2013.01); *H01L 51/0088* (2013.01); *C09K 2211/185* (2013.01); *H01L 51/5016* (2013.01)

(56) References Cited

U.S. PATENT DOCUMENTS

| | | | |
|---|---|---|---|
| 7,442,797 B2 | 10/2008 | Itoh et al. | |
| 7,579,093 B2 | 8/2009 | Sano et al. | |
| 2002/0134984 A1* | 9/2002 | Igarashi | C09K 11/06 257/79 |
| 2006/0051614 A1* | 3/2006 | Su | C07F 15/0033 428/690 |
| 2006/0073359 A1* | 4/2006 | Ise | C07F 15/0086 428/690 |
| 2006/0105202 A1* | 5/2006 | Kitamura | C09K 11/06 428/690 |
| 2006/0134461 A1* | 6/2006 | Huo | C07F 15/0086 428/690 |
| 2007/0075311 A1* | 4/2007 | Okada | C07F 1/08 257/40 |
| 2007/0148495 A1* | 6/2007 | Che | C09K 11/06 428/690 |
| 2008/0001530 A1* | 1/2008 | Ise | C09K 11/06 313/504 |
| 2010/0171111 A1* | 7/2010 | Takada | C07F 15/0086 257/40 |
| 2011/0315933 A1* | 12/2011 | Stoessel | C07D 471/16 252/500 |
| 2012/0169220 A1 | 7/2012 | Nii et al. | |

OTHER PUBLICATIONS

Machine Translation of JP-2009267245-A.*
Vezzu, et al., "Highly luminescent tetradentate bis-cyclometalated platinum complexes: design, synthesis, structure, photophysics, and electroluminescence application." Inorganic chemistry 49.11 (2010): 5107-5119.*
Fukagawa, et al. "Highly efficient and stable red phosphorescent organic light-emitting diodes using platinum complexes." Advanced Materials 24.37 (2012): 5099-5103.*
Sahni, et al. "Building blocks for polymetallic ruthenium (II) and osmium (II) polypyridine luminophores." Journal of the Chemical Society, Chemical Communications 2 (1993): 123-125.*
Daniela Pucci et al. "Unsuspected mesomorphism in "tail-free" cyclopalladated 3,5-disubstituted-2-(2'-pyridyl) pyrroles", Chem. Commun. 2009, 1550-1552.
Takuya Yamagata et al. "Optical properties of highly planar diketopyrrolopyrrole derivatives fixed by coordinate bonds", Tetrahedron 70 (2014) 1451-1457.
Randolph P. Thummel et al. "Polyaza-Cavity Shaped Molecules. 14. Annelated 2-(2'-Pyridyl)indoles, 2,2'-Biindoles, and Related Systems", J. Org. Chem., 1989, 54(7), 1720-1725 (6 pp).

* cited by examiner

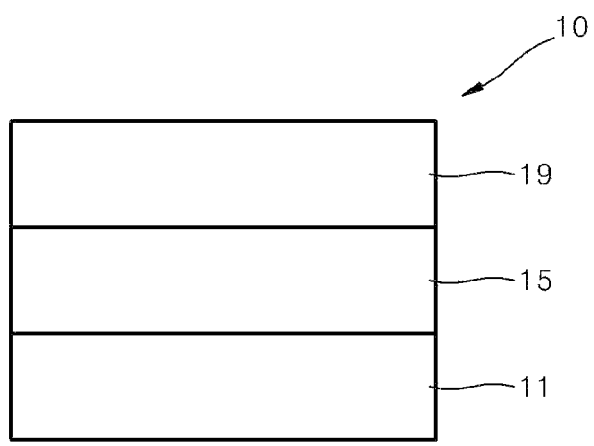

ORGANOMETALLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0003471, filed on Jan. 9, 2015, in the Korean Intellectual Property Office, the disclosure of which is incorporated herein in its entirety by reference.

BACKGROUND

1. Field

The present disclosure relates to an organometallic compound and an organic light-emitting device including the organometallic compound.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and also includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state to thereby generate light.

Various types of organic light emitting devices are known. However, there still remains a need in OLEDs having low driving voltage, high efficiency, high brightness, and long lifespan.

SUMMARY

Provided are an organometallic compound and an organic light-emitting device including the organometallic compound.

Additional aspects will be set forth in part in the description which follows and, in part, will be apparent from the description, or may be learned by practice of the presented exemplary embodiments.

According to an aspect of an exemplary embodiment, provided is an organometallic compound represented by Formula 1:

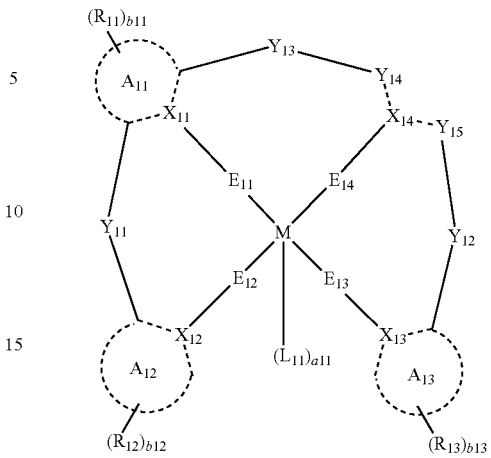

Formula 1

In Formula 1,

M may be selected from a Period 1 transition metal, a Period 2 transition metal, and a Period 3 transition metal;

$A_{11}$ to $A_{13}$ may be each independently selected from a $C_6$-$C_{20}$ cyclic group and a $C_1$-$C_{20}$ heterocyclic group; wherein $A_{11}$ and $A_{12}$ may be optionally linked to each other through a first linking group;

$X_{11}$ to $X_{13}$ may be each independently selected from C and N;

$X_{14}$ may be selected from N and a phosphorus atom (P);

$E_{11}$ to $E_{14}$ and $Y_{11}$ to $Y_{15}$ may be each independently selected from a single bond and a divalent linking group;

$X_{14}$ and $Y_{14}$ may be linked by a single bond or a double bond, $X_{14}$ and $Y_{15}$ may be linked by a single bond or a double bond;

$L_{11}$ may be selected from a monodentate ligand and a bidentate ligand;

a11 may be selected from 0, 1, and 2; and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), and —N($Q_1$)($Q_2$);

$Q_1$ to $Q_3$ may be each independently selected from a $C_1$-$C_{60}$ alkyl group and a $C_6$-$C_{60}$ aryl group;

b11 to b13 may be each independently selected from 1, 2, 3, 4, 5, 6, 7, 8, 9, and 10; and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to another aspect of an exemplary embodiment, provided is an organic light-emitting device including:
a first electrode;
a second electrode; and
an organic layer disposed between the first electrode and the second electrode, wherein the organic layer includes an emission layer and at least one organometallic compound represented by Formula 1.

The emission layer may include the organometallic compound, and the organometallic compound included in the emission layer may serve as a dopant, wherein the emission layer may further include a host.

BRIEF DESCRIPTION OF THE DRAWINGS

These and/or other aspects will become apparent and more readily appreciated from the following description of the exemplary embodiments, taken in conjunction with the accompanying drawings in which:

FIG. 1 illustrates a cross-sectional view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The organometallic compound is represented by Formula 1:

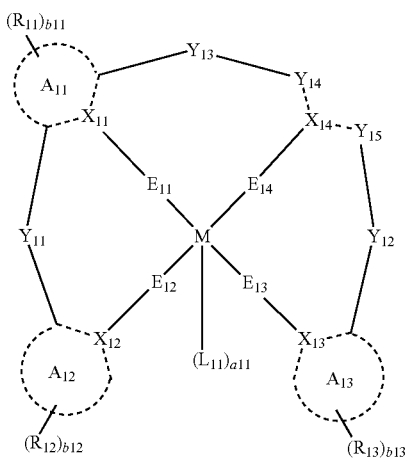

Formula 1

In Formula 1, M may be selected from a Period 1 transition metal, a Period 2 transition metal, and a Period 3 transition metal.

For example, M in Formula 1 may be selected from a Period 3 transition metal, but embodiments are not limited thereto.

In some embodiments, M in Formula 1 may be selected from osmium (Os), iridium (Ir), and platinum (Pt), but embodiments are not limited thereto.

$A_{11}$ to $A_{13}$ in Formula 1 may be each independently selected from a $C_6$-$C_{20}$ cyclic group and a $C_1$-$C_{20}$ heterocyclic group, and $A_{11}$ and $A_{12}$ may be optionally bonded to each other through a first linking group.

For example, $A_{11}$ to $A_{13}$ in Formula may be each independently selected from a benzene, a naphthalene, a fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, a benzoimidazole, a benzoxazole, an isobenzoxazole, an indazole, and a tetrahydroindazole; and a benzene, a naphthalene, a fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, a benzoimidazole, a benzoxazole, an isobenzoxazole, an indazole, and a tetrahydroindazole, each condensed with at least one selected from a $C_4$-$C_{10}$ alicyclic group and $C_1$-$C_{10}$ heteroalicyclic group, but embodiments are not limited thereto.

In some embodiments, $A_{11}$ to $A_{13}$ in Formula 1 may be each independently selected from a benzene, a naphthalene, a pyrrole, an imidazole, a pyrazole, a triazole, a pyridine, a pyrimidine, a pyrazine, a pyridazine, a triazine, a quinoline, an isoquinoline, an indole, a benzoimidazole, an indazole, and a tetrahydroindazole; and a benzene, a naphthalene, a pyrrole, an imidazole, a pyrazole, a triazole, a pyridine, a pyrimidine, a pyrazine, a pyridazine, a triazine, a quinoline, an isoquinoline, an indole, a benzoimidazole, an indazole, and a tetrahydroindazole, each condensed with at least one of $C_4$-$C_{10}$ alicyclic groups, but embodiments are not limited thereto.

In some embodiments, $A_{11}$ in Formula 1 may be selected from groups represented by Formulae 2-1 to 2-8, but embodiments are not limited thereto:

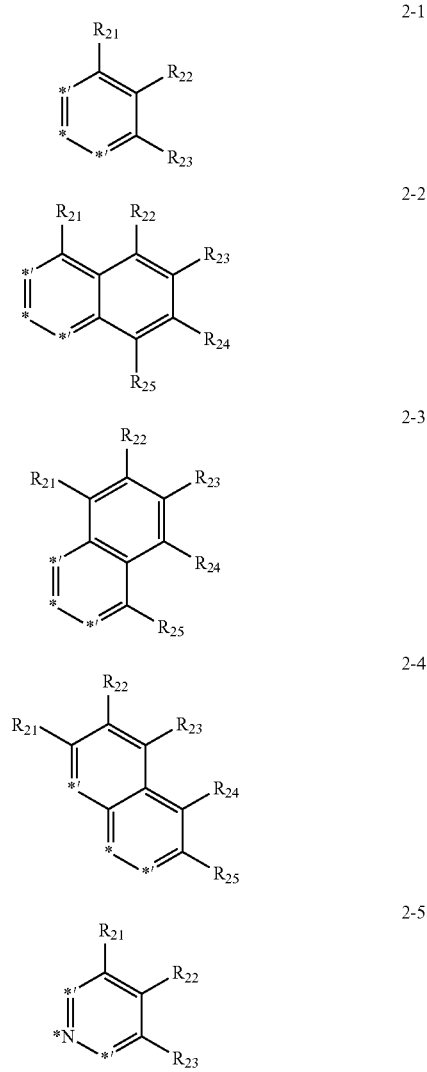

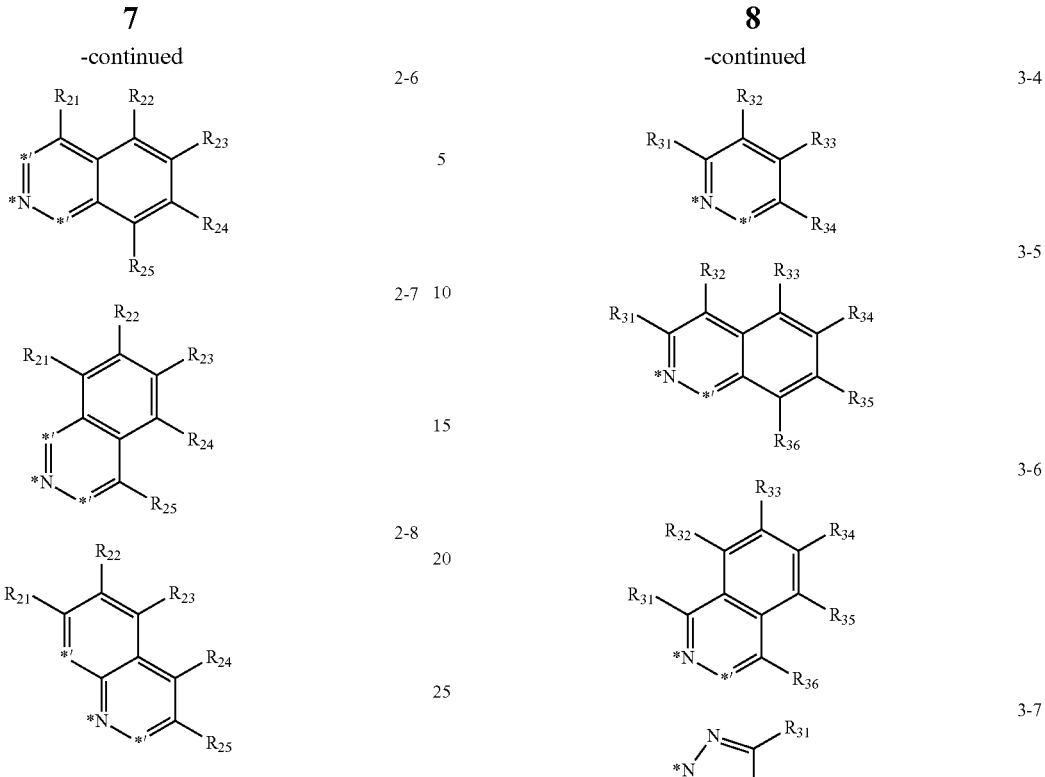

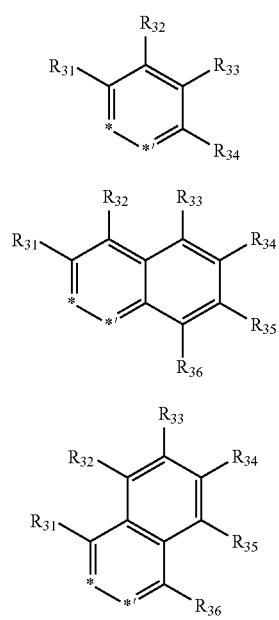

In Formulae 2-1 to 2-8,

* is a binding site to M or $E_{11}$ in Formula 1;

*' is a binding site to $Y_{11}$ or $Y_{13}$; and $R_{21}$ to $R_{25}$ are each independently the same as defined in connection with $R_{11}$ in Formula 1, which will be described later.

In some embodiments, $A_{12}$ and $A_{13}$ in Formula 1 may be each independently selected from groups represented by Formulae 3-1 to 3-9, but embodiments are not limited thereto:

In Formulae 3-1 to 3-9,

* is a binding site to M, $E_{12}$, or $E_{13}$ in Formula 1;

*' is a binding site to $Y_{11}$ or $Y_{12}$; and $R_{31}$ to $R_{40}$ are each independently the same as defined in connection with $R_{12}$ and $R_{13}$ in Formula 1 that will be described later.

For example, the first linking group may be selected from a single bond, *—O—*', *—S—*', *—N($Z_{11}$)—*', and *—[C($Z_{11}$)($Z_{12}$)]$_{m11}$—*';

$Z_{11}$ and $Z_{12}$ may be each independently selected from a hydrogen, a deuterium, —F, —Cl, —Br, —I, a substituted or unsubstituted $C_1$-$C_{60}$ alkyl group, and a substituted or unsubstituted $C_6$-$C_{60}$ aryl group;

m11 may be selected from 1, 2, 3, and 4; and each of * and *' may be a binding site to a neighboring atom.

In some embodiments, the first linking group may be selected from a single bond,

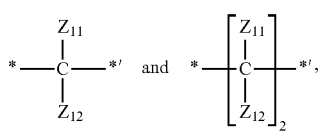

but embodiments are not limited thereto.

For example, $Z_{11}$ and $Z_{12}$ may be each independently selected from a hydrogen, a deuterium, —F, a methyl group, an ethyl group, a phenyl group, and a naphthyl group, but embodiments are not limited thereto.

In some embodiments, $Z_{11}$ and $Z_{12}$ may be each independently selected from a hydrogen, a deuterium, —F, a methyl group, and an ethyl group, but embodiments are not limited thereto.

In some embodiments, $Z_{11}$ and $Z_{12}$ may be a hydrogen, but embodiments are not limited thereto.

For example, m11 may be selected from 1 and 2, but embodiments are not limited thereto.

$X_{11}$ to $X_{13}$ in Formula 1 may be each independently selected from a carbon atom (C) and a nitrogen atom (N).

For example, $X_{11}$ to $X_{13}$ in Formula 1 may be N, but embodiments are not limited thereto.

In some embodiments, in Formula 1, $X_{11}$ and $X_{13}$ may be N while $X_{12}$ may be C, but embodiments are not limited thereto.

In some embodiments, in Formula 1, $X_{11}$ may be N while $X_{12}$ and $X_{13}$ may be C, but embodiments are not limited thereto.

In some embodiments, in Formula 1, $X_{11}$ may be while $X_{12}$ and $X_{13}$ may be N, but embodiments are not limited thereto.

In some embodiments, in Formula 1, $X_{11}$ to $X_{13}$ may be C, but embodiments are not limited thereto.

$X_{14}$ in Formula 1 may be selected from N and a phosphorus atom (P).

For example, $X_{14}$ in Formula 1 may be N, but embodiments are not limited thereto.

$E_{11}$ to $E_{14}$ in Formula 1 may be each independently selected from a single bond and a divalent linking group.

For example, $E_{11}$ to $E_{14}$ in Formula 1 may be each independently selected from a single bond, O, and S, but embodiments are not limited thereto.

In some embodiments, in Formula 1, $X_{11}$ may be C, and $E_{11}$ may be selected from O and S;

$X_{12}$ may be C, and $E_{12}$ may be selected from O and S; and $X_{13}$ may be C, and $E_{13}$ may be selected from O and S, but embodiments are not limited thereto.

In some embodiments, $E_{11}$ to $E_{14}$ in Formula 1 may be a single bond, but embodiments are not limited thereto.

In Formula 1, $Y_{11}$ to $Y_{15}$ may be each independently selected from a single bond and a divalent linking group; $X_{14}$ and $Y_{14}$ may be linked together by a single bond or by a double bond, and $X_{14}$ and $Y_{15}$ may be linked together by a single bond or by a double bond.

For example, in Formula 1, $Y_{11}$ to $Y_{15}$ may be each independently selected from a single bond, a double bond, —O—, —S—, —{B($Q_{11}$)}-, —{N($Q_{12}$)}-, —{C($Q_{11}$)($Q_{12}$)}$_{n11}$-, ={C($Q_{11}$)}$_{n1}$-, —{Si($Q_{11}$)($Q_{12}$)}$_{n11}$-, —C(=O)—, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$Q_{11}$ and $Q_{12}$ may be each independently selected from a hydrogen, a deuterium, a $C_1$-$C_{60}$ alkyl group, a $C_6$-$C_{60}$ aryl group, and a $C_1$-$C_{60}$ heteroaryl group; and n11 may be selected from 1, 2, and 3, but embodiments are not limited thereto.

In some embodiments, in Formula 1, $Y_{11}$ to $Y_{15}$ may be each independently selected from a single bond, a double bond, —O—, —S—, —{B($Q_{11}$)}-, —{N($Q_{11}$)}-, —{C($Q_{11}$)($Q_{12}$)}$_{n1}$-, ={C($Q_{11}$)}$_{n1}$-, —{Si($Q_{11}$)($Q_{12}$)}$_{n1}$-, —C(=O)—, a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group, and a dibenzothiophenylene group; and a phenylene group, a naphthylene group, a fluorenylene group, a pyridinylene group, a pyrazinylene group, a pyrimidinylene group, a quinolinylene group, an isoquinolinylene group, a naphthyridinylene group, a quinoxalinylene group, a quinazolinylene group, a dibenzofuranylene group, and a dibenzothiophenylene group, each substituted with at least one selected from a deuterium, —F, —Cl, —Br, —I, a methyl group, an ethyl group, an n-propyl group, an iso-propyl group, an n-butyl group, an iso-butyl group, a sec-butyl group, a tert-butyl group, a phenyl group, and a pyridinyl group;

$Q_{11}$ and $Q_{12}$ may be each independently selected from a hydrogen, a deuterium, a methyl group, an ethyl group, an n-propyl group, an iso-propyl group, an n-butyl group, an iso-butyl group, a tert-butyl group, and a phenyl group; and n11 may be 1, but embodiments are not limited thereto.

In some embodiments, $Y_{11}$ to $Y_{15}$ in Formula 1 may be each independently selected from a single bond, a double bond, —O—, —S—, —N($CH_3$)—, —N(Ph)-, —$CH_2$—, —CH($CH_3$)—, —C($CH_3$)$_2$—, —C($CH_3$)(Ph)-, —C(Ph)$_2$-, =C($CH_3$)—, =C(Ph)-, —C(=O)—, and groups represented by Formulae 4-1 to 4-17 below, but embodiments are not limited thereto:

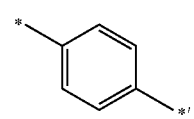

4-1

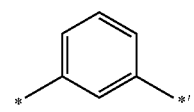

4-2

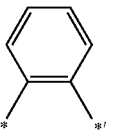

4-3

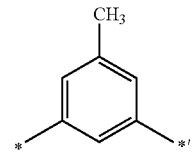

4-4

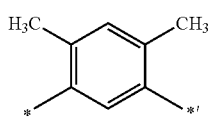
4-5

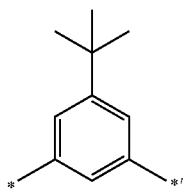
4-6

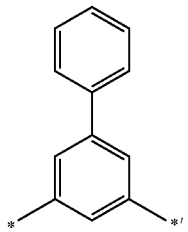
4-7

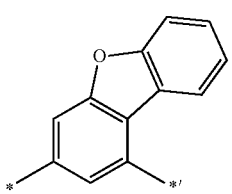
4-8

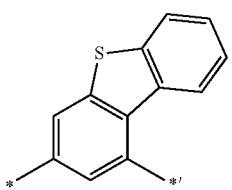
4-9

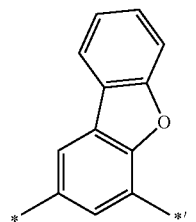
4-10

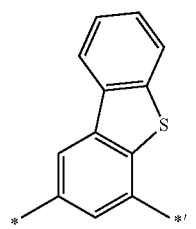
4-11

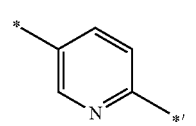
4-12

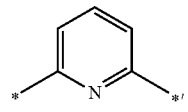
4-13

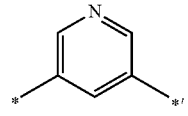
4-14

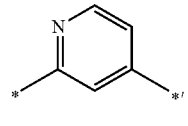
4-15

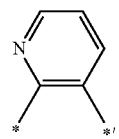
4-16

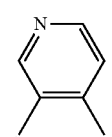
4-17

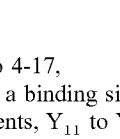

In Formulae 4-1 to 4-17, each of * and *' is a binding site to a neighboring atom.

In some embodiments, $Y_{11}$ to $Y_{13}$ in Formula 1 may be each independently selected from a single bond, a double bond, —O—, —S—, —N(CH$_3$)—, —N(Ph)-, —CH$_2$—, —CH(CH$_3$)—, —C(CH$_3$)$_2$—, and —C(=O)—, but embodiments are not limited thereto.

In some embodiments, $Y_{14}$ and $Y_{15}$ in Formula 1 may be each independently selected from a single bond, a double bond, —CH$_2$—, =C(CH$_3$)—, =C(Ph)-, and —C(=O)—, but embodiments are not limited thereto.

$L_{11}$ in Formula 1 may be selected from a monodentate ligand and a bidentate ligand.

For example, $L_{11}$ in Formula 1 may be selected from I⁻, Br⁻, Cl⁻, a sulfide, a nitrate, an azide, a hydroxide, a cyanate, an isocyanate, a thiocyanate, water, an acetonitrile, a pyridine, an ammonia, a carbon monoxide, P(Ph)$_3$, P(Ph)$_2$CH$_3$, PPh(CH$_3$)$_2$, and P(CH$_3$)$_3$; and an oxalate, an acetylacetonate, a picolinic acid, a 1,2-bis (diphenylphosphino)ethane, a 1,1-bis(diphenylphosphino) methane, a glycinate, and an ethylenediamine, but embodiments are not limited thereto.

In some embodiments, $L_{11}$ in Formula 1 may be selected from P(Ph)$_3$, P(Ph)$_2$CH$_3$, PPh(CH$_3$)$_2$, P(CH$_3$)$_3$, an oxalate, an acetylacetonate, and a picolinic acid, but embodiments are not limited thereto.

In some embodiments, $L_{11}$ in Formula 1 may be selected from P(Ph)$_2$CH$_3$ and an acetylacetonate, but embodiments are not limited thereto.

a11 in Formula 1 denotes the number of $L_{11}$ and may be selected from 0, 1, and 2.

For example, in Formula 1, $L_{11}$ may be a monodentate ligand, and a11 may be 2, but embodiments are not limited thereto. In other words, $L_{11}$ in Formula 1 may be selected from I⁻, Br⁻, Cl⁻, a sulfide, a nitrate, an azide, a hydroxide, a cyanate, an isocyanate, a thiocyanate, water, an acetonitrile, a pyridine, an ammonia, a carbon monoxide, P(Ph)$_3$, P(Ph)$_2$CH$_3$, PPh(CH$_3$)$_2$, and P(CH$_3$)$_3$, and a11 may be 2, but embodiments are not limited thereto.

In some embodiments, in Formula 1, L$_{11}$ may be a bidentate ligand, a11 may be 1, but embodiments are not limited thereto. In other words, in Formula 1, L$_{11}$ may be an oxalate, an acetylacetonate, a picolinic acid, a 1,2-bis(diphenylphosphino)ethane, a 1,1-bis(diphenylphosphino)methane, a glycinate, and an ethylenediamine, and a11 may be 1, but embodiments are not limited thereto.

In some embodiments, a11 in Formula 1 may be 0, but embodiments are not limited thereto.

In Formula 1, R$_{11}$ to R$_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —C(=O)(Q$_1$), —Si(Q$_1$)(Q$_2$)(Q$_3$), and —N(Q$_1$)(Q$_2$);

Q$_1$ to Q$_3$ may be each independently selected from a C$_1$-C$_{60}$ alkyl group and a C$_6$-C$_{60}$ aryl group; and at least one substituent of the substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_1$-C$_{10}$ heterocycloalkyl group, substituted C$_3$-C$_{10}$ cycloalkenyl group, substituted C$_1$-C$_{10}$ heterocycloalkenyl group, substituted C$_6$-C$_{60}$ aryl group, substituted C$_6$-C$_{60}$ aryloxy group, substituted C$_6$-C$_{60}$ arylthio group, substituted C$_1$-C$_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group.

For example, in Formula 1, R$_{11}$ to R$_{13}$ may be each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —CF$_3$, a methoxy group, an ethoxy group, a tert-butoxy group, a phenyl group, —C(=O)(Q$_1$), —Si(Q$_1$)(Q$_2$)(Q$_3$), and —N(Q$_1$)(Q$_2$); and Q$_1$ to Q$_3$ may be each independently selected from a methyl group, an ethyl group, an n-propyl group, an iso-propyl group, an n-butyl group, iso-butyl group, a sec-butyl group, a tert-butyl group, and a phenyl group, but embodiments are not limited thereto.

In some embodiments, in Formula 1, R$_{11}$ to R$_{13}$ may be each independently selected from a hydrogen, a deuterium, —F, a cyano group, a methyl group, an ethyl group, an n-propyl group, an iso-propyl group, an n-butyl group, an iso-butyl group, a sec-butyl group, a tert-butyl group, —CF$_3$, —C(=O)(Q$_1$), —Si(Q$_1$)(Q$_2$)(Q$_3$), and —N(Q$_1$)(Q$_2$); and Q$_1$ to Q$_3$ may be each independently selected from a methyl group, an ethyl group, an n-propyl group, an iso-propyl group, an n-butyl group, an iso-butyl group, a sec-butyl group, a tert-butyl group, and a phenyl group, but embodiments are not limited thereto.

In some embodiments, R$_{11}$ to R$_{13}$ in Formula 1 may be each independently selected from a hydrogen, —F, a cyano group, a methyl group, an iso-propyl group, a tert-butyl group, —CF$_3$, and —Si(CH$_3$)$_3$, but embodiments are not limited thereto.

b11 in Formula 1 denotes the number of R$_{11}$ and may be selected from 1, 2, 3, 4, 5, 6, 7, 8, 9, and 10.

b12 in Formula 1 denotes the number of R$_{12}$ and may be selected from 1, 2, 3, 4, 5, 6, 7, 8, 9, and 10.

b13 in Formula 1 denotes the number of R$_{13}$ and may be selected from 1, 2, 3, 4, 5, 6, 7, 8, 9, and 10.

For example, the organometallic compound may be selected from groups represented by Formulae 1-1 to 1-3, but embodiments are not limited thereto:

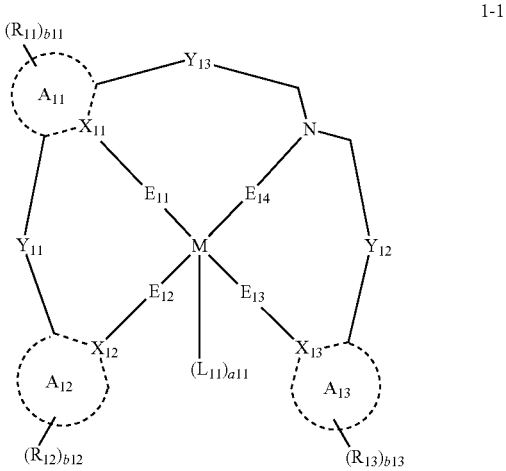

-continued 1-2
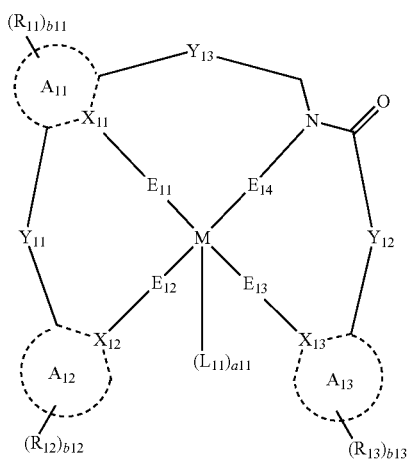

1-3
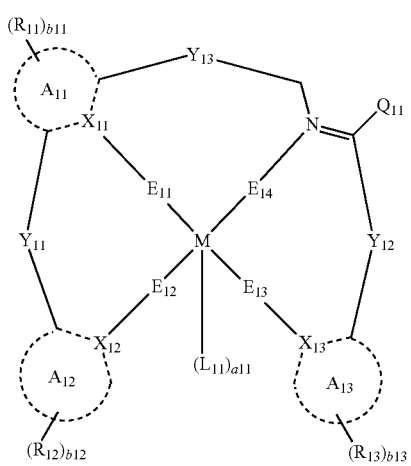

In Formulae 1-1 to 1-3, $M$, $A_{11}$ to $A_{13}$, $X_{11}$ to $X_{13}$, $E_{11}$ to $E_{14}$, $Y_{11}$ to $Y_{13}$, $L_{11}$, $a11$, $R_{11}$ to $R_{13}$, and $b11$ to $b13$ are the same as defined with respect to Formula 1; and $Q11$ may be selected from a hydrogen, a deuterium, a $C_1$-$C_{60}$ alkyl group, a $C_6$-$C_{60}$ aryl group, and a $C_1$-$C_{60}$ heteroaryl group.

In some embodiments, the organometallic compound may be selected from groups represented by Formulae 1-11 to 1-16 below, but embodiments are not limited thereto:

1-11
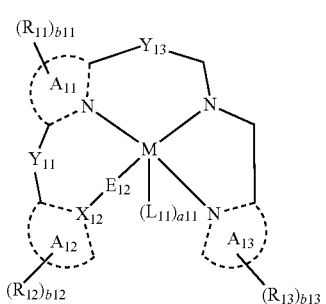

-continued 1-12
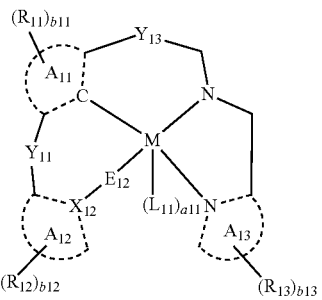

1-13
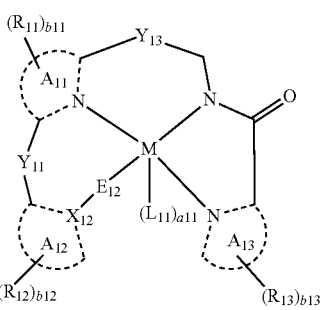

1-14
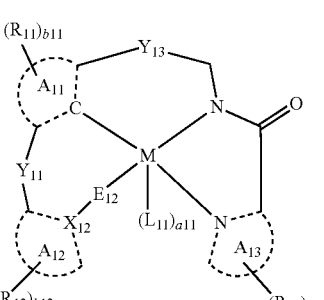

1-15
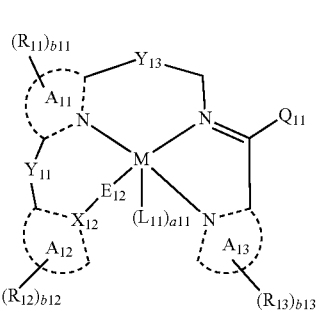

1-16
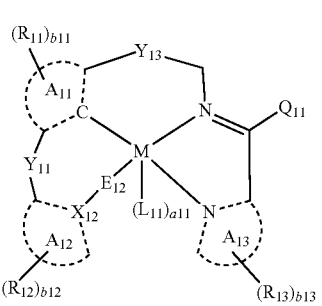

In Formulae 1-11 to 1-16, $M$, $A_{11}$ to $A_{13}$, $X_{12}$, $E_{12}$, $Y_{11}$, $Y_{13}$, $L_{11}$, $a11$, $R_{11}$ to $R_{13}$, and $b11$ to $b13$ are the same as defined with respect to Formula 1; and $Q_{11}$ may be selected from a hydrogen, a deuterium, a methyl group, an ethyl group, an n-propyl group, an iso-propyl group, an n-butyl group, an iso-butyl group, a tert-butyl group, and a phenyl group.
In some embodiments, the organometallic compound may be selected from groups represented by Formulae 1-21 and 1-38, but embodiments are not limited thereto:
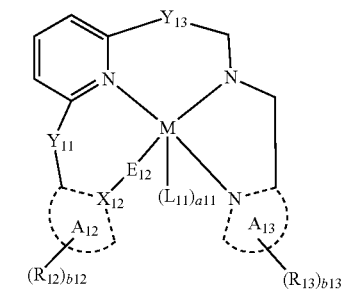
1-21
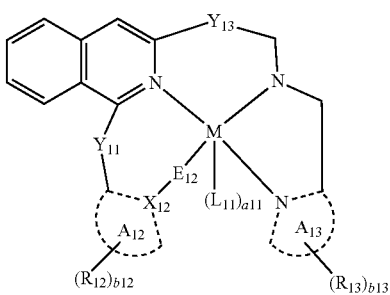
1-22
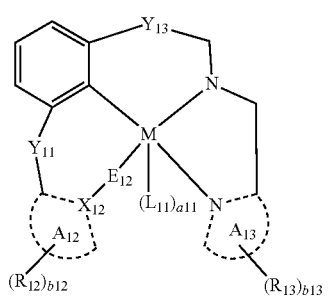
1-23
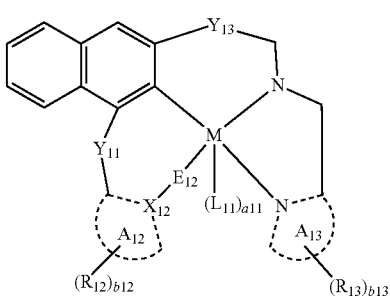
1-24
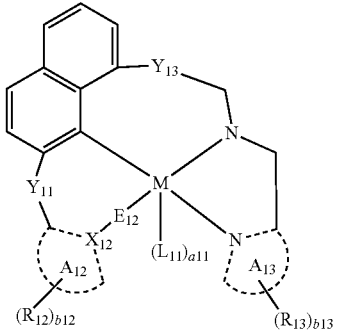
1-25
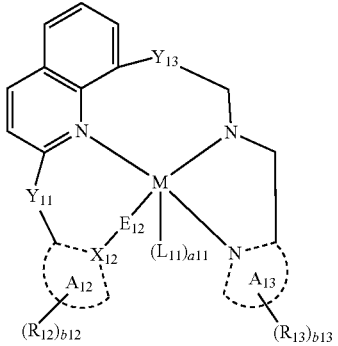
1-26
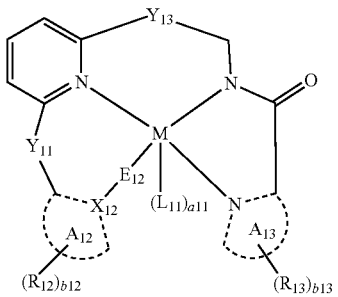
1-27
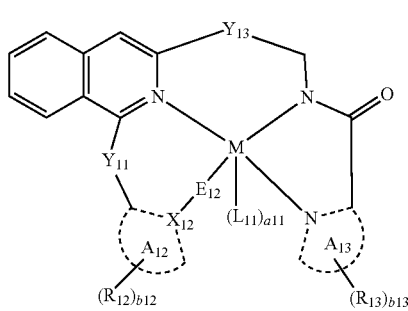
1-28
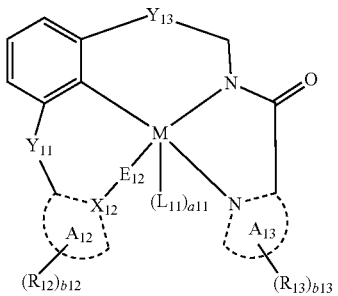
1-29

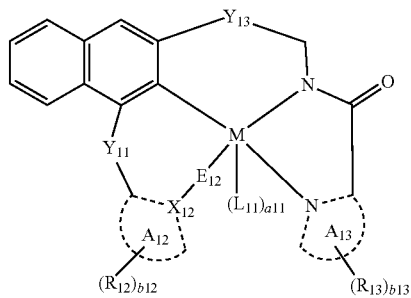

1-30

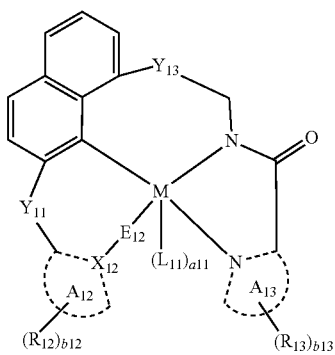

1-31

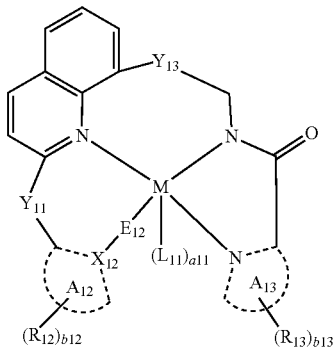

1-32

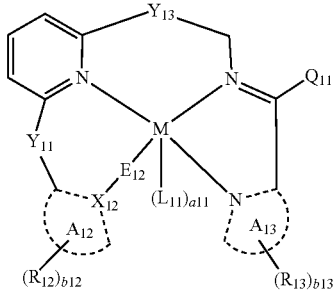

1-33

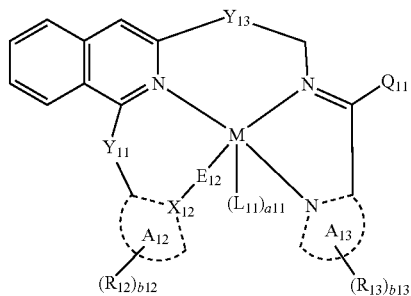

1-34

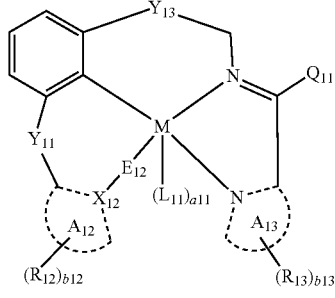

1-35

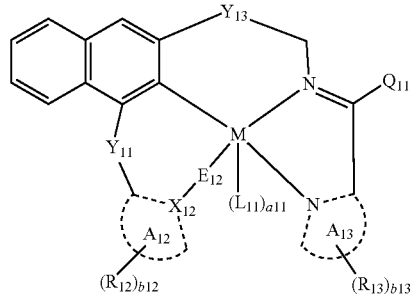

1-36

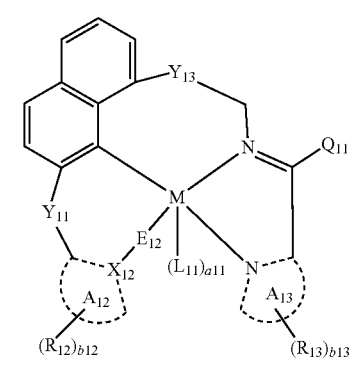

1-37

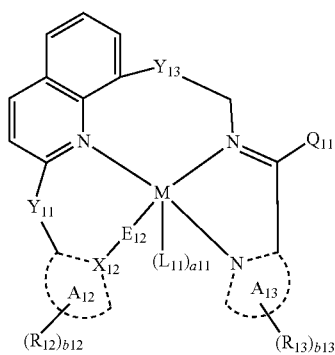

1-38

In Formulae 1-21 to 1-38,

M, $A_{l2}$, $A_{13}$, $X_{12}$, $E_{12}$, $Y_{11}$, $Y_{13}$, $L_{11}$, a11, $R_{12}$, $R_{13}$, b12, and b13 are the same as defined with respect to Formula 1; and $Q_{11}$ may be selected from a hydrogen, a deuterium, a methyl group, an ethyl group, an n-propyl group, an iso-propyl group, an n-butyl group, an iso-butyl group, a tert-butyl group, and a phenyl group.

In some embodiments, the organometallic compound may be selected from groups represented by Formulae 1-41 to 1-52, but embodiments are not limited thereto:

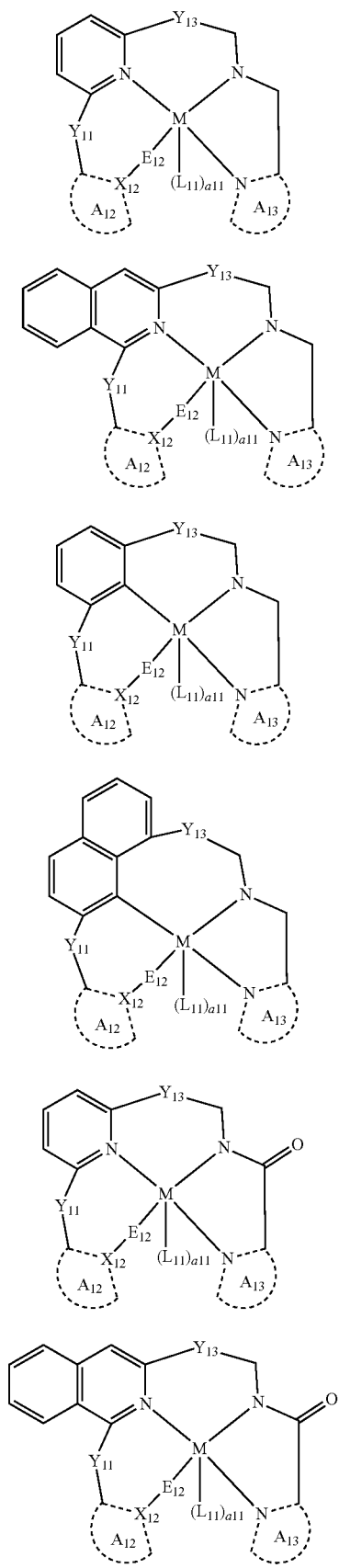
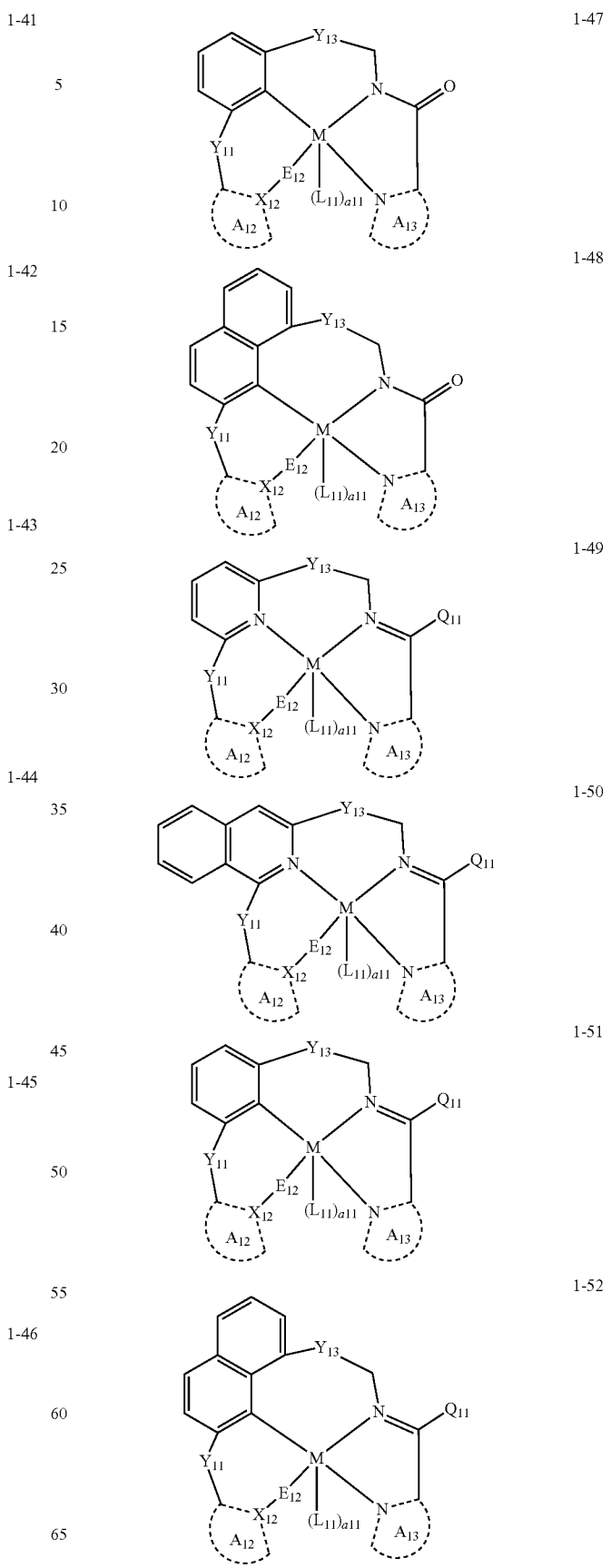

In Formulae 1-41 to 1-52,

M, $X_{12}$, $E_{12}$, $Y_{11}$, $Y_{13}$, $L_{11}$, and a11 are the same as defined with respect to Formula 1;

$Q_{11}$ may be selected from a hydrogen, a deuterium, a methyl group, an ethyl group, an n-propyl group, an iso-propyl group, an n-butyl group, an iso-butyl group, a tert-butyl group, and a phenyl group; and $A_{12}$ and $A_{13}$ may be each independently selected from groups represented by Formulae 3-1 to 3-9;

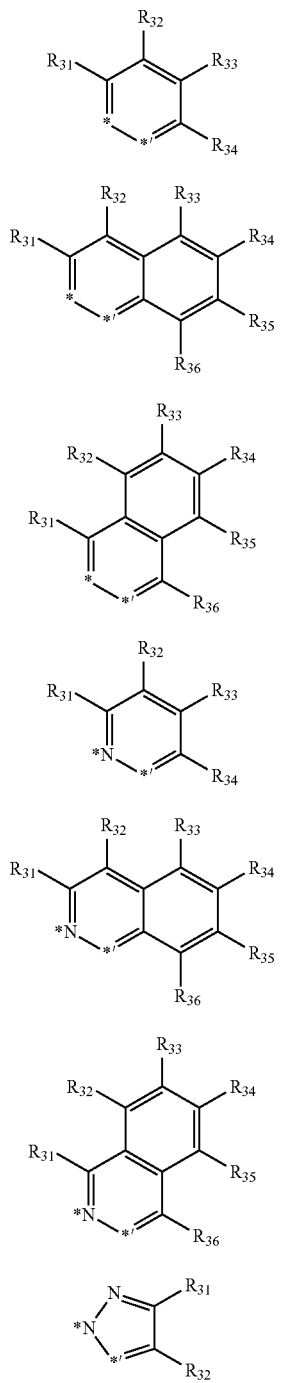

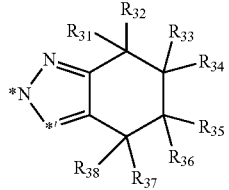

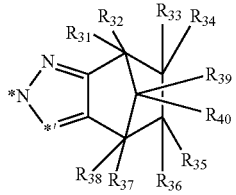

In Formulae 3-1 to 3-9,

* is a binding site to M or $E_{12}$;

*' is a binding site to a neighboring atom; and $R_{31}$ to $R_{40}$ may be each independently selected from a hydrogen, —F, a cyano group, a methyl group, an iso-propyl group, a tert-butyl group, —$CF_3$, and —$Si(CH_3)_3$.

In some embodiments, the organometallic compound may be selected from Compounds PD-1 to PD-67 below, but embodiments are not limited thereto:

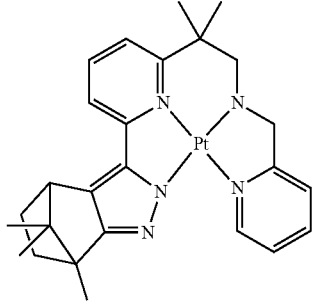

PD-1

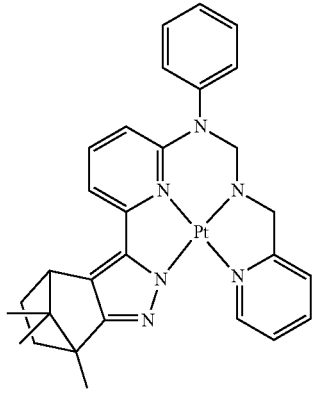

PD-2

-continued
PD-3
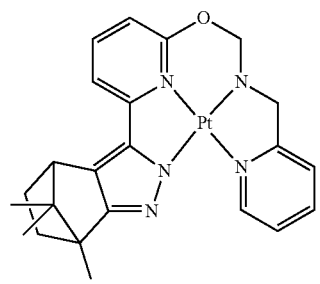
PD-4
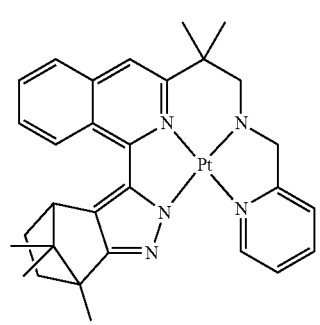
PD-5
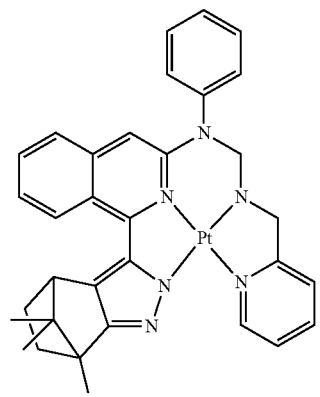
PD-6
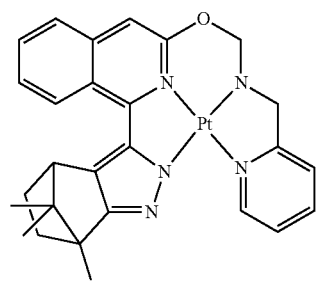
PD-7
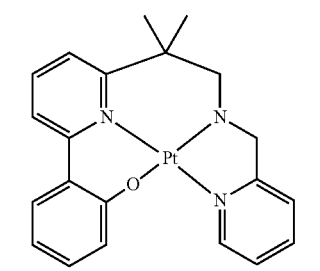
-continued
PD-8
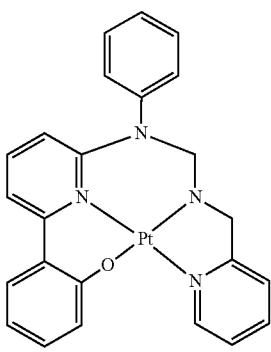
PD-9
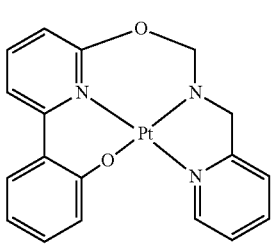
PD-10
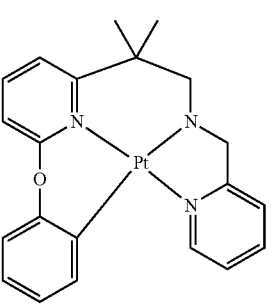
PD-11
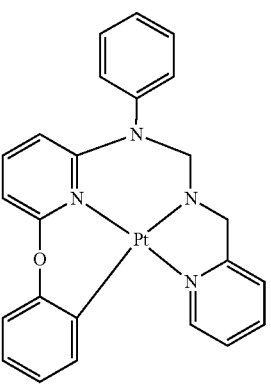
PD-12
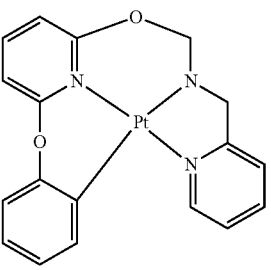

-continued
PD-13
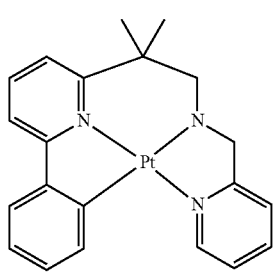
PD-14
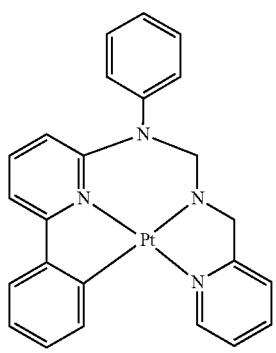
PD-15
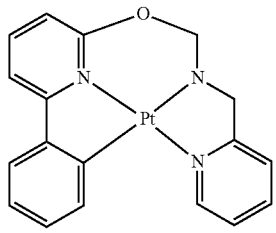
PD-22
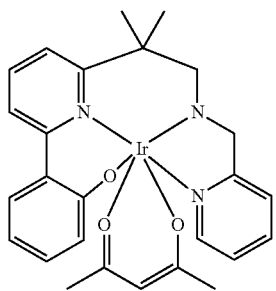
PD-23
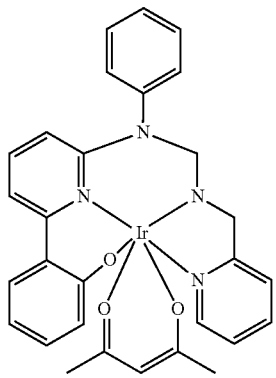
-continued
PD-24
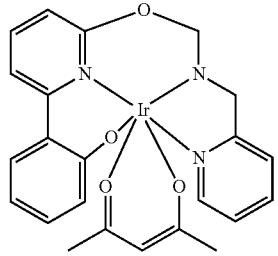
PD-25
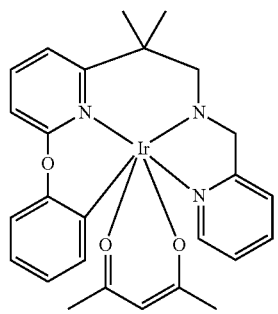
PD-26
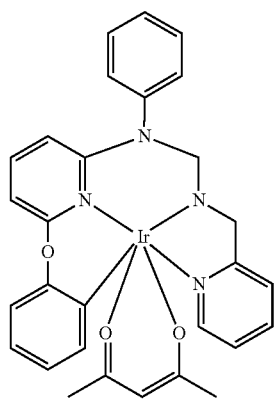
PD-27
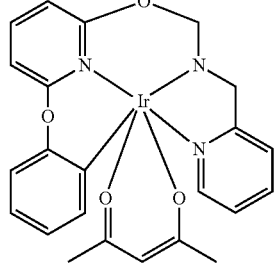
PD-28
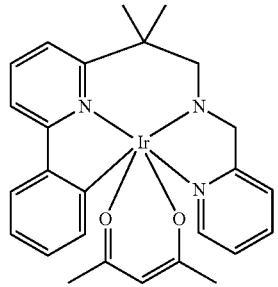

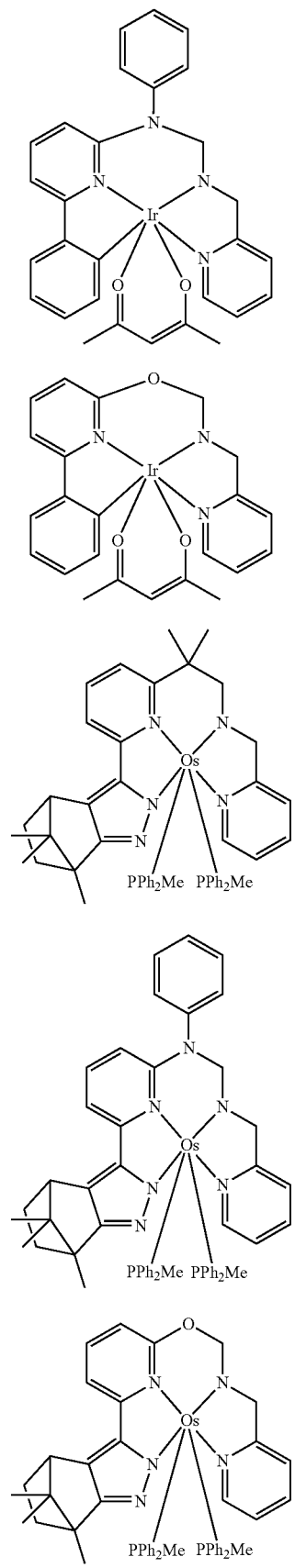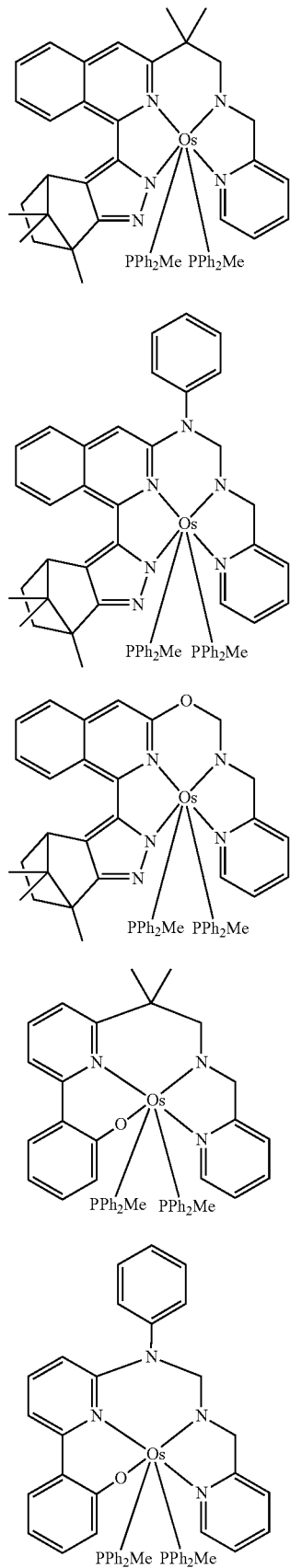

PD-39
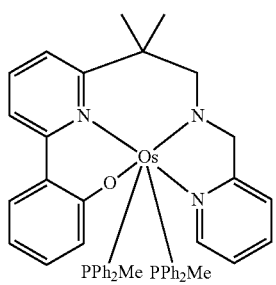
PD-40
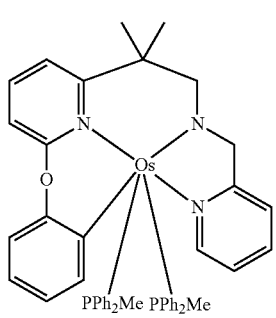
PD-41
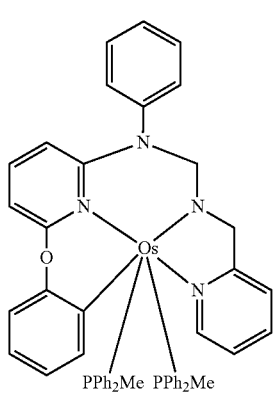
PD-42
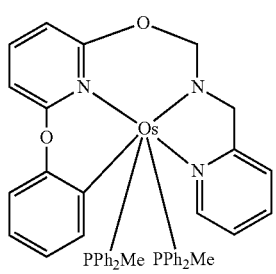
PD-43
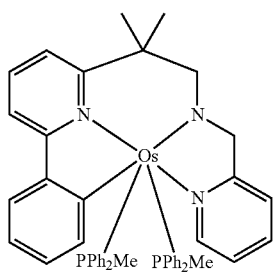
PD-44
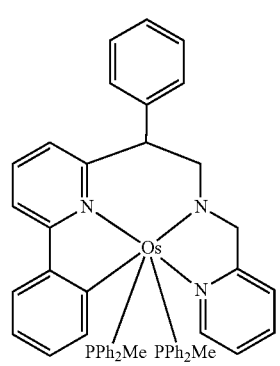
PD-45
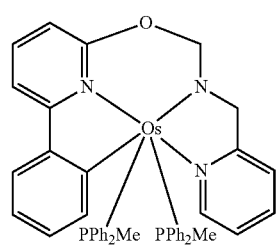
PD-46
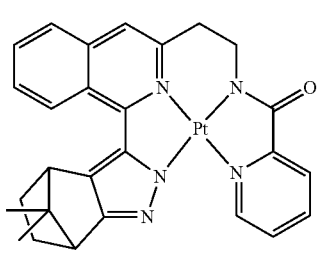
PD-47
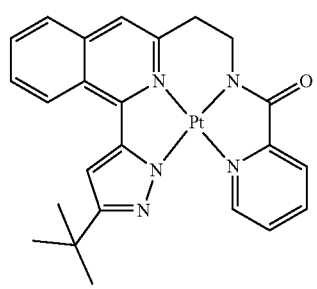
PD-48
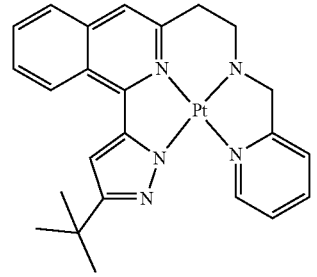

PD-49
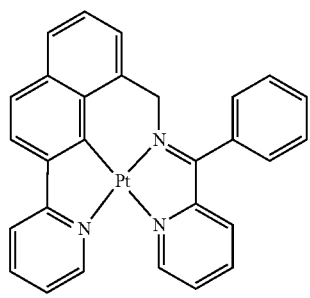
PD-50
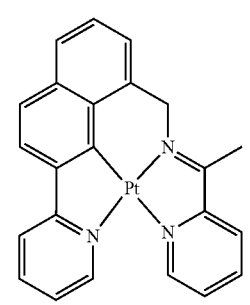
PD-51
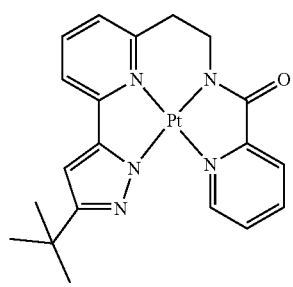
PD-52
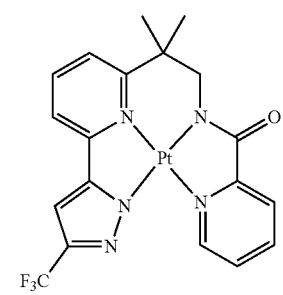
PD-53
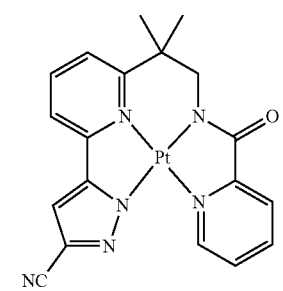
PD-54
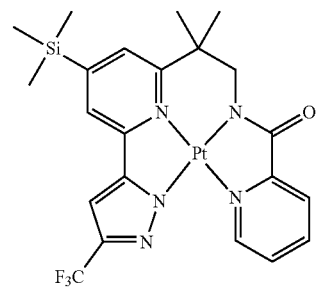
PD-55
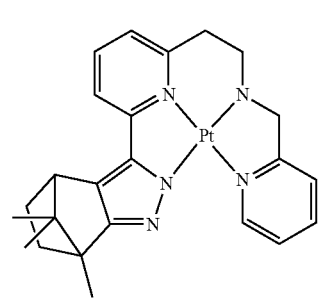
PD-56
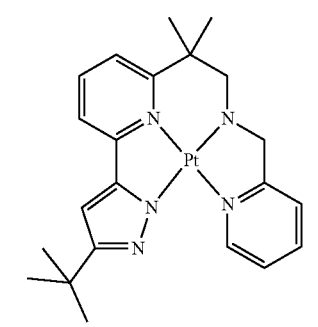
PD-57
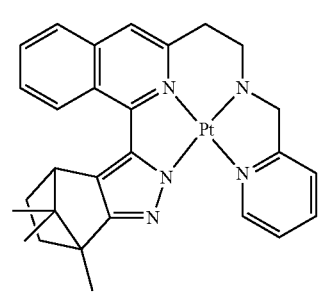
PD-58
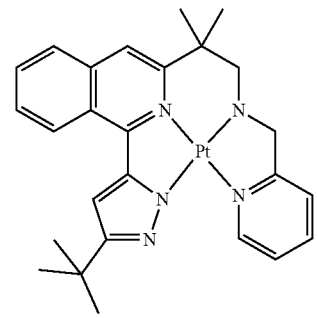

-continued
PD-59
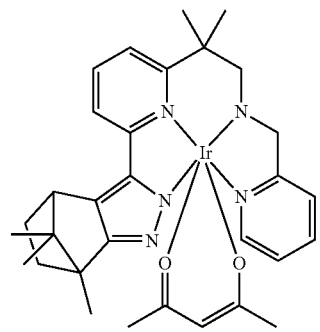
PD-60
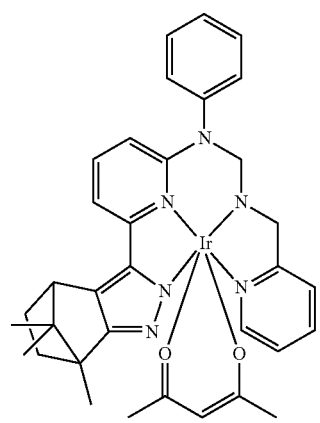
PD-61
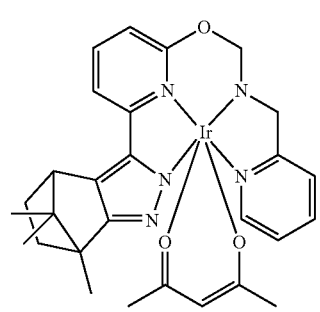
PD-62
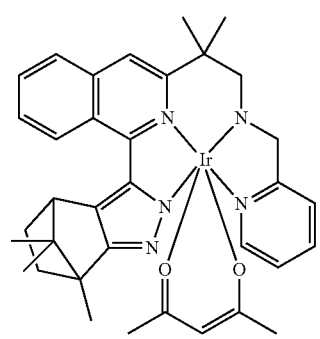
-continued
PD-63
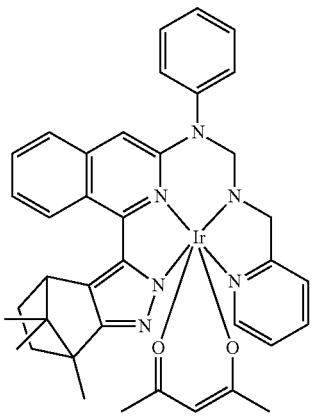
PD-64
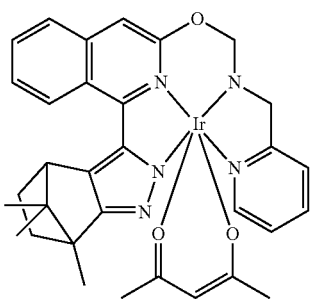
PD-65
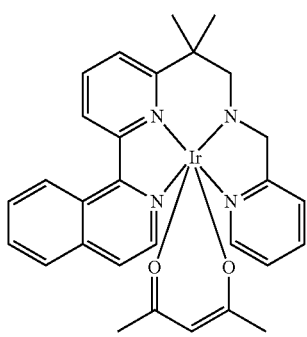
PD-66
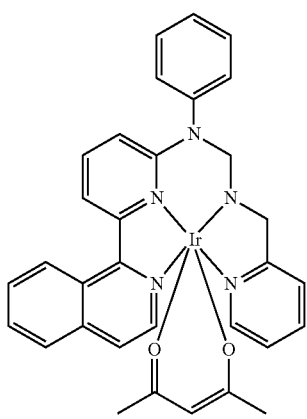

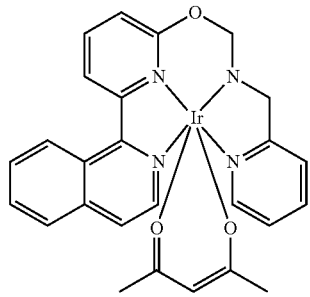

PD-67

In Formula 1, since $X_{14}$ is N and does not form a ring, an organic light-emitting device including the organometallic compound represented by Formula 1 does not have a square planar structure with respect to a central metal thereby having an excellent quantum efficiency. Also, the substituents in the organometallic compound represented by Formula 1 may be changed in various ways in order to synthesize a material having an excellent efficiency and a long lifespan.

Various substituents in the marked position of the organometallic compound represented by Formula 1 may be employed, as described in Formula 1' below, and thus, an organic light-emitting device with excellent efficiency and long lifespan may be provided. In addition, by employing various substituents, an organometallic compound emitting light with a desired wavelength may be provided.

functional theory (DFT) based on B3LYP, and the results thereof are shown in Table 1 below.

TABLE 1

|  | HOMO (eV) | LUMO (eV) | $S_1$ (eV) | $T_1$ (eV) | $\lambda_{max}$ (nm) |
| --- | --- | --- | --- | --- | --- |
| Compound PD-46 | −4.965 | −2.112 | 2.214 | 1.950 | 635 |
| Compound PD-47 | −5.138 | −2.180 | 2.314 | 2.016 | 615 |
| Compound PD-48 | −4.410 | −1.822 | 1.999 | 1.760 | 704 |
| Compound PD-49 | −4.955 | −1.807 | 2.457 | 2.069 | 599 |
| Compound PD-50 | −4.963 | −1.776 | 2.495 | 2.084 | 595 |
| Compound PD-51 | −5.149 | −1.949 | 2.500 | 2.234 | 555 |
| Compound PD-52 | −5.450 | −2.142 | 2.596 | 2.328 | 532 |
| Compound PD-53 | −5.565 | −2.265 | 2.595 | 2.341 | 529 |
| Compound PD-54 | −5.378 | −2.111 | 2.562 | 2.312 | 536 |
| Compound A | −5.075 | −1.430 | 2.882 | 2.441 | 508 |
| Compound B | −5.284 | −1.675 | 2.565 | 2.241 | 553 |

Fomrula 1'

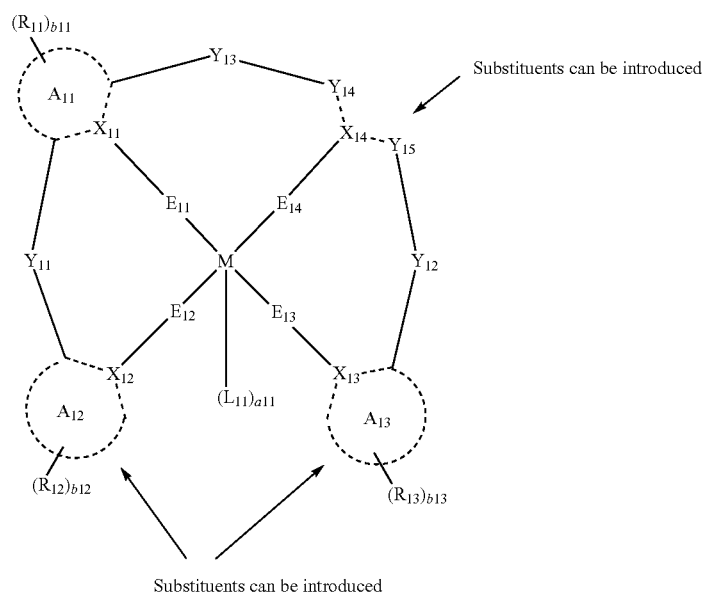

Substituents can be introduced

Substituents can be introduced

For example, the organometallic compound represented by Formula 1 has a maximum emission wavelength of about 700 nanometers (nm) to about 505 nm and may emit green light or red light wherein the green light has an x color coordinate of about 0.210 to about 0.290, a y color coordinate of about 0.340 to about 0.840, the red light has an x color coordinate of about 0.540 to about 0.740, and a y color coordinate of about 0.160 to about 0.420.

For example, a HOMO energy level, a LUMO energy level, a S1 energy level, a T1 energy level and a maximum emission wavelength of some compounds, from among the organometallic compound represented by Formula 1 are evaluated by using a Gaussian 09 program that performs a molecular structure optimization according to a density TABLE 1-continued

|  | HOMO (eV) | LUMO (eV) | $S_1$ (eV) | $T_1$ (eV) | $\lambda_{max}$ (nm) |
| --- | --- | --- | --- | --- | --- |

PD-46

TABLE 1-continued

| HOMO (eV) | LUMO (eV) | S₁ (eV) | T₁ (eV) | λ_max (nm) |
|---|---|---|---|---|

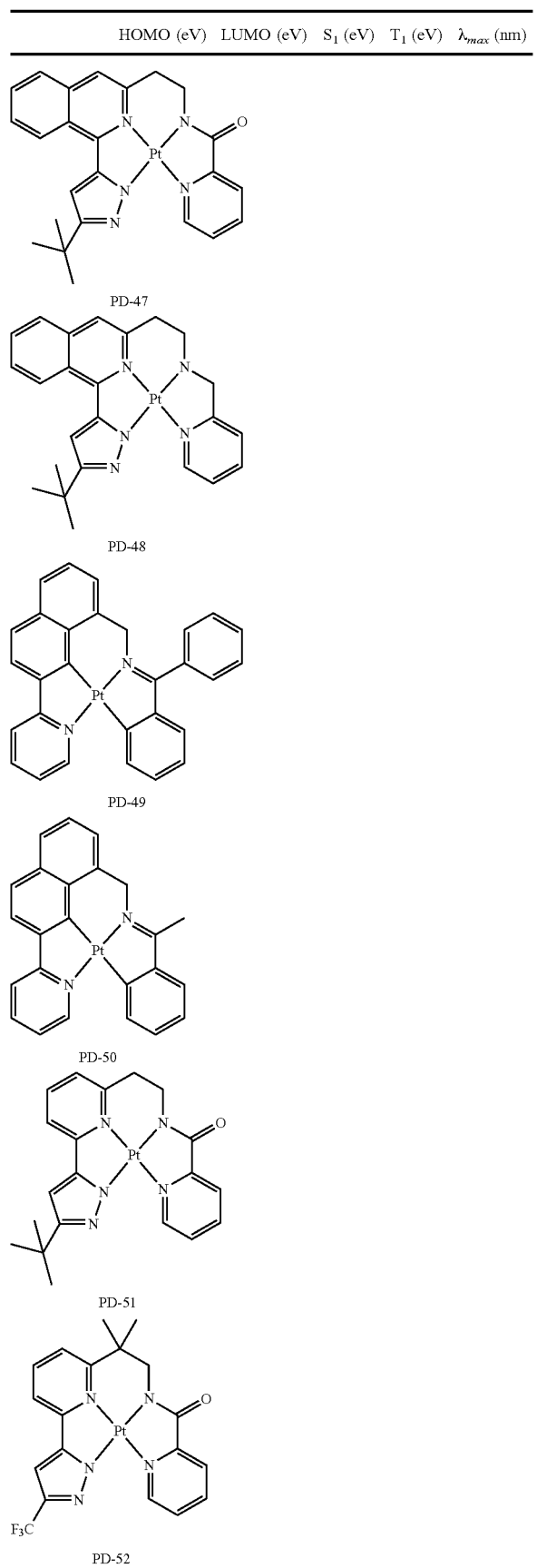

TABLE 1-continued

| HOMO (eV) | LUMO (eV) | S₁ (eV) | T₁ (eV) | λ_max (nm) |
|---|---|---|---|---|

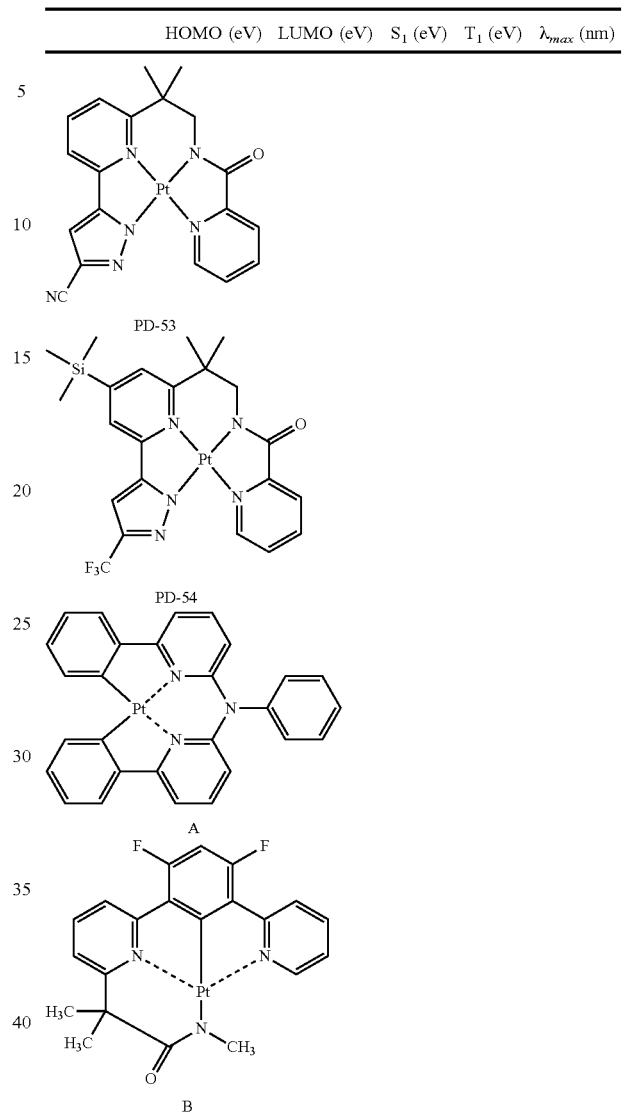

A method of synthesizing the organometallic compound represented by Formula 1 may be apparent to one of ordinary skill in the art by referring to Synthesis Examples disclosed herein.

In this regard, the organometallic compound represented by Formula 1 may be suitable for use as a dopant in an organic layer of an organic light-emitting device, for example, an emission layer in the organic layer. According to another aspect, the organic light-emitting device may include:

a first electrode;
a second electrode; and
an organic layer disposed between the first electrode and the second electrode,
wherein the organic layer includes the emission layer and the organometallic compound represented by Formula 1.

The organic light-emitting device includes the organic layer including the organometallic compound represented by Formula 1, and thereby has low driving voltage, high efficiency, and long lifespan.

The organometallic compound represented by Formula 1 may be used in a pair of electrodes in an organic light-emitting device. For example, the organometallic compound represented by Formula 1 may be included in the emission layer. Here, the organometallic compound may serve as a dopant, and the emission layer may further include a host. The emission layer may emit red light, green light or blue light.

The expression as used herein "(an organic layer) includes at least one organometallic compound" may be understood as "(organic layer) may include one organometallic compound represented by Formula 1 or two or more different organometallic compounds represented by Formula 1".

For example, the organic layer may include only Compound 1 as the organometallic compound. In this regard, Compound 1 may be included in the emission layer of the organic light-emitting device. Alternatively, the organic layer may include Compound 1 and Compound 2 as the organometallic compounds. In this regard, Compound 1 and Compound 2 may be included in the same layer (for example, both Compound 1 and Compound 2 may be included in the emission layer).

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole-transport region disposed between the first electrode and the emission layer, wherein the hole transport region includes at least one selected from a hole injection layer, a hole-transport layer, and an electron blocking layer; and ii) an electron transport region disposed between the emission layer and the second electrode, wherein the electron transport region includes at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by vacuum-depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode.

The material for the first electrode 11 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag).

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer (HIL) may be formed on the first electrode 11 by using various methods such as vacuum-deposition, spin coating, casting, and Langmuir-Blodgett (LB) method.

When a hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0.01 Angstroms per second (Å/sec) to about 100 Å/sec, though the conditions may vary depending on a compound that is used as a hole injection material and a structure and thermal properties of a desired hole injection layer, but it is not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired HIL, but is not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, a spiro-TPD, a spiro-NPB, methylated-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PAN UPSS), a compound represented by Formula 201 below, and a compound represented by Formula 202 below:

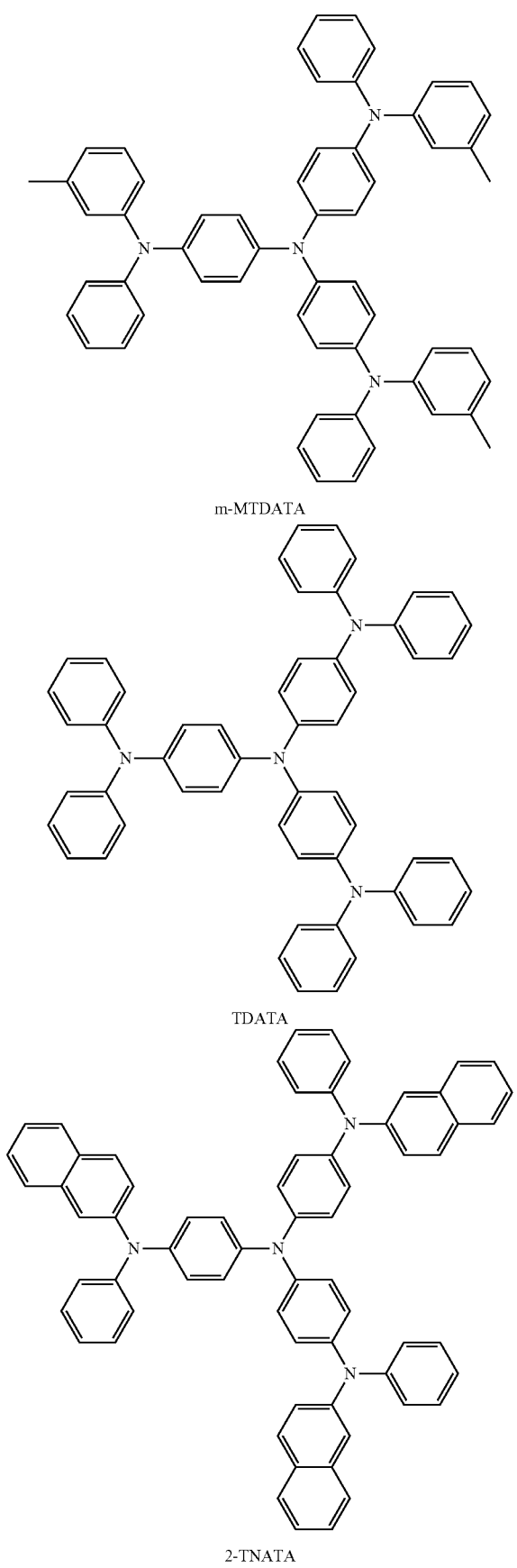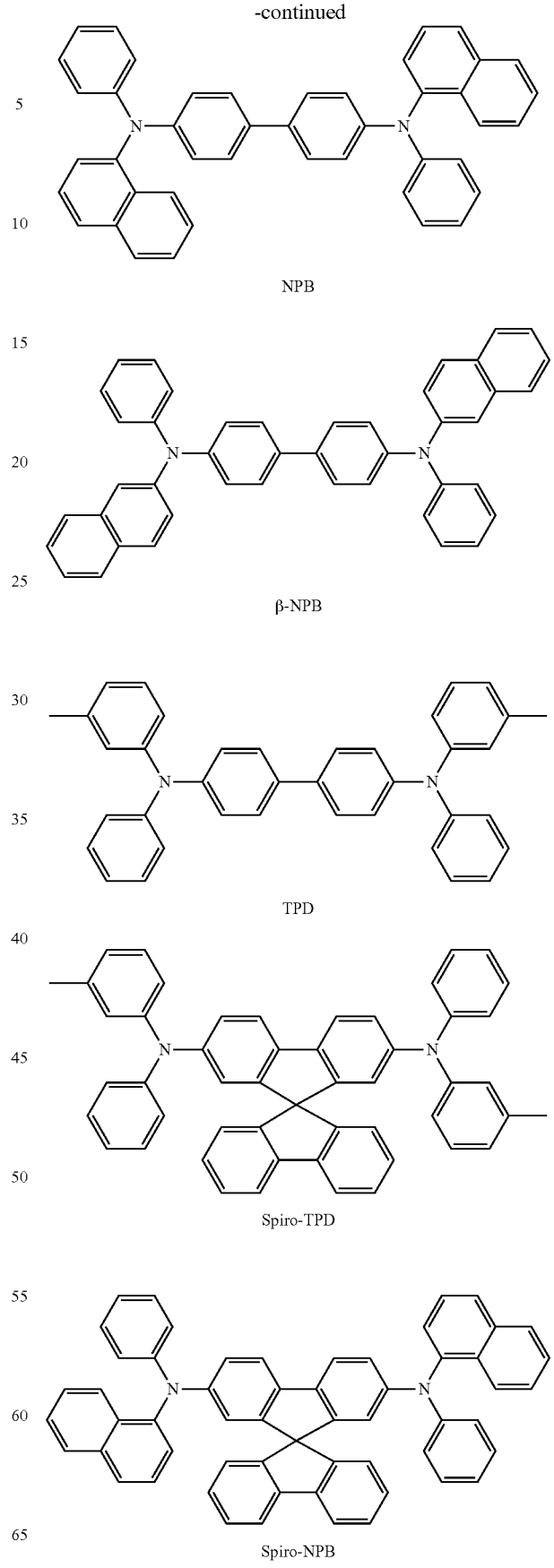

-continued

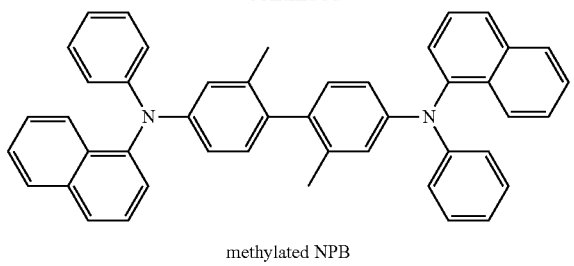

methylated NPB

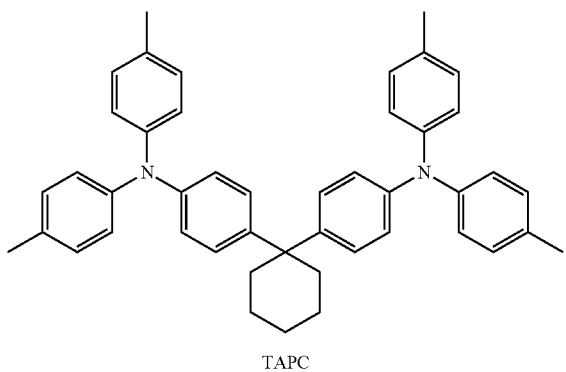

TAPC

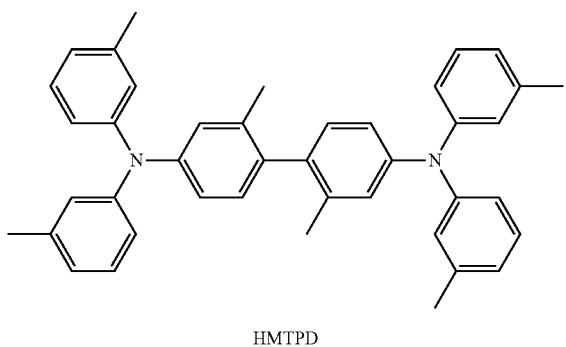

HMTPD

Formula 201

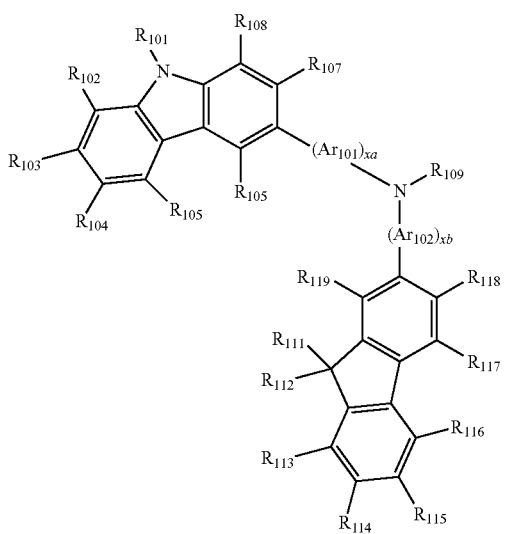

-continued

Formula 202

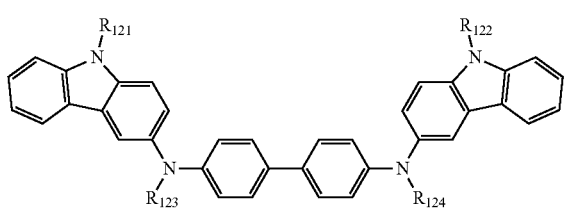

In Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group. xa and xb in Formula 201 may each independently be an integer of 0 to 5, or an integer of 0 to 2. For example, xa may be 1, and xb may be 0, but embodiments are not limited thereto.

$R_{101}$ to $R_{108}$, $R_{111}$ to $R_{119}$, and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group(e.g., a methyl group, an ethyl group, a propyl group, a butyl group, pentyl group, a hexyl group, etc.), and a $C_1$-$C_{10}$ alkoxy group (e.g., a methoxy group, an ethoxy group, a propoxy group, butoxy group, a pentoxy group, etc.);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A below, but embodiments are not limited thereto:

Formula 201A

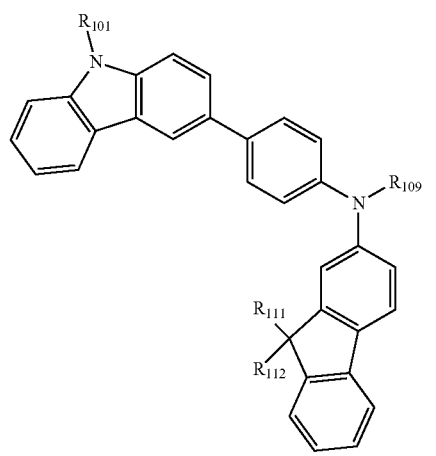

Descriptions for $R_{101}$, $R_{111}$, $R_{112}$, and $R_{109}$ in Formula 201A are the same as described above.

For example, the compound represented by Formula 201 and the compound represented by Formula 202 may include Compounds HT1 to HT20, but embodiments are not limited thereto:

HT1

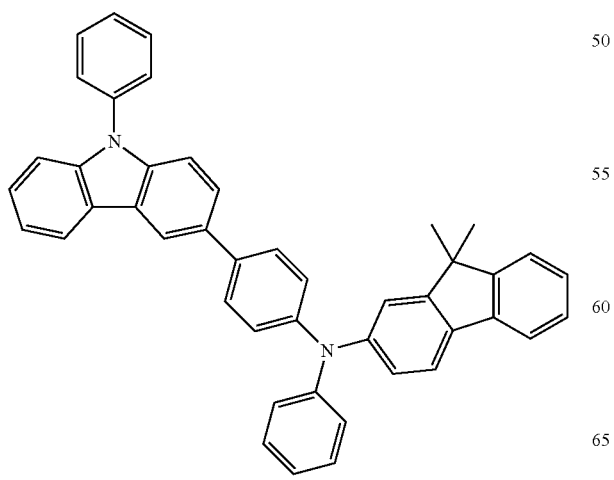

HT2

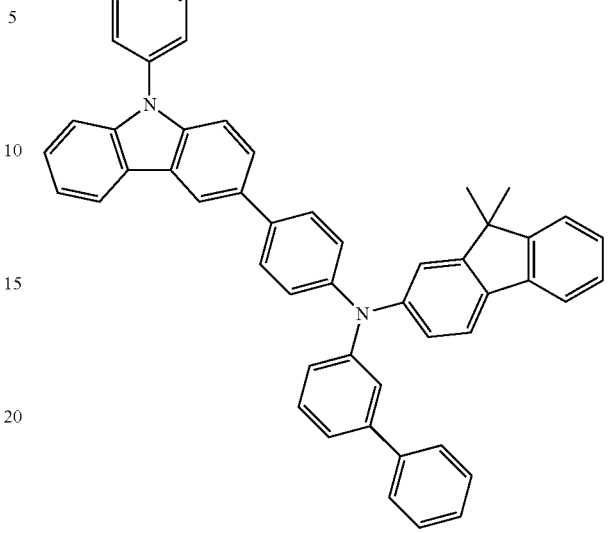

HT3

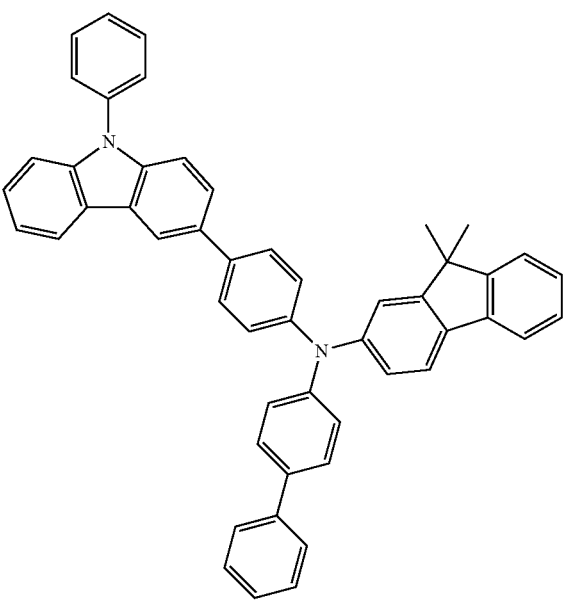

HT4
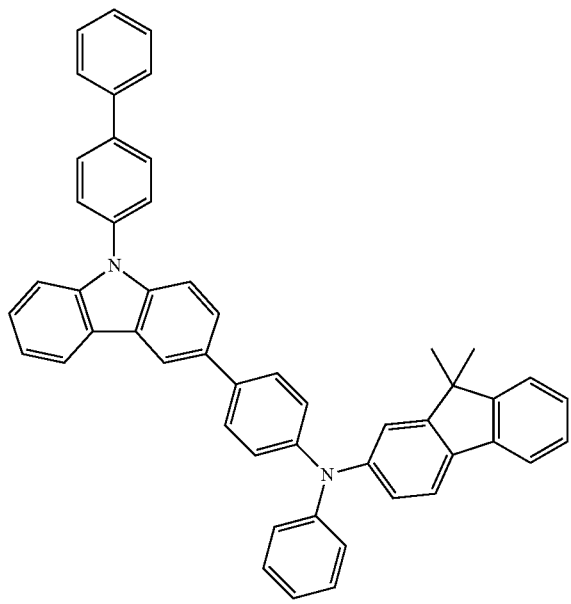
HT6
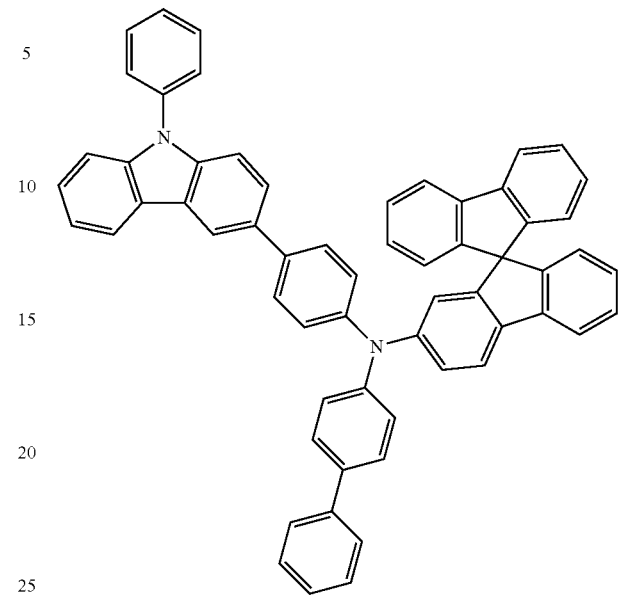
HT5
HT7
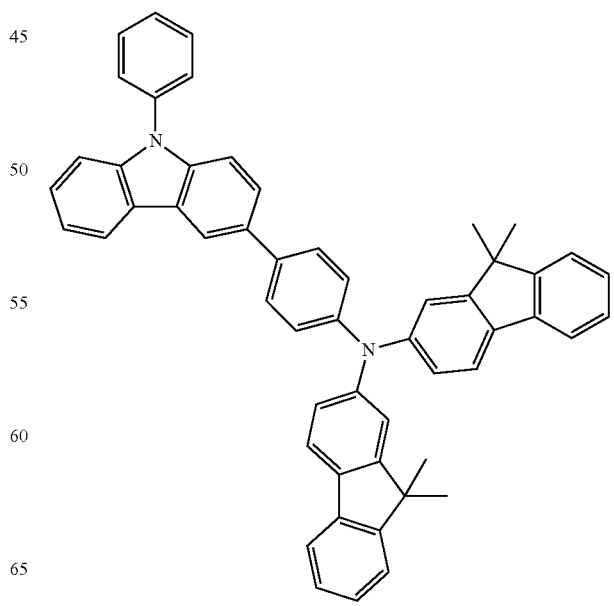

-continued
HT8
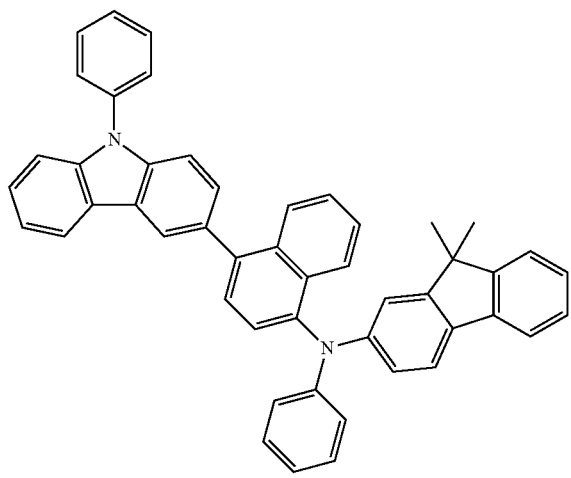
HT9
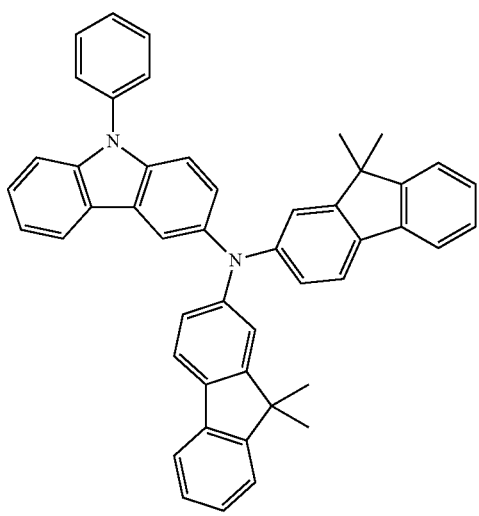
HT10
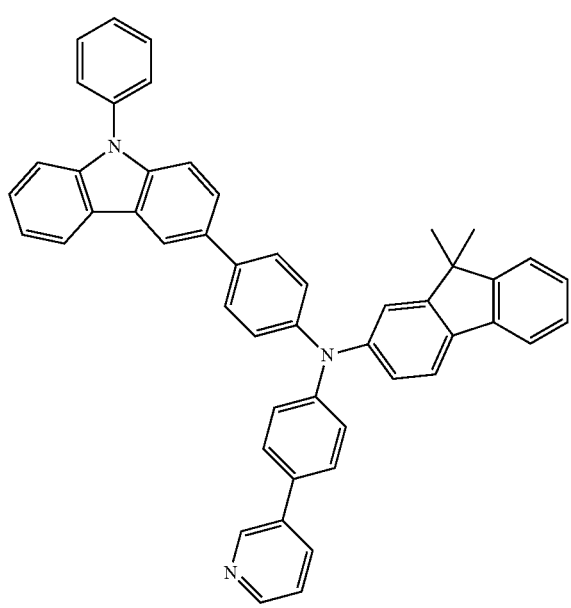
-continued
HT11
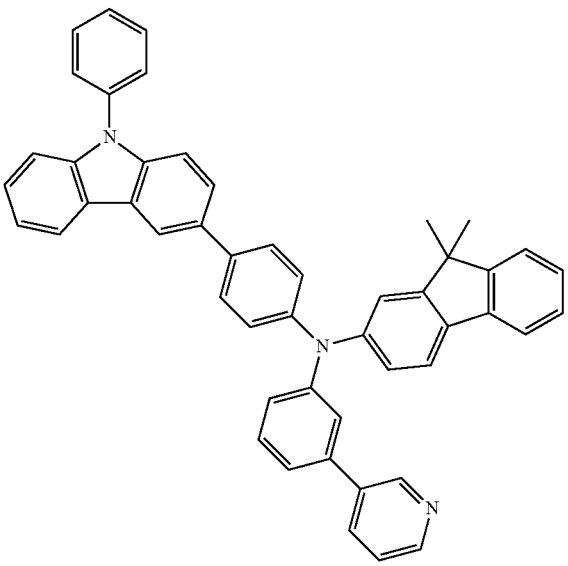
HT12
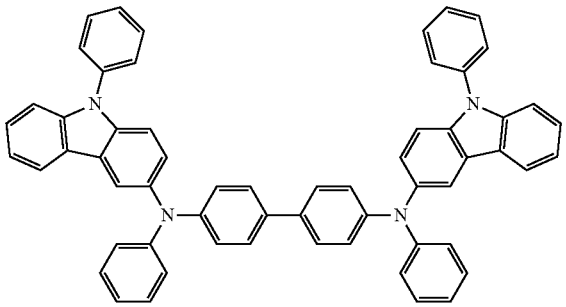
HT13

HT14

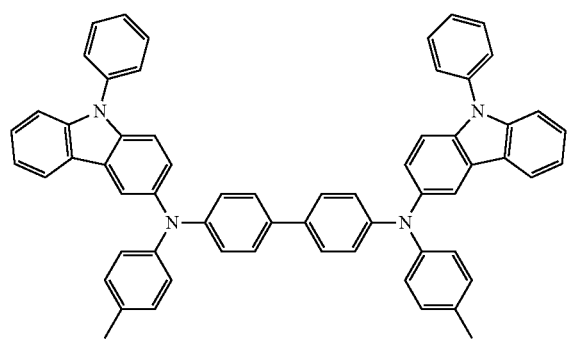

HT15

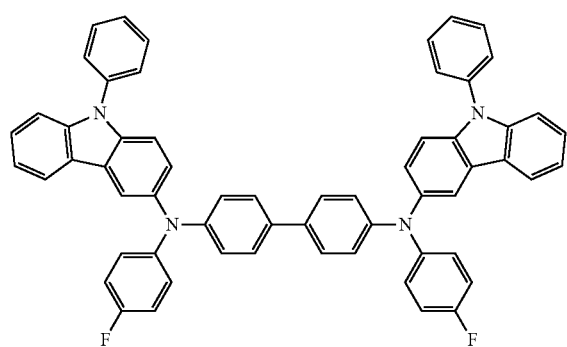

HT16

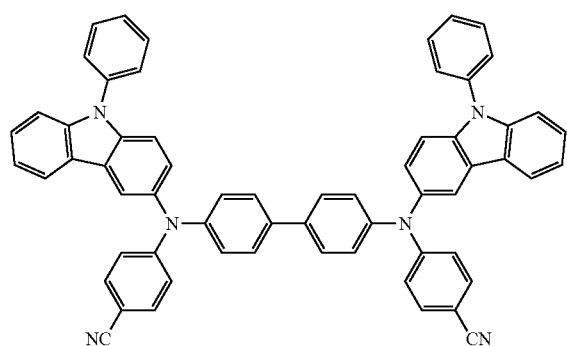

HT17

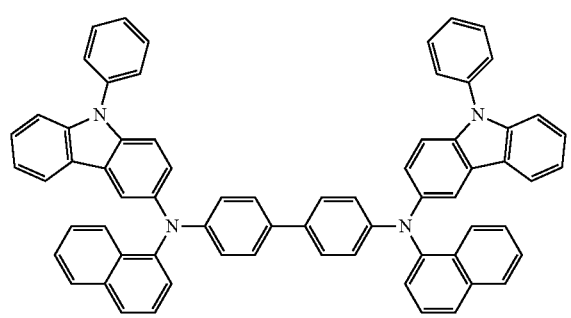

HT18

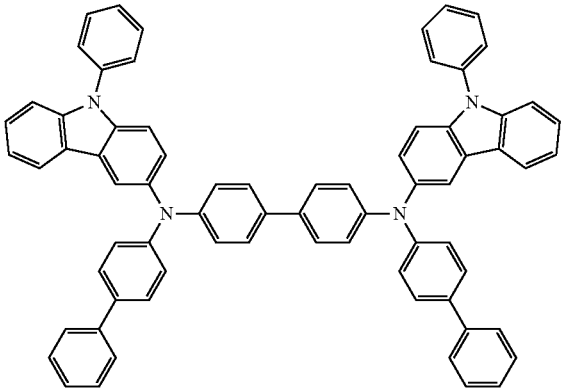

HT19

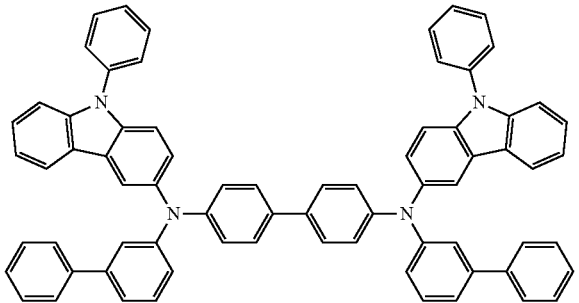

HT20

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 illustrated below, but embodiments are not limited thereto.

Compound HT-D1

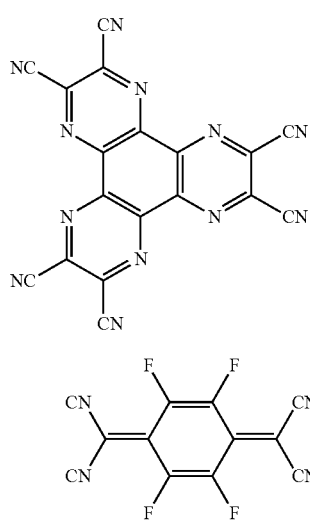

F4-TCNQ

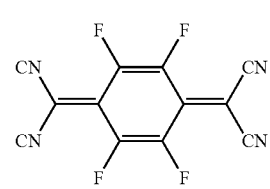

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using various methods, such as vacuum-deposition, spin coating, casting, or an LB method. When the emission layer is formed by vacuum-deposition or spin coating, vacuum-deposition, and coating conditions for the emission layer may be generally similar to the conditions for forming a hole injection layer, though the conditions may vary depending on the compound used.

The emission layer may include a host and a dopant.

The host may include at least one selected from TPBi, TBADN, AND (also known as "DNA"), CBP, CDBP, and TCP:

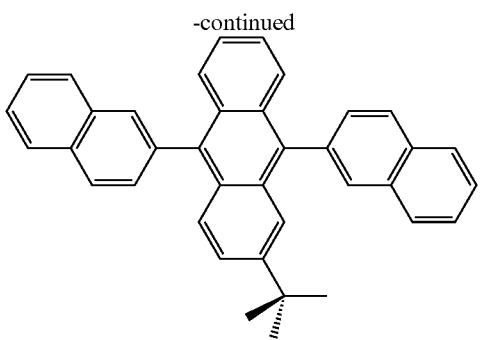

TBADN

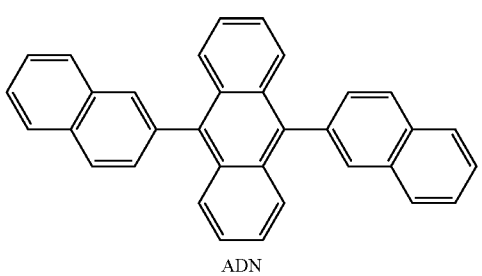

ADN

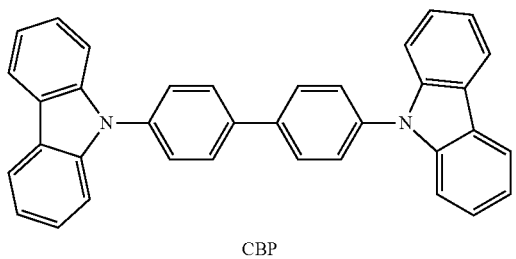

CBP

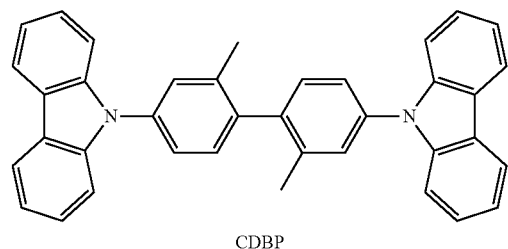

CDBP

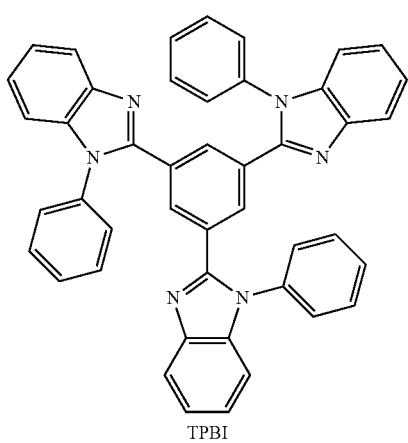

TPBI

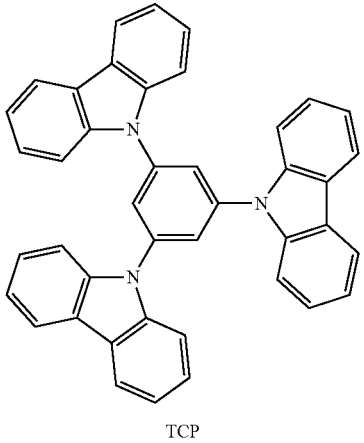

TCP

Alternatively, the host may further include a compound represented by Formula 301:

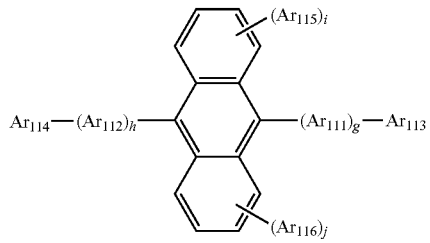

Formula 301

$Ar_{111}$ and $Ar_{112}$ in Formula 301 may be each independently selected from a phenylene group, a naphthylene group, a phenanthrenylene group, and a pyrenylene group; and a phenylene group, a naphthylene group, a phenanthrenylene group, a fluorenyl group, and a pyrenylene group, each substituted with at least one selected from a phenyl group, a naphthyl group, and an anthracenyl group.

$Ar_{113}$ to $Ar_{116}$ in Formula 301 may be each independently selected from a $C_1$-$C_{10}$ alkyl group, a phenyl group, a naphthyl group, a phenanthrenyl group, and a pyrenyl group; and a phenyl group, a naphthyl group, a phenanthrenyl group, a fluorenyl group, and a pyrenyl group, each substituted with at least one selected from a phenyl group, a naphthyl group, and an anthracenyl group.

g, h, i, and j in Formula 301 may each independently be an integer of 0 to 4, for example, 0, 1, or 2.

$Ar_{113}$ to $Ar_{116}$ in Formula 301 may be each independently selected from a $C_1$-$C_{10}$ alkyl group, substituted with at least one selected from a phenyl group, a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

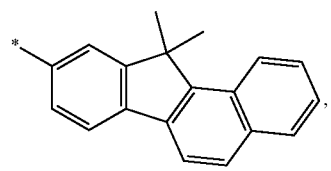 [SMILES: *c1ccc2c(c1)C(C)(C)c1c-2ccc2ccccc12]

but embodiments are not limited thereto.

In some embodiments, the host may include a compound represented by Formula 302 below:

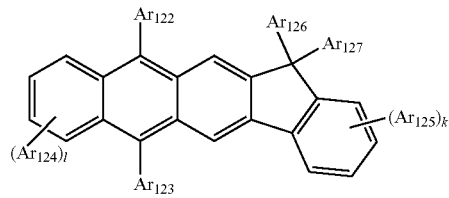

Formula 302

$Ar_{122}$ to $Ar_{125}$ in Formula 302 are the same as defined in connection with $Ar_{113}$ in Formula 301.

$Ar_{126}$ and $Ar_{127}$ in Formula 302 may each independently be a $C_1$-$C_{10}$ alkyl group (e.g., a methyl group, an ethyl group, or a propyl group).

k and l in Formula 302 may each independently be an integer of 0 to 4. For example, k and l may be 0, 1, or 2.

For example, the compound represented by Formula 201 and the compound represented by Formula 302 may include Compounds HT1 to HT42, but embodiments are not limited thereto:

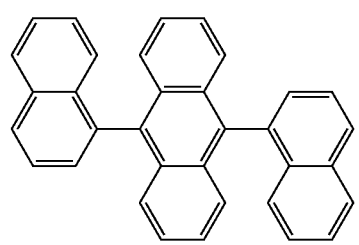

H1

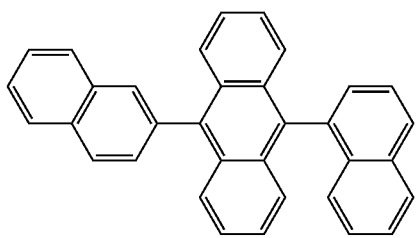

H2

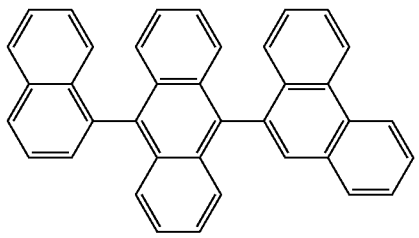

H3

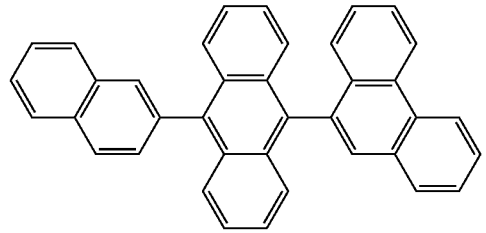

H4

-continued
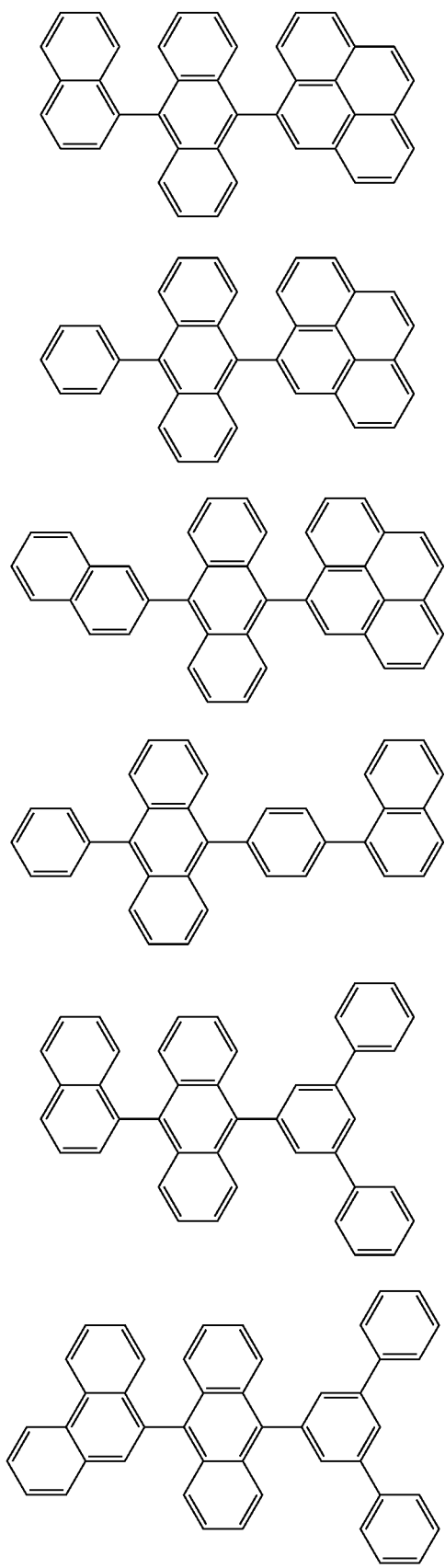
H5
H6
H7
H8
H9
H10
-continued
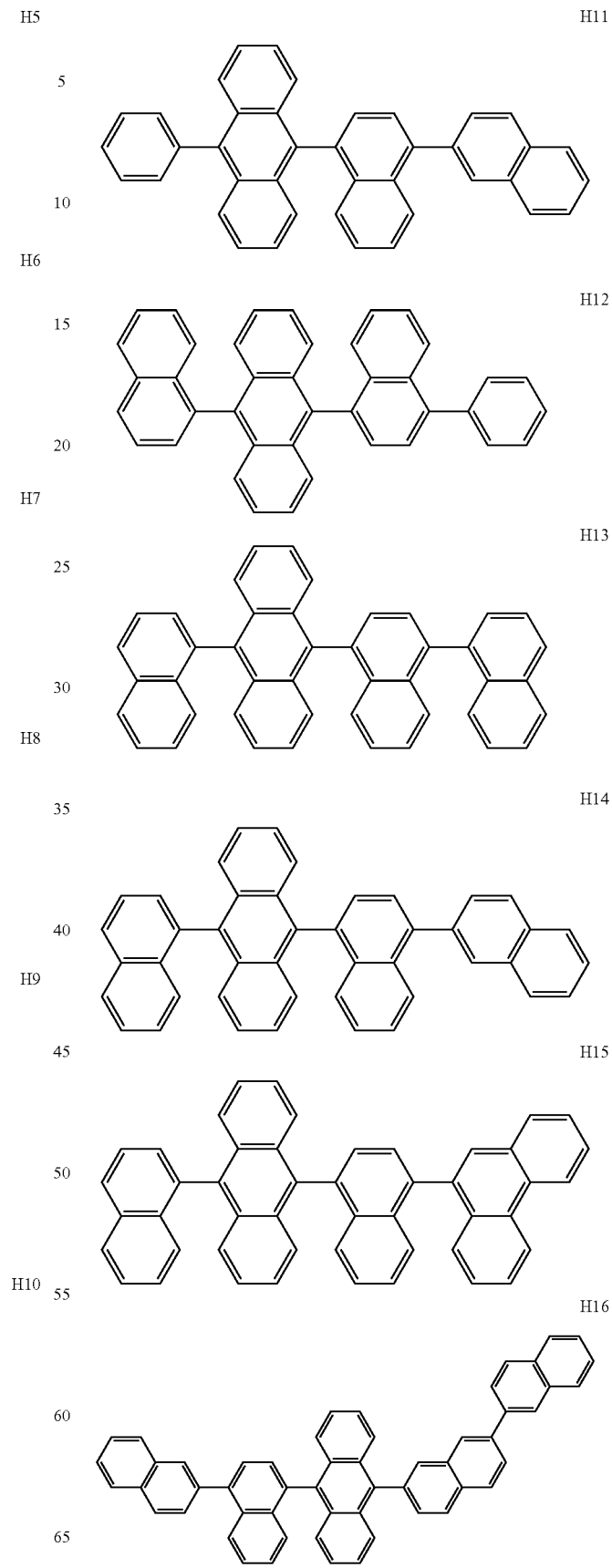
H11
H12
H13
H14
H15
H16

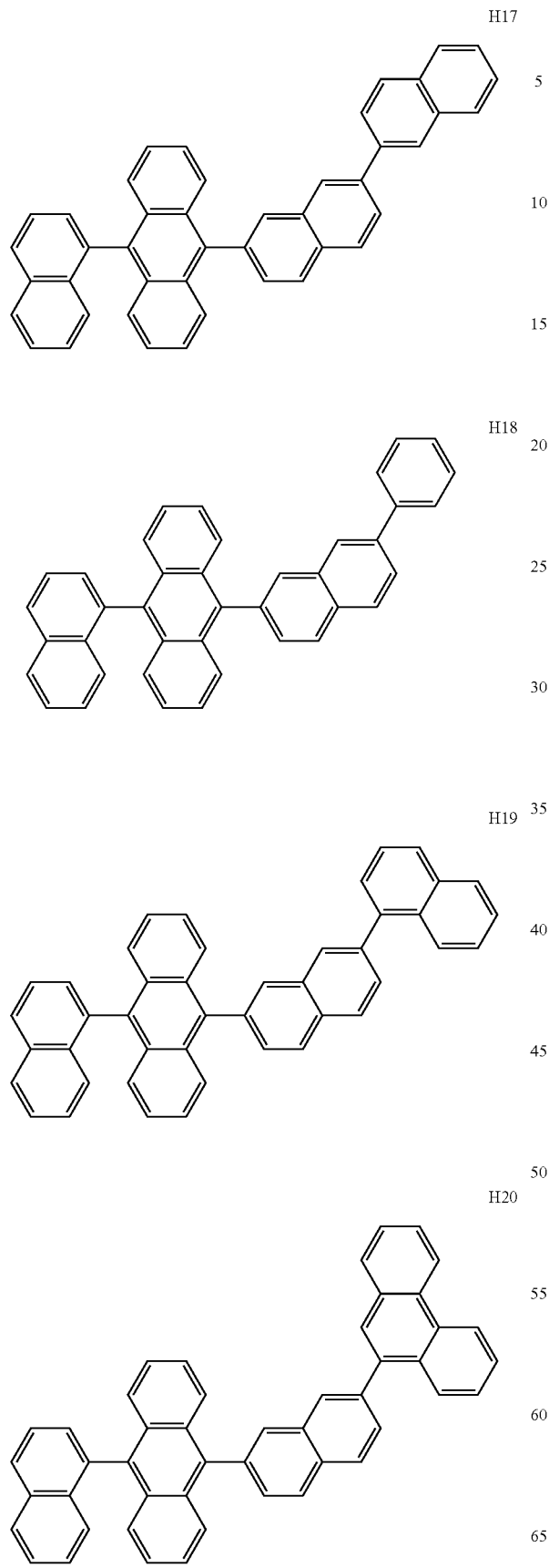
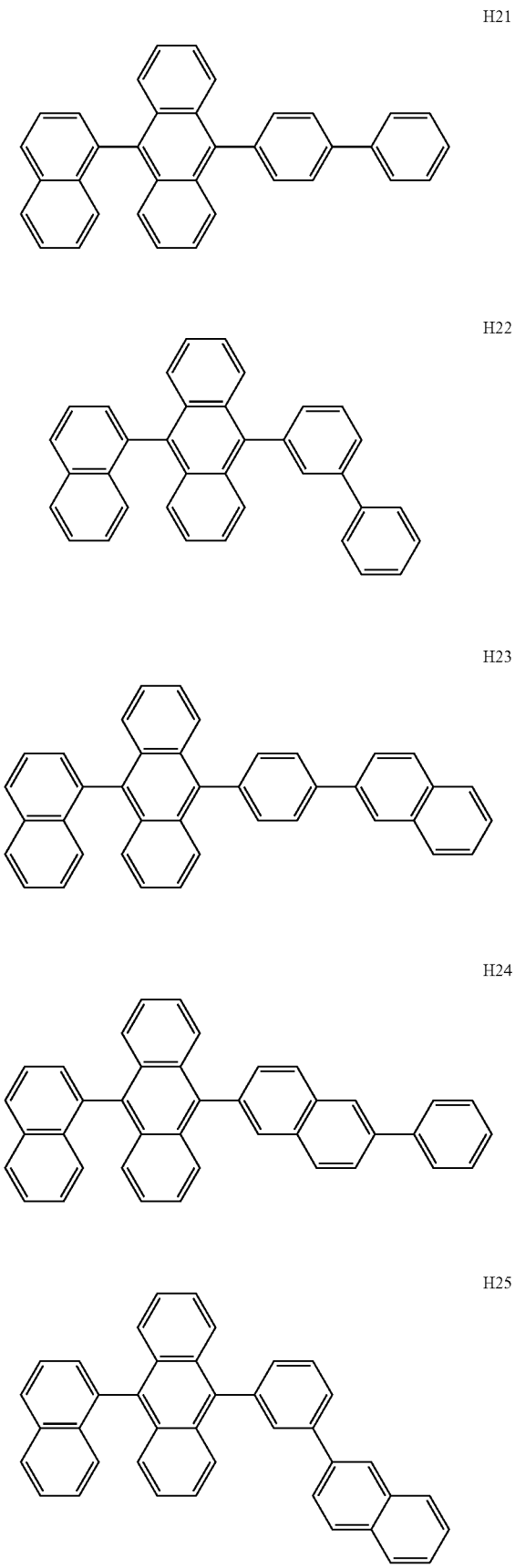

H26
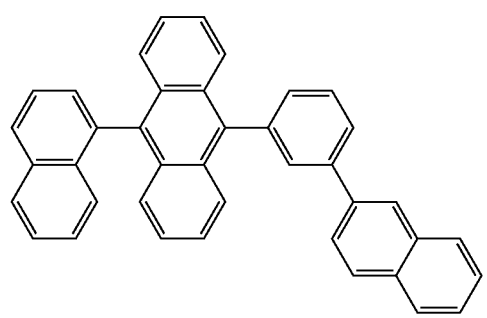
H27
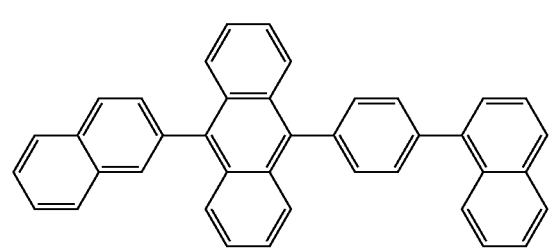
H28
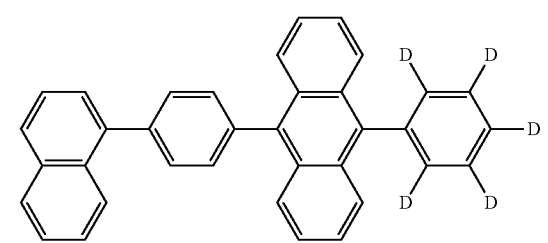
H29
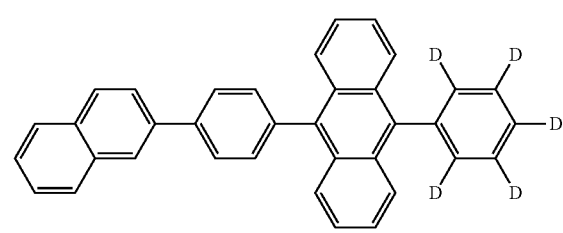
H30
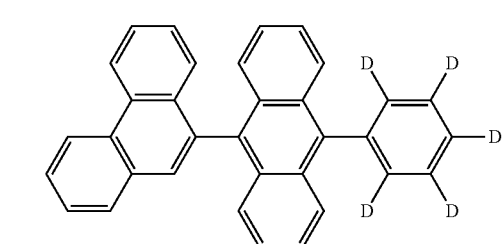
H31
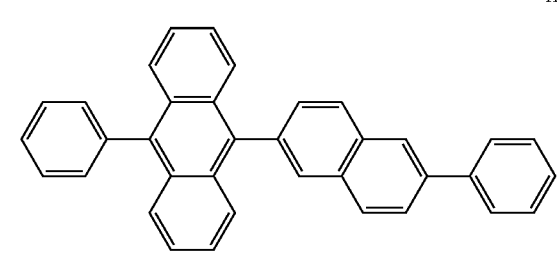
H32
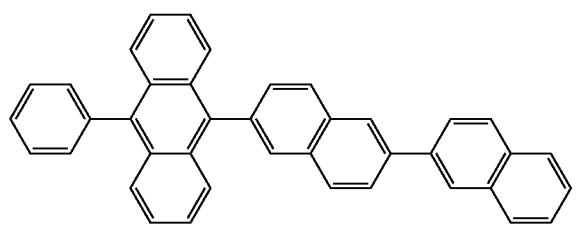
H33
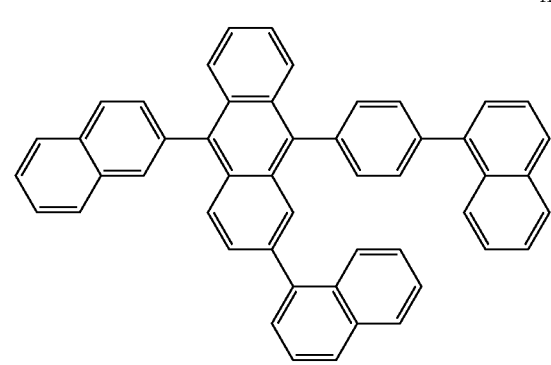
H34
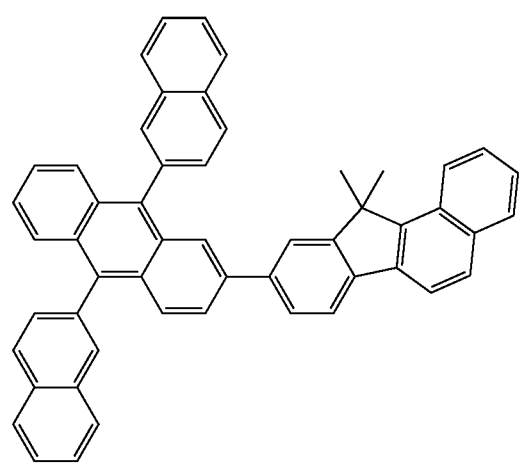
H35
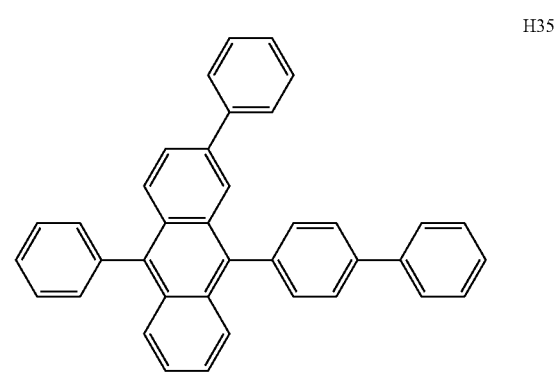

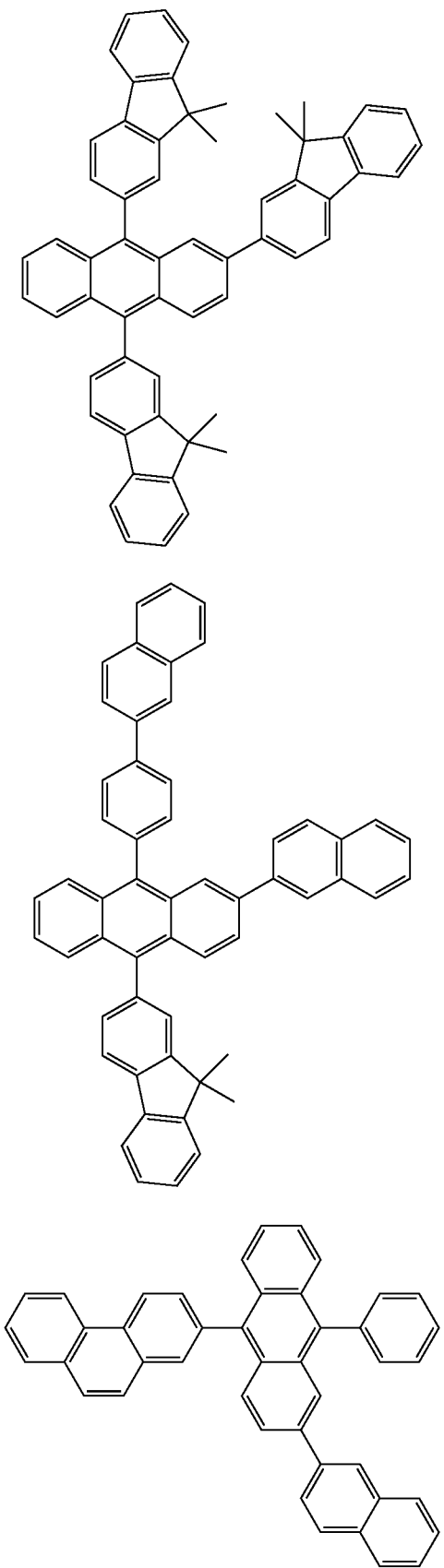
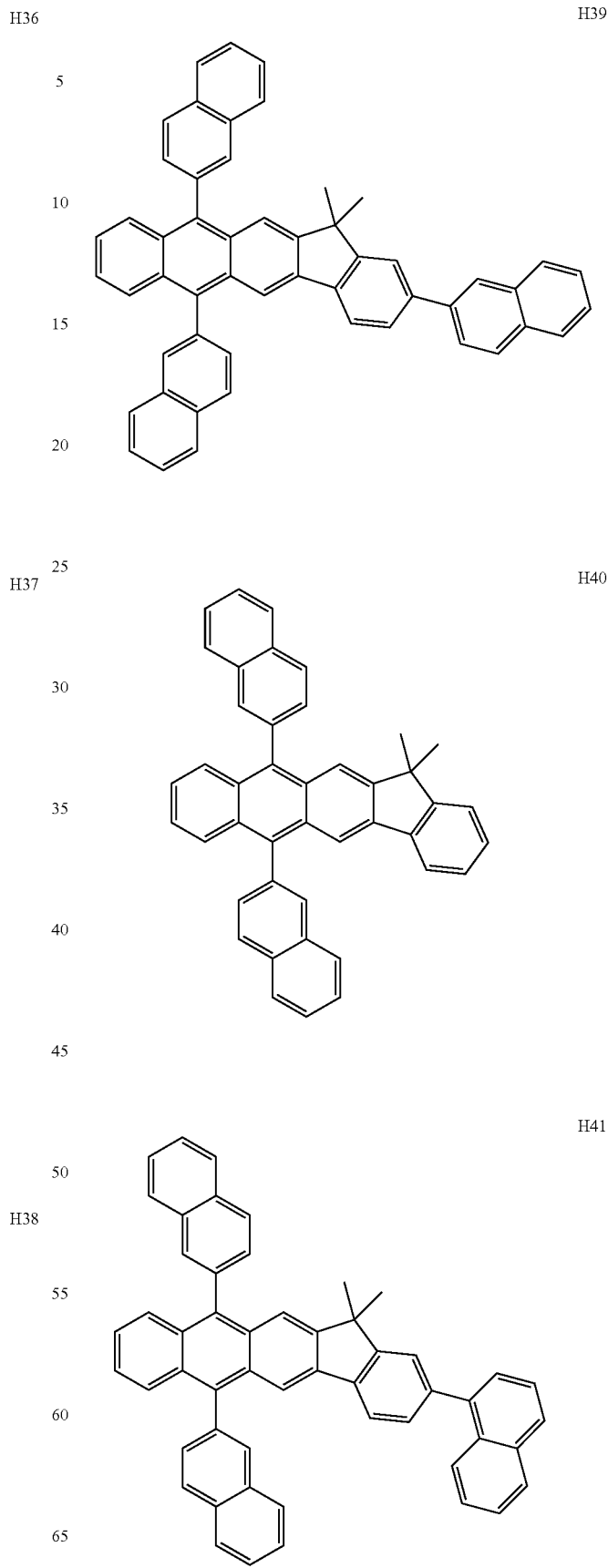

H42

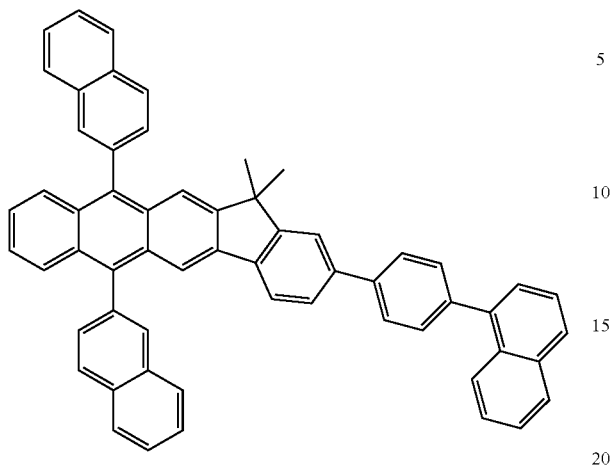

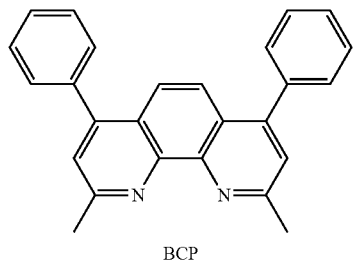

BCP

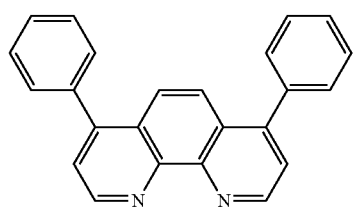

Bphen

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light. However, other various embodiments are also possible.

The emission layer may include the organometallic compound represented by Formula 1 as a dopant.

When the emission layer includes the host and the dopant, an amount of the dopant may be selected from about 0.01 part by weight to about 20 parts by weight based on about 100 parts by weight of the host, but the amount is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

For example, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes an hole blocking layer, the hole blocking layer may, for example, include at least one of BCP and Bphen, but is not limited thereto.

A thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may further include at least one selected from BCP, BPhen, Alq3, BAlq, TAZ, and NTAZ.

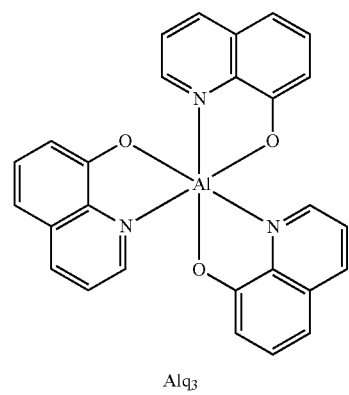

Alq₃

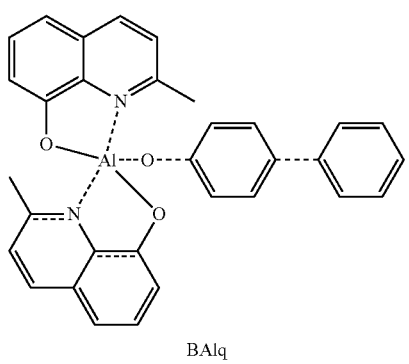

BAlq

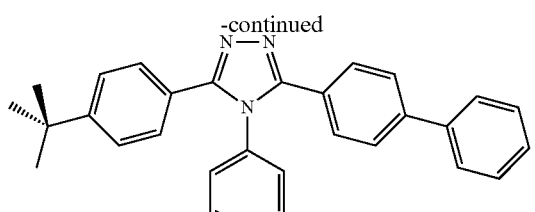

TAZ

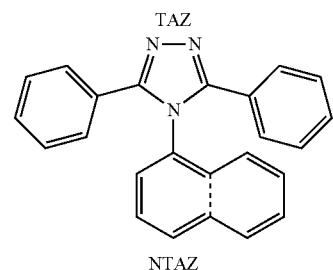

NTAZ

In some embodiments, the electron transport layer may include at least one selected from Compounds ET1 and ET2, but it is not limited thereto.

ET1

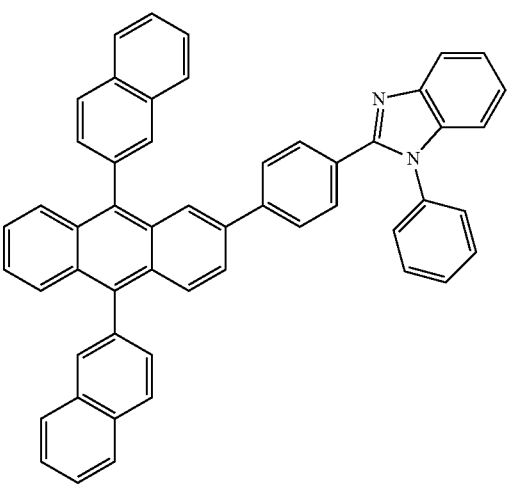

ET2

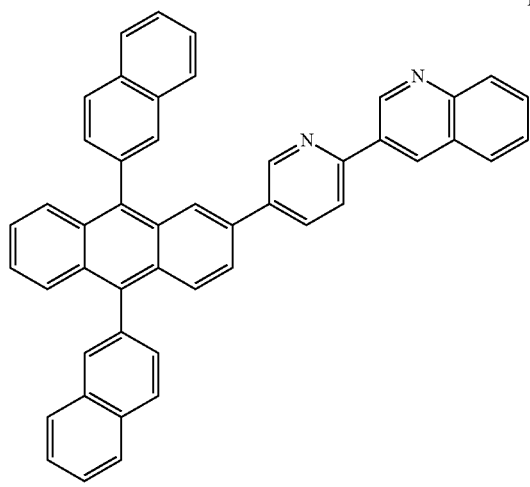

A thickness of the electron transport layer may be in a range of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

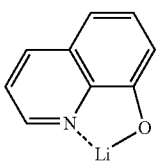

ET-D2

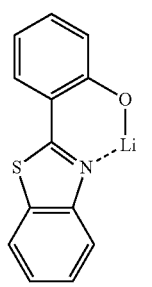

The electron transport region may include an electron injection layer (EIL) that facilitates electron injection from the second electrode 19.

The electron injection layer may include at least one selected from, LiF, NaCl, CsF, $Li_2O$, and BaO.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 are lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and such a variation may be possible.

Hereinbefore, the organic light-emitting device has been described with reference to FIG. 1, but embodiments are not limited thereto.

A $C_1$-$C_{60}$ alkyl group as used herein refers to a linear or branched saturated aliphatic hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group. A $C_1$-$C_{60}$ alkylene group as used herein refers to a divalent group having the same structure as a $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a group formed by including at least one carbon double bond in the middle or at the terminal of the $C_2$-$C_{60}$ alkyl group as defined above. Detailed examples thereof are an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a group formed by including at least one carbon triple bond in the middle or at the terminal of the $C_2$-$C_{60}$ alkyl group as defined above. Detailed examples thereof are an ethenyl group and a propenyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in its ring, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_2$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system including at least one hetero atom selected from N, O, P, and S as a ring-forming atom and 1 to 60 carbon atoms. A $C_1$-$C_{60}$ heteroarylene group as used herein refers to a divalent group having a carbocyclic aromatic system including at least one hetero atom selected from N, O, P, and S as a ring-forming atom and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates -$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring forming atoms, wherein the molecular structure as a whole is non-aromatic. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has a plurality of rings condensed with each other, has a hetero atom selected from N, O P, and S, other than carbon atoms (for example, the number of carbon atoms may be in a range of 1 to 60), as ring-forming atoms, wherein the molecular structure as a whole is non-aromatic. The monovalent non-aromatic condensed heteropolycyclic group includes a carbazolyl group. A divalent non-aromatic condensed heteropolycyclic group as used herein refers to a divalent group having the same structure as the monovalent non-aromatic condensed heteropolycyclic group.

The term "Ph" as used herein refers to a phenyl group, the term "t-Bu" as used herein refers to a tert-butyl group, and the term "Me" as used herein refers to a methyl group.

Hereinafter, an organic light-emitting device according to an embodiment will be described in detail with reference to Synthesis Examples and Examples, however, the present inventive concept is not limited thereto. The expression "B was used instead of A" used in describing Synthesis Examples means that an amount of B used was identical to an amount of A used based on molar equivalence.

EXAMPLE

Synthesis Example 1

Synthesis of Compound PD-1

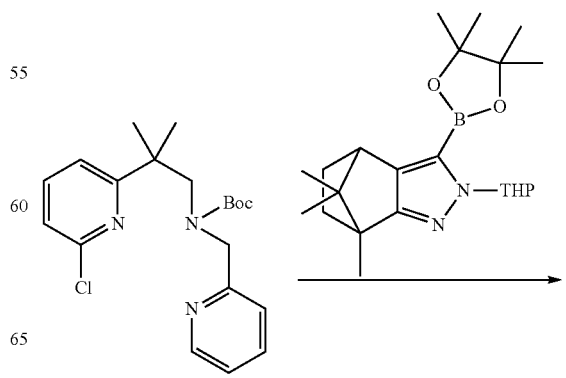

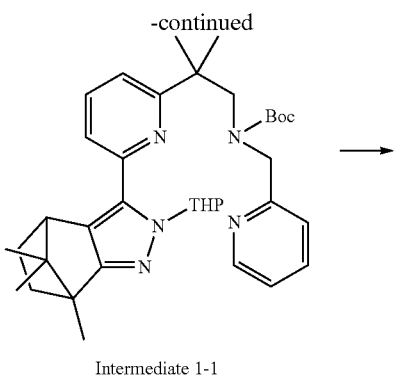

Intermediate 1-1

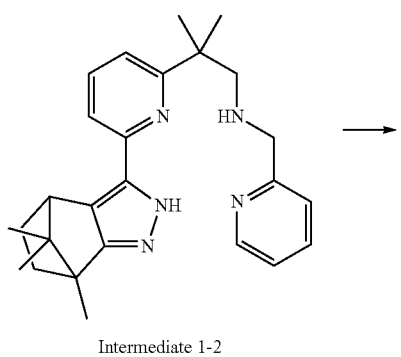

Intermediate 1-2

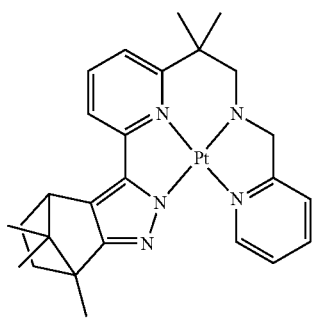

Compound PD-1

(1) Synthesis of Intermediate 1-1

10.0 grams (g) (26.6 millimoles (mmol)) of tert-butyl(2-(6-chloropyridine-2-yl)-2-methylpropyl)(pyridine-2-ylmethyl)carbamate and 12.7 g (31.9 mmol) of 7,8,8-trimethyl-2-(tetrahydro-2H-pyran-2-yl)-3-(4,4,5,5-tetramethyl-1,3,2-dioxaborolane-2-yl)-4,5,6,7-tetrahydro-2H-4,7-metanoindazole were placed into a flask and 100 milliliters (ml) of toluene was added thereto under nitrogen atmosphere. 1.50 g (1.30 mmol) of Pd(PPh$_3$)$_4$ and 11.0 g (79.8 mmol) of K$_2$CO$_3$ were sequentially added thereto and then the resulting mixture was stirred at 110° C. for 24 hours. When the reaction was complete, the resulting mixture was cooled to a room temperature and the toluene was removed by distillation under a reduced pressure. Then, the residue was diluted with 350 ml of ethyl acetate. The obtained organic layer was washed with 150 ml of saturated NaHCO$_3$ aqueous solution (two times) and 100 ml of saturated NaCl aqueous solution (two times), dried with MgSO$_4$, and filtered. Next, the organic layer was distilled under a reduced pressure. The residue was purified by column chromatography (ethyl acetate:hexane=1:1) to obtain 14.0 g (yield of 88%) of Intermediate 1-1.

C, 36; H, 49; N, 5; O, 3: M+H=600.84

$^1$H NMR (CDCl$_3$, 300 MHz) δ(ppm) 8.39(s, 1H), 7.65(t, 1H), 7.53(s, 1H), 7.40(t, 1H), 7.26-6.96(m, 2H), 6.59-6.33 (m, 1H), 4.31-3.63 (m, 8H), 2.49 (d, 1H), 2.44-2.41(m, 1H), 1.50-1.24 (m, 24H)

(2) Synthesis of Intermediate 1-2

14.0 g (23.3 mmol) of Intermediate 1-1 was diluted with 200 ml of dichloromethane and the resulting mixture was cooled to 0° C. 6.1 ml of hydrochloric acid was slowly added thereto and the resulting mixture was stirred for 4 hours while the reaction mixture was allowed to warm to a room temperature. When the reaction was complete, saturated NaHCO$_3$ aqueous solution was added until the resulting mixture became neutral (pH=7~8), then the organic layer was separated. The obtained organic layer was washed with 100 ml of saturated NaCl aqueous solution (two times), dried with MgSO$_4$, and filtered. Next, the organic layer was distilled under a reduced pressure to obtain 6.4 g (yield of 66%) of Intermediate 1-2.

C, 26; H, 33; N, 5: M+H=416.60

$^1$H NMR (CDCl$_3$, 300 MHz) δ(ppm) 8.64(s, 1H), 7.63-7.58(m, 2H), 7.34(t, 1H), 7.25(t, 2H), 7.22-7.14(m, 1H), 4.27(d, 2H), 3.81(d, 2H), 3.02(s, 1H), 2.13(t, 2H), 1.98(t, 2H), 1.39-1.34 (m, 9), 0.99(s, 3H), 0.75(s, 3H)

(3) Synthesis of Compound PD-1

3.0 g (7.2 mmol) of Intermediate 1-2 and 3.0 g (7.2 mmol) of K$_2$PtCl$_4$ were diluted with 50 ml of acetic acid, 0.2 g (0.7 mmol) of Bu$_4$NCl was added thereto, and the resulting mixture was stirred at 145° C. for 18 hours. When the reaction was complete, the resulting mixture was cooled to a room temperature, and diluted with 150 ml of dichloromethane. Saturated NaHCO$_3$ aqueous solution was further added until the mixture was neutralized (pH=7~8), and the organic layer was separated. The obtained organic layer was washed with 100 ml of saturated NaCl aqueous solution (two times), dried with MgSO$_4$, and filtered. Next, the organic layer was distilled under a reduced pressure. The residue was purified by column chromatography (dichloromethane:methanol=10:1) to obtain 800 mg (yield of 18%) Compound PD-1.

C, 26; H, 31 N, 5; Pt: M+H=609.72

$^1$H NMR (CDCl$_3$, 300 MHz) δ(ppm) 7.99(t, 1H), 7.82(t, 1H), 7.71(d, 1H), 7.48-7.32(m, 3H), 7.26 (s, 1H), 4.23(d, 2H), 3.79(d, 2H), 2.93(s, 1H), 2.01(t, 2H), 1.93(t, 2H), 1.41-1.33 (m, 9H), 1.01(s, 6H)

Synthesis Example 2

Synthesis of Compound PD-2

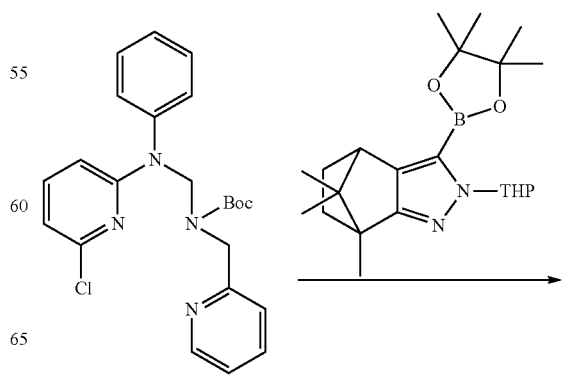

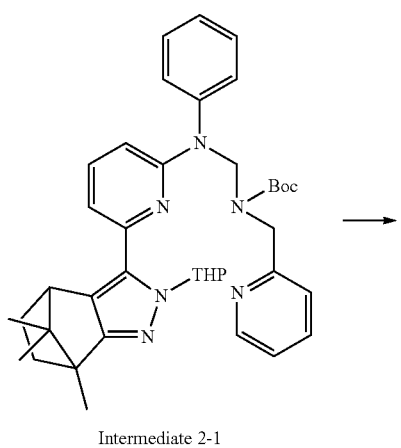

Intermediate 2-1

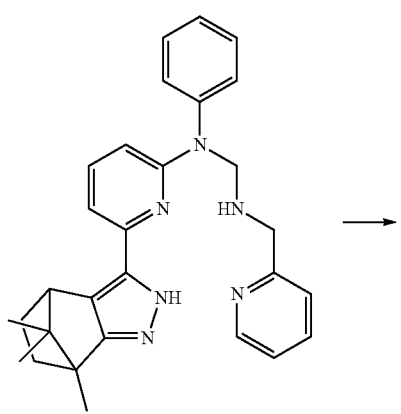

Intermediate 1-2

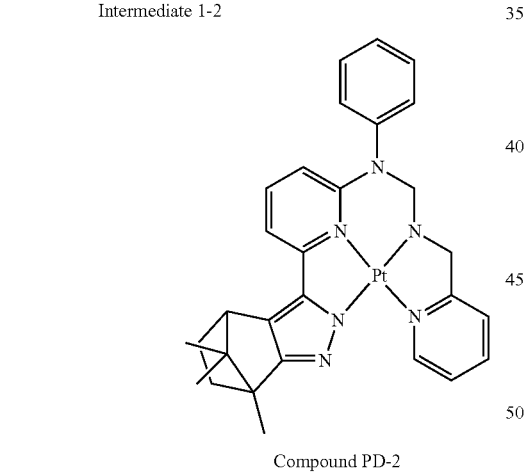

Compound PD-2

900 mg (yield of 19%) of Compound PD-2 was synthesized in the same manner as in Synthesis Example 1, except that, in the synthesizing Intermediate 1-1, tert-butyl(((6-chloropyridine-2-yl)(phenyl)amino)methyl)(pyridine-2-ylmethyl)carbamate was used instead of tert-butyl(2-(6-chloropyridine-2-yl)-2-methylpropyl)(pyridine-2-ylmethyl)carbamate.

C, 29; H, 30; N, 6Pt: M+H=658.30

$^1$H NMR (CDCl$_3$, 300 MHz) δ(ppm) 8.64(d, 1H), 7.72(t, 1H), 7.49-7.23(m, 8H), 6.77-6.61(m, 2H), 4.32(d, 2H), 4.13 (d, 2H), 2.77(m, 1H), 1.99(t, 2H), 1.80 (t, 2H), 1.40 (s, 3H), 0.98(s, 6H)

Synthesis Example 3

Synthesis of Compound PD-4

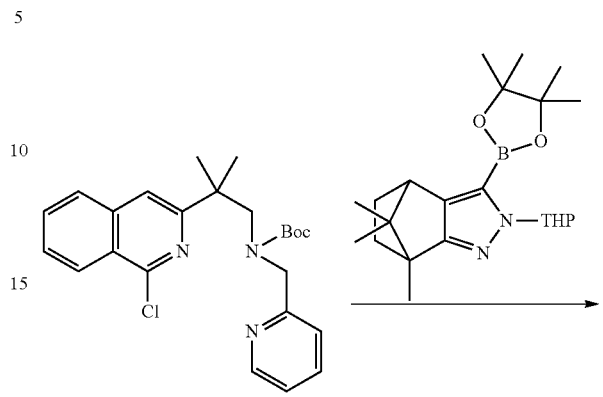

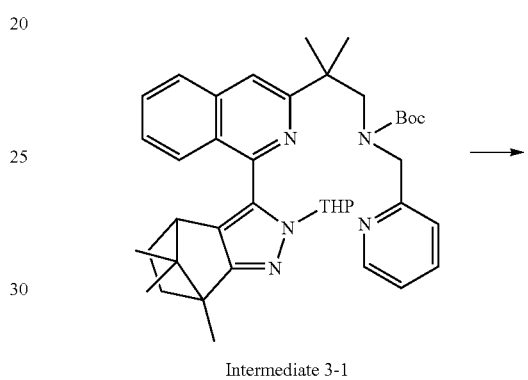

Intermediate 3-1

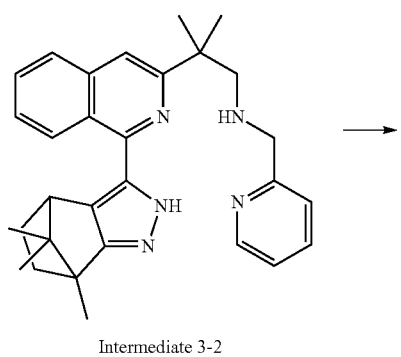

Intermediate 3-2

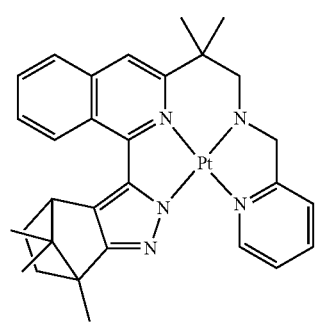

Compound PD-4

900 mg (yield of 19%) of Compound PD-4 was synthesized in the same manner as in Synthesis Example 1, except that, in the synthesizing Intermediate 1-1, tert-butyl(2-(1-chloroisoquinoline-3-yl)-2-methylpropyl)(pyridine-2-ylmethyl)carbamate was used instead of tert-butyl(2-(6-chloropyridine-2-yl)-2-methylpropyl)(pyridine-2-ylmethyl)carbamate.

C, 30; H, 33; N, 5; Pt: M+H=659.70

¹H NMR (CDCl₃, 300 MHz) δ(ppm) 8.72 (d, 1H), 7.85-7.69(m, 3H), 7.48-7.32(m, 4H), 7.26 (t, 1H), 4.10(d, 2H), 3.83(d, 2H), 3.10(s, 1H), 2.11(t, 2H), 1.91(t, 2H), 1.40-1.39 (m, 9H), 1.01(s, 6H)

Synthesis Example 4

Synthesis of Compound PD-5

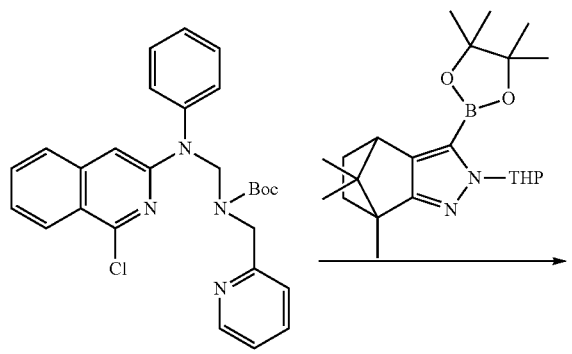

Intermediate 4-1

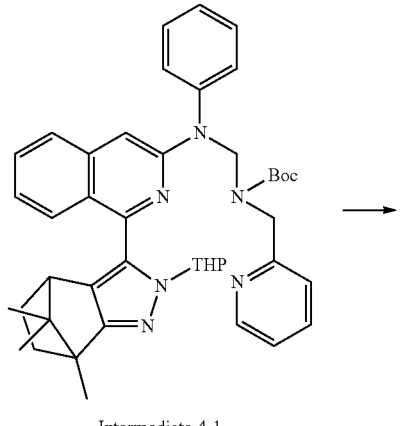

Intermediate 4-2

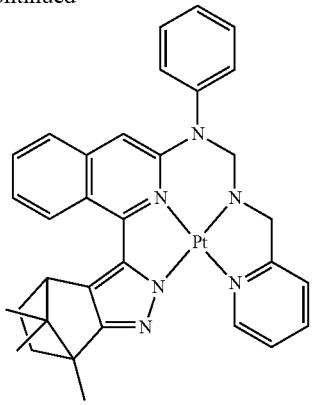

Compound PD-5

1.1 g (yield of 22%) Compound PD-5 was synthesized in the same manner as in Synthesis Example 1, except that, in the synthesizing Intermediate 1-1, tert-butyl(((1-chloroisoquinoline-3-yl)(phenyl)amino)methyl)(pyridine-2-ylmethyl)carbamate was used instead of tert-butyl (2-(6-chloropyridine-2-yl)-2-methylpropyl)(pyridine-2-ylmethyl)carbamate.

C, 33; H, 32; N, 6; Pt: M+H=708.71

1H NMR (CDCl₃, 300 MHz) δ(ppm) 8.44(d, 1H), 7.80-7.69(m, 4H), 7.55-7.21(m, 7H), 6.77(t, 1H), 6.50(s, 1H), 4.33(d, 2H), 4.10 (d, 2H), 2.68(m, 1H), 2.01(t, 2H), 1.80 (t, 2H), 1.39 (s, 3H), 1.00(s, 6H)

Synthesis Example 5

Synthesis of Compound PD-55

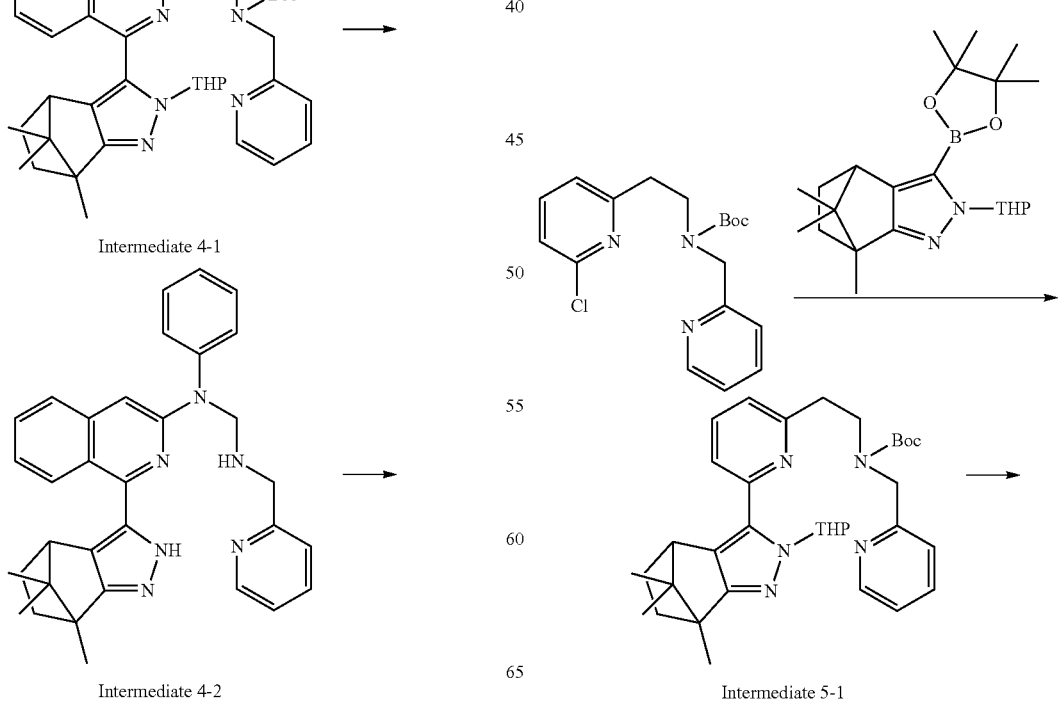

Intermediate 5-1

Intermediate 5-2

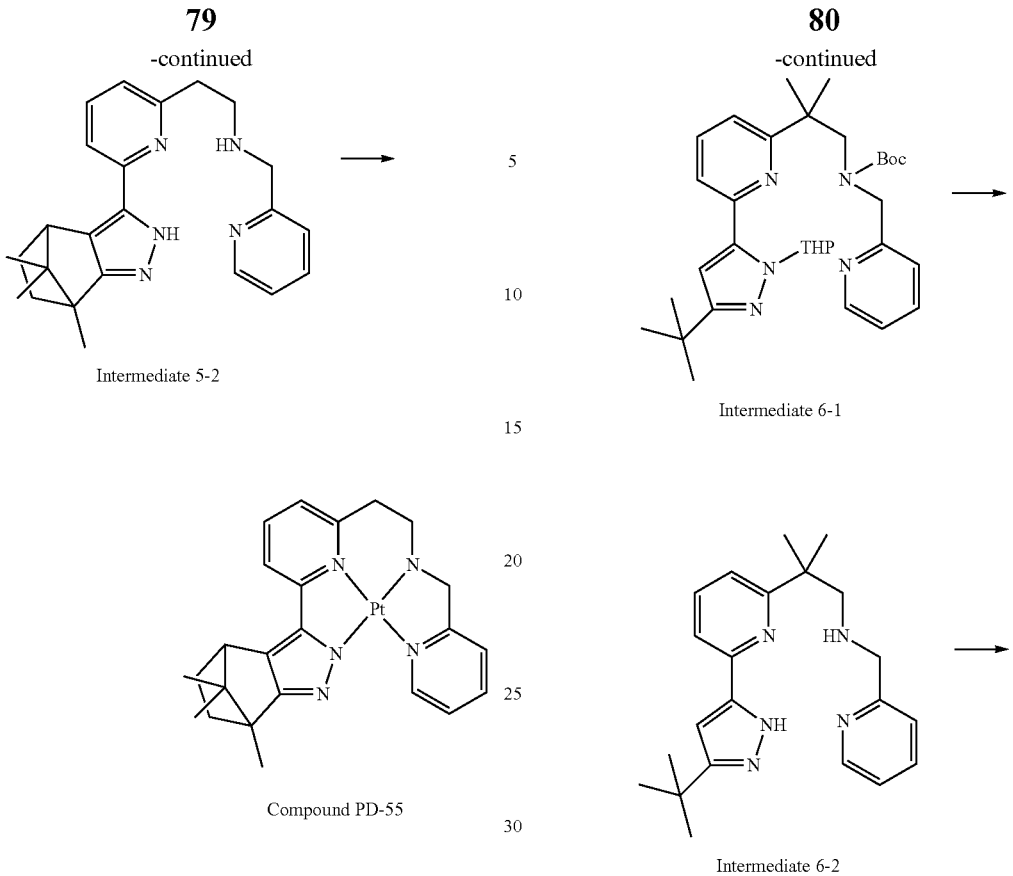

Intermediate 6-1

Intermediate 6-2

Compound PD-55

Compound PD-56

1.1 g (yield of 26%) Compound PD-55 was synthesized in the same manner as in Synthesis Example 1, except that, in the synthesizing Intermediate 1-1, tert-butyl(2-(6-chloro-pyridine-2-yl)ethyl)(pyridine-2-ylmethyl)carbamate was used instead of tert-butyl(2-(6-chloropyridine-2-yl)-2-methylpropyl)(pyridine-2-ylmethyl)carbamate.

C, 24; H, 27; N, 5; Pt: M+H=581.20

1H NMR (CDCl$_3$, 300 MHz) δ(ppm) 8.60(d, 1H), 7.88(t, 1H), 7.73-7.64(m, 3H), 7.31 (t, 1H), 7.26 (q, 1H), 4.14(d, 2H), 3.10-2.77(m, 5H), 2.01(t, 2H), 1.93(t, 2H), 1.45 (s, 3H), 1.00(s, 6H)

Synthesis Example 6

Synthesis of Compound PD-56

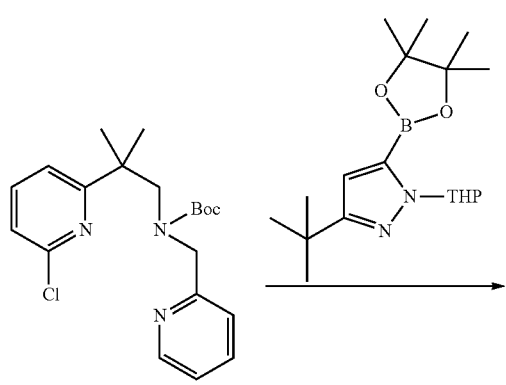

800 mg (yield of 20%) Compound PD-56 was synthesized in the same manner as in Synthesis Example 1, except that, in the synthesizing Intermediate 1-1, 3-(tert-butyl)-1-(tetrahydro-2H-pyran-2-yl)-5-(4,4,5,5-tetramethyl-1,3,2-dioxaborolane-2-yl)-1H-pyrazole was used instead of 7,8,8-trimethyl-2-(tetrahydro-2H-pyran-2-yl)-3-(4,4,5,5-tetramethyl-1,3,2-dioxaborolane-2-yl)-4,5,6,7-tetrahydro-2H-4,7-metanoindazole.

C, 22; H, 27; N, 5; Pt: M+H=557.38

1H NMR (CDCl$_3$, 300 MHz) δ(ppm) 8.59(d, 1H), 7.66-7.23(m, 6H), 6.01(s, 1H), 4.32(d, 2H), 2.77(m, 2H), 1.42 (s, 6H), 1.30(s, 9H)

81

Synthesis Example 7

Synthesis of Compound PD-57

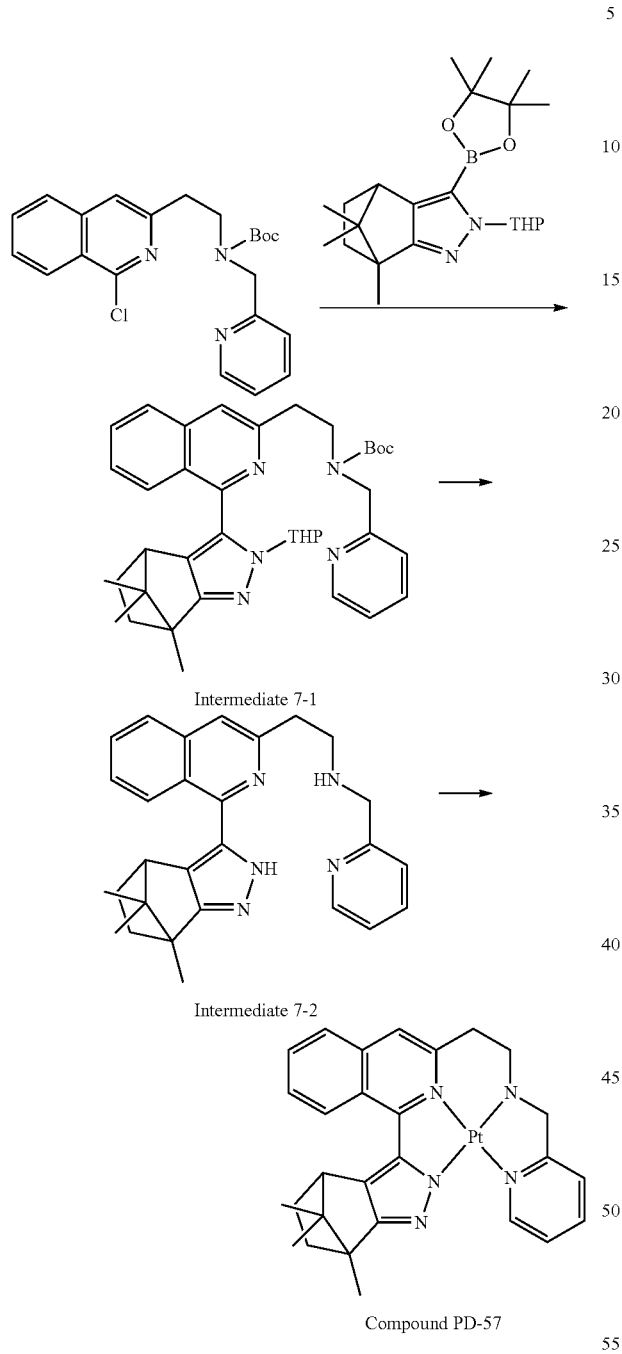

Intermediate 7-1

Intermediate 7-2

Compound PD-57

1.0 g (yield of 22%) Compound PD-57 was synthesized in the same manner as in Synthesis Example 1, except that, in the synthesizing Intermediate 1-1, tert-butyl(2-(1-chloroisoquinoline-3-yl)ethyl)(pyridine-2-ylmethyl)carbamate was used instead of tert-butyl(2-(6-chloropyridine-2-yl)-2-methylpropyl)(pyridine-2-ylmethyl)carbamate.

C, 28; H, 29; N, 5; Pt: M+H=631.63

1H NMR (CDCl$_3$, 300 MHz) δ(ppm) 8.61(d, 1H), 7.93(d, 1H), 7.88(t, 1H), 7.65-7.54(m, 4H), 7.31-7.26 (m, 2H), 4.10(d, 2H), 3.12-2.71(m, 5H), 1.99(t, 2H), 1.93(t, 2H), 1.41 (s, 3H), 1.05(s, 6H)

82

Synthesis Example 8

Synthesis of Compound PD-58

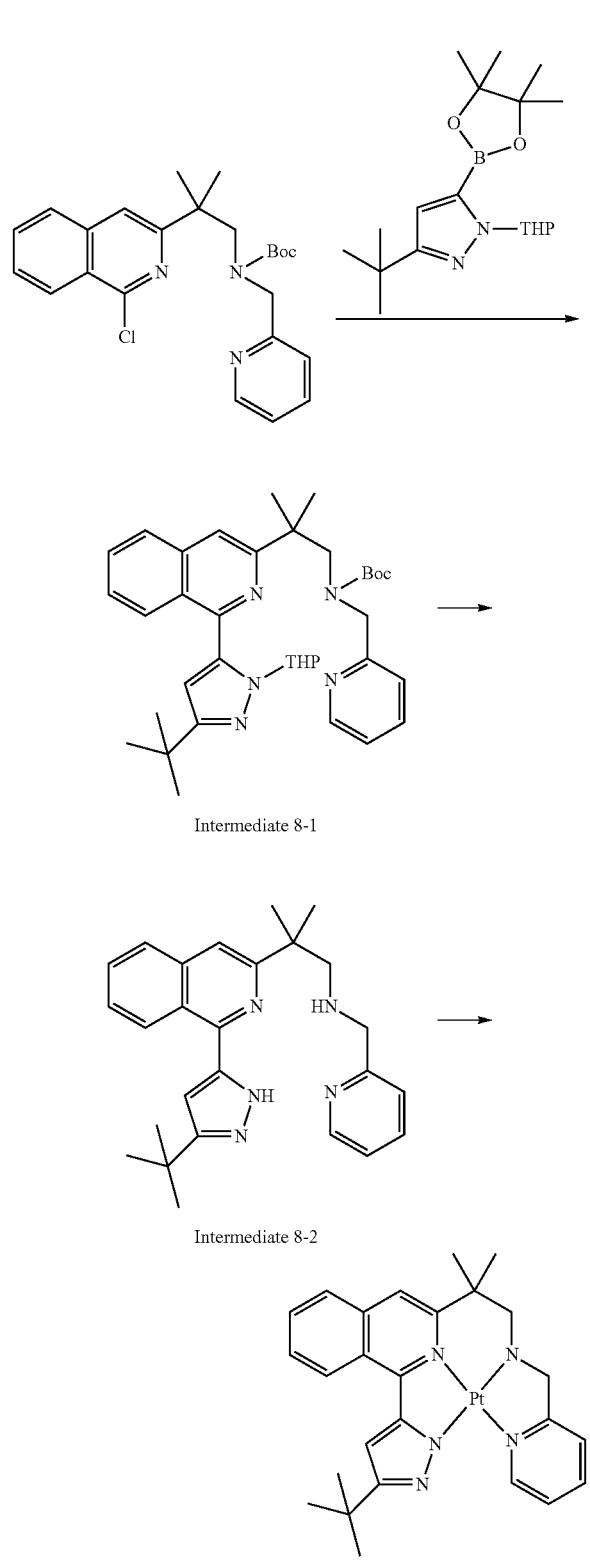

Intermediate 8-1

Intermediate 8-2

Compound PD-58

700 mg (yield of 16%) Compound PD-58 was synthesized in the same manner as in Synthesis Example 1, except that, in the synthesizing Intermediate 1-1, tert-butyl(2-(1-chloroisoquinoline-3-yl)-2-methylpropyl)(pyridine-2-ylmethyl)carbamate was used instead of tert-butyl (2-(6-chloropyridine-2-yl)-2-methylpropyl)(pyridine-2-ylmethyl)carbamate, and 3-(tert-butyl)-1-(tetrahydro-2H-pyran-2-yl)-5-(4,4,5,5-tetramethyl-1,3,2-dioxaborolane-2-yl)-1H-pyrazole was used instead of 7,8,8-trimethyl-2-(tetrahydro-2H-pyran-2-yl)-3-(4,4,5,5-tetramethyl-1,3,2-dioxaborolane-2-yl)-4,5,6,7-tetrahydro-2H-4,7-metano-indazole C, 26; H, 29; N, 5; Pt: M+H=607.66

1H NMR (CDCl$_3$, 300 MHz) δ(ppm) 8.66(d, 1H), 7.93(d, 1H), 7.73-7.17(m, 7H), 6.02(s, 1H), 4.28(d, 2H), 2.75(m, 2H), 1.40 (s, 6H), 1.29(s, 9H).

Synthesis Example 9

Synthesis of Compound PD-31

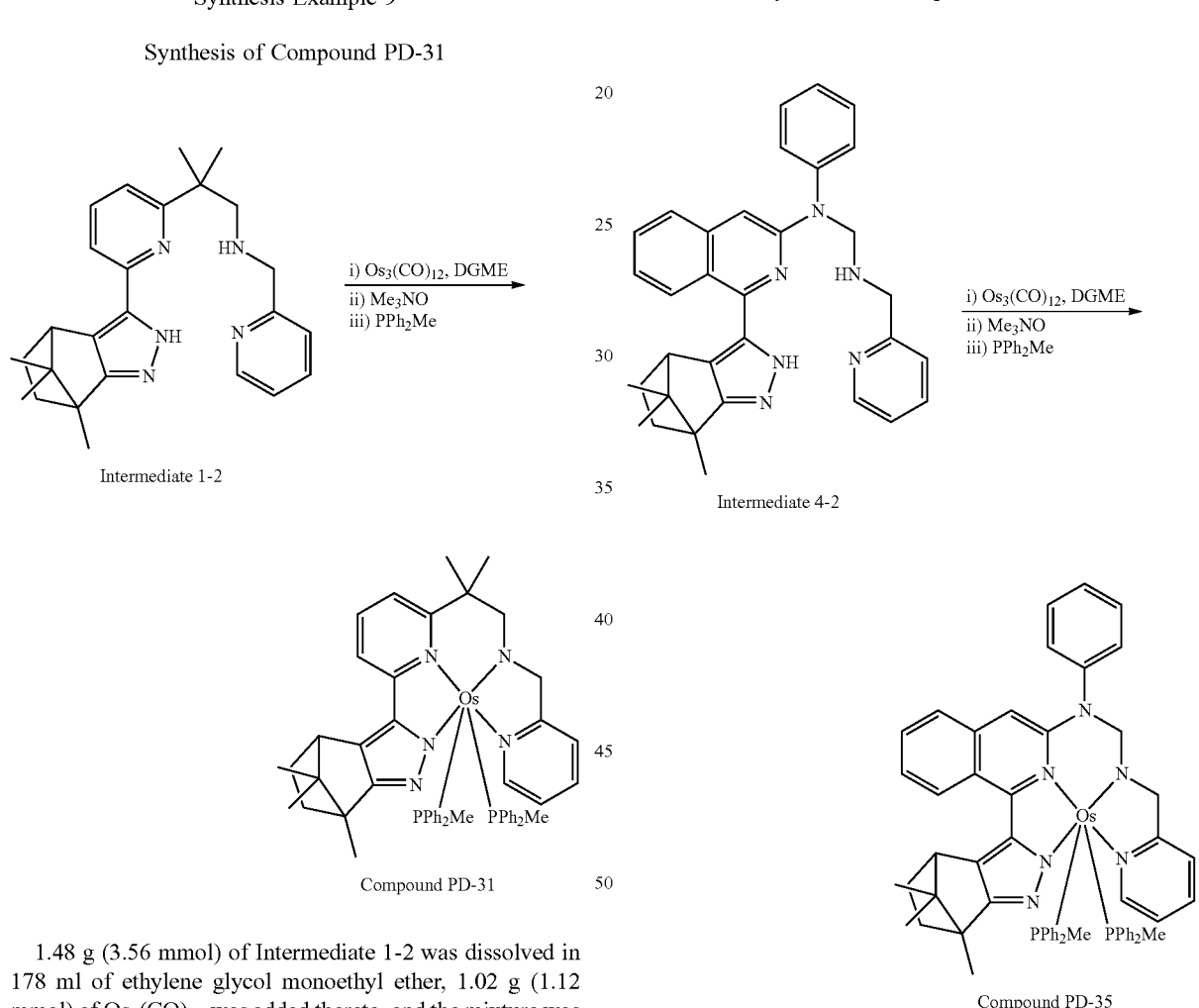

Intermediate 1-2

Compound PD-31

1.48 g (3.56 mmol) of Intermediate 1-2 was dissolved in 178 ml of ethylene glycol monoethyl ether, 1.02 g (1.12 mmol) of Os$_3$(CO)$_{12}$ was added thereto, and the mixture was heated at 210° C. for 4 days. When the reaction was complete, the mixture was cooled to a room temperature, 0.5 g (6.74 mmol) of trimethylamine-N-oxide was added thereto, and the resulting mixture was stirred for an hour. Next, 1.39 g (7.45 mmol) of methyldiphenylphosphine was added thereto, and the resulting mixture was heated at 190° C. for 14 hours. When the reaction was complete, the mixture was cooled to a room temperature, diluted with 250 ml of distilled water, and extracted with 350 ml of ethyl acetate. The extracted organic layer was dried with magnesium sulfate and distilled under a reduced pressure, thereby obtaining a reaction mixture residue. The obtained reaction mixture residue was separated and purified by column chromatography to 420 mg (0.42 mmol, yield of 34%) synthesize PD-31. The obtained compound was confirmed by LCMS and $^1$H NMR.

C, 52; H, 57; N, 5; OsP, 2: M+H=1006.33

1H NMR (CDCl$_3$, 300 MHz) δ(ppm) 8.64(d, 1H), 7.88-7.31(m, 25H), 7.16(d, 1H), 4.14(d, 2H), 3.01(d, 2H), 2.80(t, 1H), 1.96(t, 2H), 1.80 (t, 2H), 1.39-1.30 (m, 9H), 1.00(s, 6H), 0.95 (s, 6H)

Synthesis Example 10

Synthesis of Compound PD-35

Intermediate 4-2

Compound PD-35

441 mg (yield of 32%) of Compound PD-35 was synthesized in the same manner as in Synthesis Example 9, except that Intermediate 4-2 was used instead of Intermediate 1-2. The obtained compound was confirmed by LCMS and 1H NMR.

C, 59; H, 58; N, 6; OsP, 2: M+H=1105.42

1H NMR (CDCl$_3$, 300 MHz) δ(ppm) 8.73(d, 1H), 7.93 (d, 1H), 7.73(t, 1H), 7.72-7.28(m, 30H), 7.09(d, 1H), 4.32(d, 2H), 4.18(d, 2H), 2.64(t, 1H), 2.01(t, 2H), 1.94 (t, 2H), 1.44 (s, 3H), 1.10(s, 6H), 0.89 (s, 6H)

Synthesis Example 11

Synthesis of Compound PD-62

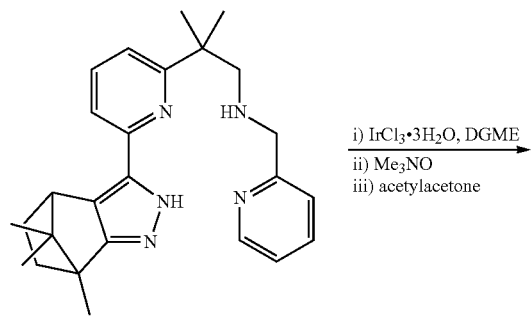

Intermediate 1-2 i) IrCl$_3$•3H$_2$O, DGME
ii) Me$_3$NO
iii) acetylacetone

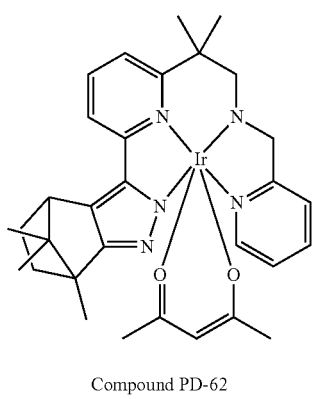

Compound PD-62

720 mg (yield of 28%) of Compound PD-62 was synthesized in the same manner as in Synthesis Example 9, except that 1.30 g (3.69 mmol) of IrCl$_3$.3H$_2$O was used instead of Os$_3$(CO)$_{12}$, and acetylacetone was used instead of methyldiphenylphosphine. The obtained compound was confiremd by LCMS and 1H NMR.

C, 31; H, 38; IrN, 5; O, 2: M+H=706.30

1H NMR (CDCl$_3$, 300 MHz) δ(ppm) 8.80(d, 1H), 7.76-7.42(m, 5H), 7.00(d, 1H), 4.10(d, 2H), 3.00(t, 1H), 2.89(d, 2H), 2.00(t, 2H), 1.93 (t, 2H), 1.36-1.32 (m, 10H), 1.18(d, 6H), 0.95 (s, 6H)

Synthesis Example 12

Synthesis of Compound PD-63

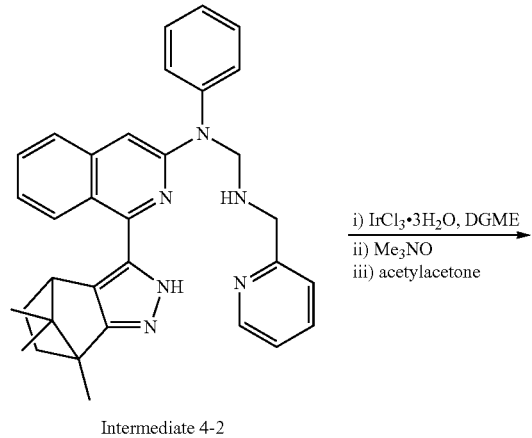

Intermediate 4-2 i) IrCl$_3$•3H$_2$O, DGME
ii) Me$_3$NO
iii) acetylacetone

-continued

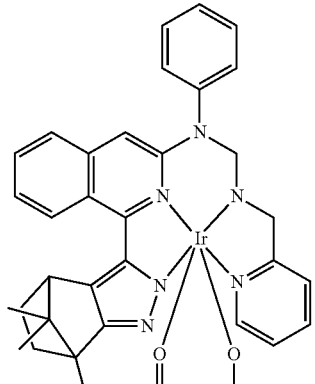

Compound PD-63

790 mg (yield of 27%) of Compound PD-63 was synthesized in the same manner as in Synthesis Example 11, except that Intermediate 4-2 was used instead of Intermediate 1-2. The obtained compound was confiremd by LCMS and 1H NMR.

C, 38; H, 39; IrN, 6; O, 2: M+H=805.29

1H NMR (CDCl$_3$, 300 MHz) δ(ppm) 8.73(d, 1H), 7.80-7.73(m, 2H), 7.50-7.19(m, 9H), 6.77(t, 1H), 6.50(s, 1H), 4.32(s, 2H), 4.14(s, 2H), 2.77(dd, 1H), 1.99(t, 2H), 1.90 (t, 2H), 1.72-1.45 (m, 4H), 1.15(d, 6H), 0.92 (s, 6H)

Example G1

A glass substrate with an indium tin oxide (ITO)/Ag/ITO (70 Å/1,000 Å/70 Å) electrode (first electrode, anode) was sonicated with distilled water, and then further sonicated with solvent such as isopropyl alcohol, acetone, and methanol and dried to be placed in a plasma cleaner. Next, the glass substrate was cleaned for 5 minutes by using an oxygen plasma and mounted on a vacuum deposition apparatus.

Compound 2-TNATA was vacuum deposited on the ITO electrode of the glass substrate to form a hole injection layer having a thickness of 600 Å, and NPB was deposited on the hole injection layer to form a hole transport layer having a thickness of 1,000 Å. As a result, a hole transport region was formed.

CBP (host) and Compound 10 (dopant) were co-deposited on the hole transport region in a weight ratio of 91:1 to form an emission layer having a thickness of 250 Å.

BCP was deposited on the emission layer to form a hole blocking layer having a thickness of 50 Å. Then, Alq3 was deposited on the hole blocking layer to form an electron transport layer having a thickness of 350 Å. Subsequently, LiF was deposited on the electron transport layer to form an electron injection layer having a thickness of 10 Å. An MgAg (in a weight ratio of 90:10) second electrode (cathode) having a thickness of 120 Å was formed on the electron injection layer to manufacture an organic light-emitting device.

TABLE 2

|  | dopant |
| --- | --- |
| Example G1 | Compound PD-1 |
| Example G2 | Compound PD-55 |
| Example G3 | Compound PD-2 |
| Example G4 | Compound PD-56 |
| Example G5 | Compound PD-62 |
| Comparative Example G1 | Ir(PPy)₃ |
| Comparative Example G2 | Compound A |
| Comparative Example G3 | Compound B |

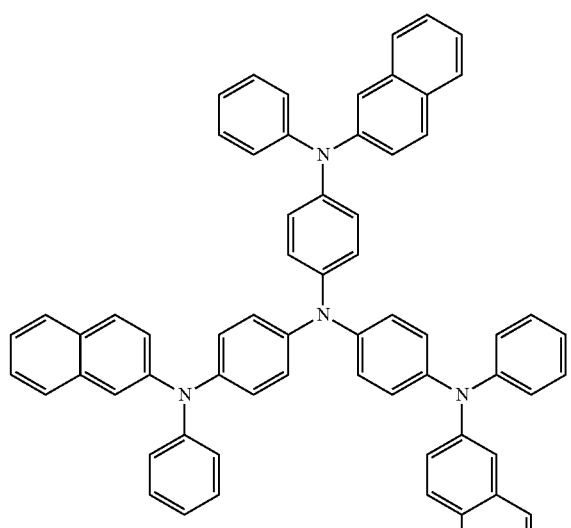

2-TNATA

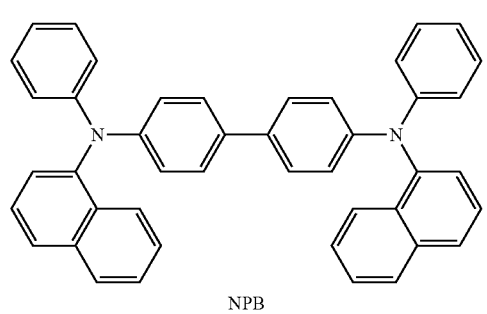

NPB

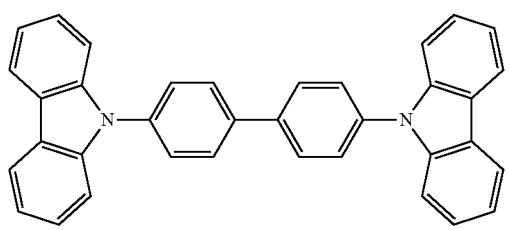

CBP

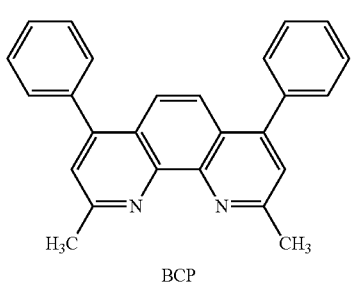

BCP

Examples G2 to G4 and Comparative Examples G1 to G3

Organic light-emitting devices were manufactured in the same manner as in Example G1, except that, as a dopant, compounds shown in Table 2 were respectively used instead of Compound 10:

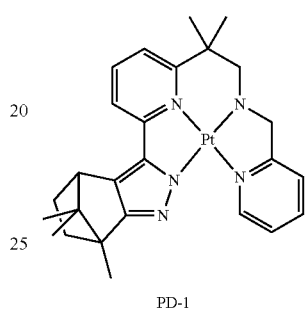

PD-1

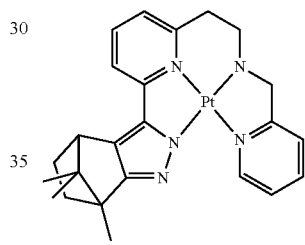

PD-55

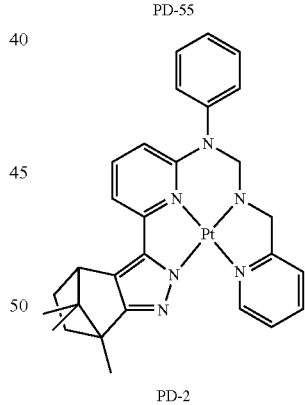

PD-2

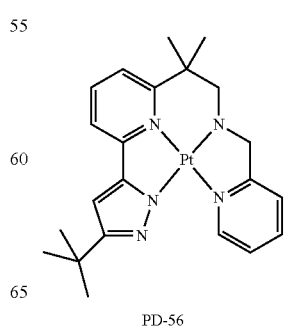

PD-56

TABLE 2-continued dopant

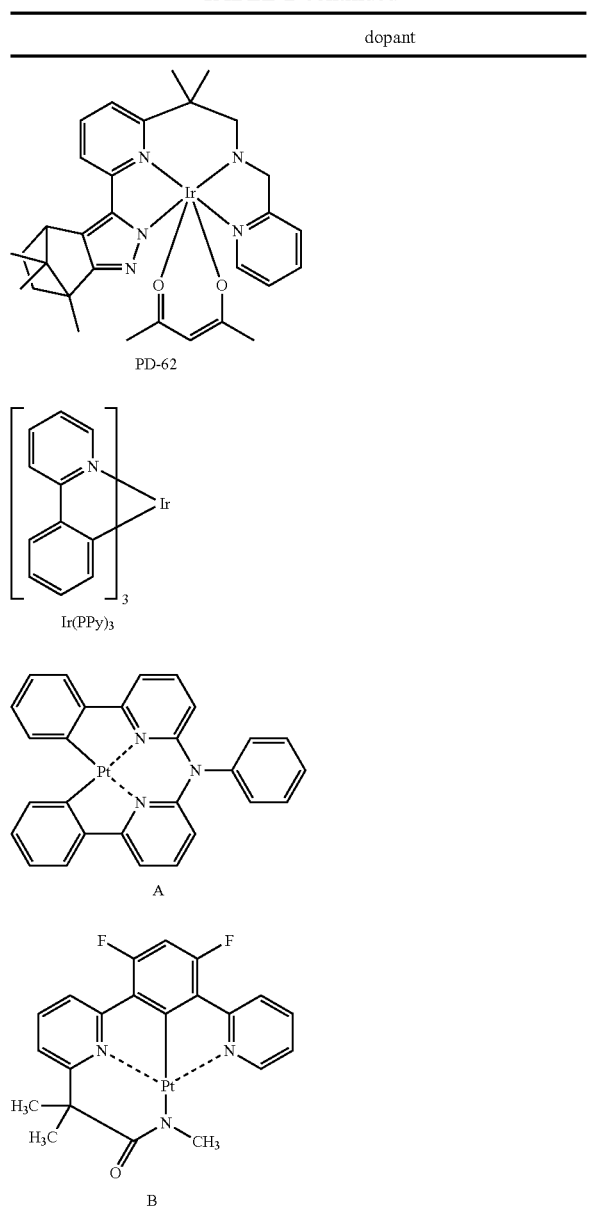

Example R1

A glass substrate with an ITO/Ag/ITO (70 Å/1,000 Å/70 Å) electrode (first electrode, anode) was sonicated in distilled water, further sonicated in a solvent such as isopropyl alcohol, acetone, and methanol, and dried. Then, the substrate was placed in a plasma cleaner and washed for 5 minutes by using an oxygen plasma and then mounted on a vacuum deposition apparatus.

Compound 2-TNATA was vacuum deposited on the glass substrate with an ITO electrode to form a hole injection layer having a thickness of 600 Å, and NPB was deposited on the hole injection layer to form a hole transport layer having a thickness of 1,350 Å, thereby forming a hole transport region.

CBP (host) and Compound PD-57 (dopant) were co-deposited on the hole transport region in a weight ratio of 91:1 to form an emission layer having a thickness of 400 Å. BCP was deposited on the emission layer to form a hole blocking layer having a thickness of 50 Å, and Alq3 was deposited on the hole blocking layer to form an electron transport layer having a thickness of 350 Å. LiF was deposited on the electron transport layer to form an electron injection layer having a thickness of 10 Å, and MgAg (in a weight ratio of 90:10) second electrode (cathode) having a thickness of 120 Å was formed on the electron injection layer to manufacture an organic light-emitting device.

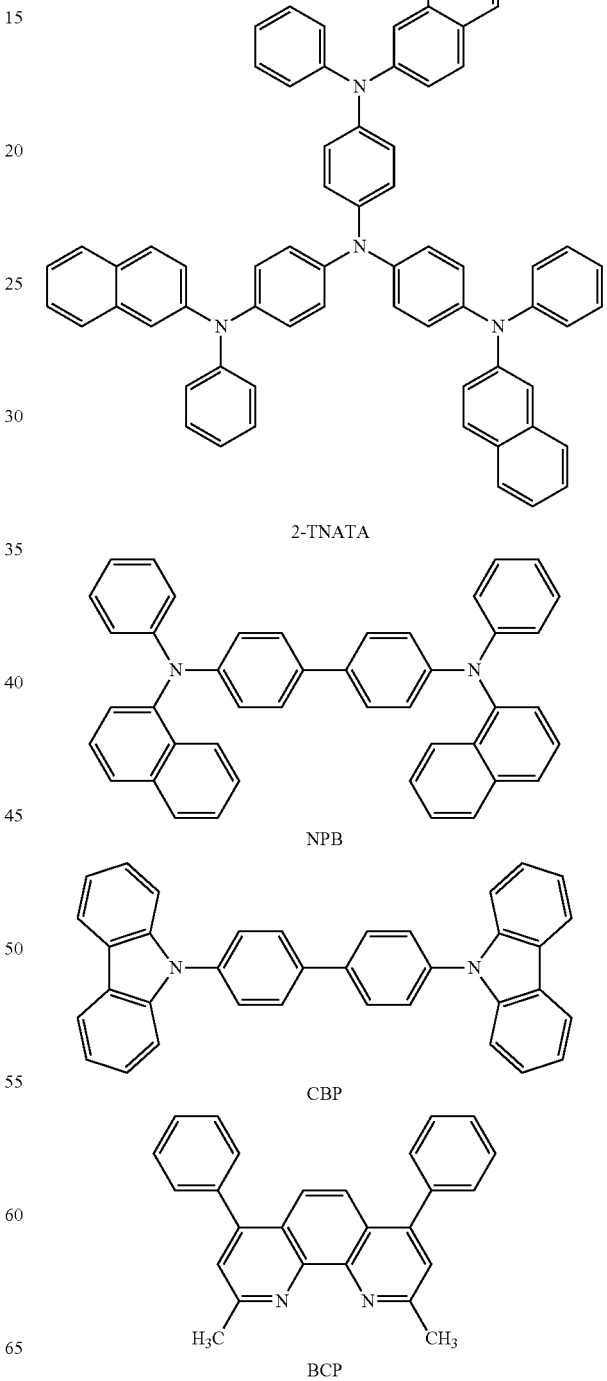

Examples R2 to R4 and Comparative Examples R1

Organic light-emitting devices were manufactured in the same manner as in Example R1, except that, as a dopant, compounds shown in Table 3 were respectively used instead of Compound 10:

TABLE 3

| | dopant |
|---|---|
| Example R1 | Compound PD-57 |
| Example R2 | Compound PD-4 |
| Example R3 | Compound PD-5 |
| Example R4 | Compound PD-58 |
| Example R5 | Compound PD-31 |
| Example R6 | Compound PD-63 |
| Comparative Example R1 | PtOEP |

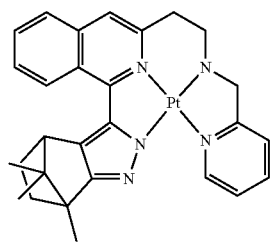

PD-57

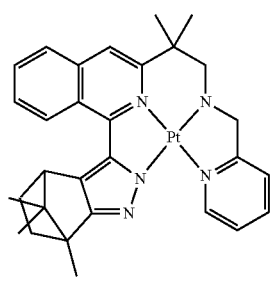

PD-4

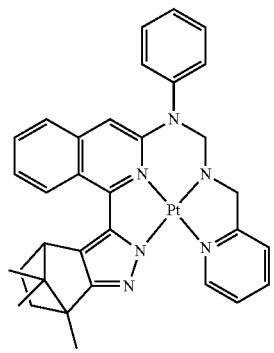

PD-5

TABLE 3-continued

| dopant |
|---|

PD-58

PD-31

PD-63

PtOEP

Evaluation Example 1

Characteristic Evaluation of Organic Light-Emitting Device

Changes in current density and luminance according to a voltage, luminous efficiency, emission color and lifespan were measured with respect to organic light-emitting devices manufactured in Examples G1 to G5, Examples R1 to R6, Comparative Examples G1 to G3 and Comparative Example R1. Detailed method is explained below, and the results of measurement are shown in Table 4:

(1) Measurement on Changes in Current Density According to a Voltage

Current values of the organic light-emitting devices prepared in Examples G1 to G5, Examples R1 to R6, Comparative Examples G1 to G3 and Comparative Example R1 were measured by measuring values of current in a unit device thereof using a current voltmeter (Keithley 2400) while increasing the applied voltage from about 0 (V) to about 10 V. The result was obtained by dividing a current value by an area.

(2) Measurement on Changes in Luminance

Luminance values of the organic light-emitting devices prepared in Examples G1 to G5, Examples R1 to R6, Comparative Examples G1 to G3 and Comparative Example R1 were measured by using a luminance meter (Minolta Cs-1,000 Å) while increasing the applied voltage from about 0 V to about 10 V.

(3) Measurement on Luminous Efficiency

The luminance values measured from (2) and current density values measured from (1), and applied voltages were used in calculating current efficiencies (Candelas per Ampere (cd/A)) in a condition of an identical current density (10 milliAmperes per square centimeter (mA/cm$^2$)).

(4) Measurement on Lifespan

An amount of time was measured until luminance measured in (2) was decreased to 97% of its initial value.

TABLE 4

| | emission layer | | driving voltage (V) | current density (mA/cm$^2$) | luminance (cd/m$^2$) | efficiency (cd/A) | emission color | lifespan (hr) |
|---|---|---|---|---|---|---|---|---|
| | host | dopant | | | | | | |
| Example G1 | CBP | Compound PD-1 | 5.3 | 10 | 6350 | 63.2 | green | 110 |
| Example G2 | CBP | Compound PD-55 | 5.2 | 10 | 6640 | 66.4 | green | 108 |
| Example G3 | CBP | Compound PD-2 | 5.0 | 10 | 6752 | 67.5 | green | 105 |
| Example G4 | CBP | Compound PD-56 | 5.4 | 10 | 6840 | 68.4 | green | 100 |
| Example G5 | CBP | Compound PD-62 | 5.1 | 10 | 6510 | 65.1 | green | 110 |
| Comparative Example G1 | CBP | Ir(ppy)$_3$ | 6.7 | 10 | 4753 | 47.5 | green | 59 |
| Comparative Example G2 | CBP | Compound A | 6.0 | 10 | 5420 | 54.2 | green | 63 |
| Comparative Example G3 | CBP | Compound B | 6.3 | 10 | 5640 | 56.4 | green | 68 |
| Example R1 | CBP | Compound PD-57 | 6.3 | 10 | 5420 | 54.2 | red | 222 |
| Example R2 | CBP | Compound PD-4 | 6.5 | 10 | 5100 | 51.0 | red | 243 |
| Example R3 | CBP | Compound PD-5 | 6.3 | 10 | 5790 | 57.9 | red | 210 |
| Example R4 | CBP | Compound PD-58 | 6.6 | 10 | 5530 | 55.3 | red | 205 |
| Example R5 | CBP | Compound PD-31 | 6.1 | 10 | 3960 | 39.6 | red | 112 |
| Example R6 | CBP | Compound PD-63 | 6.2 | 10 | 4870 | 48.7 | red | 156 |
| Comparative Example R1 | CBP | PtOEP | 7.1 | 10 | 2111 | 21.1 | red | 85 |

According to Table 4, organic light-emitting devices of Examples G1 to G5 have low driving voltage, high luminance, high efficiency, and long lifespan compared to those of Comparative Examples G1 to G3.

According to Table 4, organic light-emitting device of Examples R1 to R6 have low driving voltage, high luminance, high efficiency, and long lifespan compared to those of Comparative Example R1.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:
1. An organometallic compound represented by Formula 1:

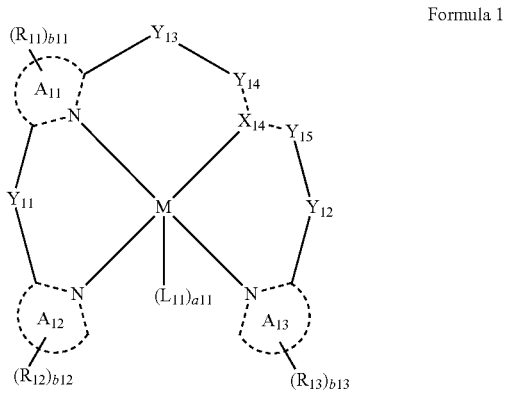

Formula 1 wherein in Formula 1,
M is selected from a Period 1 transition metal, a Period 2 transition metal, and a Period 3 transition metal;
$A_{11}$ to $A_{13}$ are each independently selected from a $C_6$-$C_{20}$ cyclic group and a $C_1$-$C_{20}$ heterocyclic group; wherein $A_{11}$ and $A_{l2}$ are optionally linked to each other through a first linking group;
$X_{11}$ to $X_{13}$ are each independently N;
$X_{14}$ is selected from N and P;
$E_{11}$ to $E_{14}$ are each independently a single bond;
$Y_{11}$ to $Y_{15}$ are each independently selected from a single bond and a divalent linking group; $X_{14}$ and $Y_{14}$ are linked together by a single bond or a double bond, and $X_{14}$ and $Y_{15}$ are linked together by a single bond or a double bond;
$L_{11}$ is selected from a monodentate ligand and a bidentate ligand;
a11 is selected from 0, 1, and 2; and
$R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), and —N($Q_1$)($Q_2$);
wherein $Q_1$ to $Q_3$ are each independently selected from a $C_1$-$C_{60}$ alkyl group and a $C_6$-$C_{60}$ aryl group;
b11 to b13 are each independently selected from 1, 2, 3, 4, 5, 6, 7, 8, 9, and 10; and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein M is selected from Os, Ir, and Pt.
3. The organometallic compound of claim 1, wherein $A_{11}$ to $A_{13}$ are each independently selected from
a pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, a benzoimidazole, a benzoxazole, an isobenzoxazole, an indazole, and a tetrahydroindazole; and
pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, a benzoimidazole, a benzoxazole, an isobenzoxazole, an indazole, and a tetrahydroindazole, each condensed with at least one selected from a $C_4$-$C_{10}$ alicyclic group and a $C_1$-$C_{10}$ heteroalicyclic group.
4. The organometallic compound of claim 1, wherein $A_{11}$ is selected from groups represented by Formulae 2-5 to 2-8:

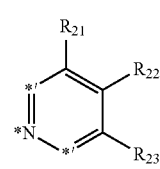

2-5

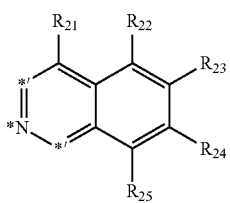

2-6

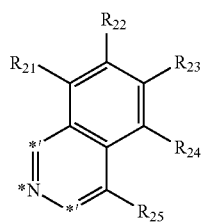

2-7

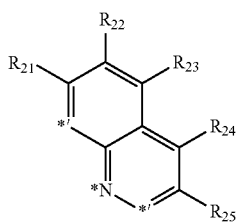

2-8 wherein in Formulae 2-5 to 2-8,
* is a binding site to M in Formula 1;
*' is a binding site to $Y_{11}$ or $Y_{13}$; and
$R_{21}$ to $R_{25}$ each independently are the same as $R_{11}$ in Formula 1.

5. The organometallic compound of claim 1, wherein $A_{12}$ and $A_{13}$ are each independently selected from groups represented by Formulae 3-4 to 3-9:

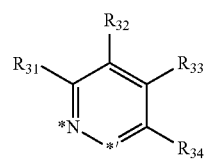

3-4

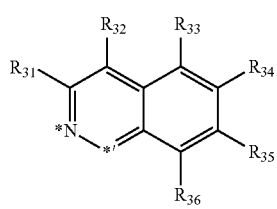

3-5

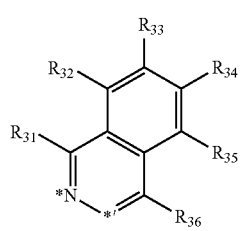

3-6

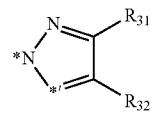

3-7

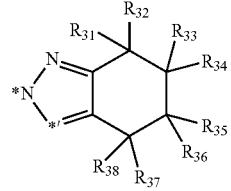

3-8

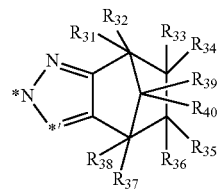

3-9 wherein in Formulae 3-4 to 3-9,
* is a binding site to M in Formula 1;
*' is a binding site to $Y_{11}$ or $Y_{12}$; and
$R_{31}$ to $R_{40}$ each independently are the same as $R_{12}$ and $R_{13}$ in Formula 1.

6. The organometallic compound of claim 1, wherein $X_{14}$ is N.

7. The organometallic compound of claim 1, wherein $Y_{11}$ to $Y_{15}$ are each independently selected from a single bond, a double bond, —O—, —S—, —{B($Q_{11}$)}-, —{N($Q_{12}$)}-, —{C($Q_{11}$)($Q_{12}$)}$n_{11}$-, =$\{C(Q_{11})\}_{n1}$-, —{Si($Q_{11}$)($Q_{12}$)}$_{n11}$-, —C(=O)—, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
wherein $Q_{11}$ and $Q_{12}$ are each independently selected from a hydrogen, a deuterium, a $C_1$-$C_{60}$ alkyl group, a $C_6$-$C_{60}$ aryl group, and a $C_1$-$C_{60}$ heteroaryl group; and n11 is selected from 1, 2, and 3.

8. The organometallic compound of claim 1, wherein $Y_{11}$ to $Y_{15}$ are each independently selected from a single bond, a double bond, —O—, —S—, —N($CH_3$)—, —N(Ph)-, —$CH_2$—, —CH($CH_3$)—, —C($CH_3$)$_2$—, —C($CH_3$)(Ph)-, —C(Ph)$_2$-, =C($CH_3$)—, =C(Ph)-, —C(=O)—, and groups represented by Formulae 4-1 to 4-17:

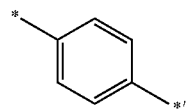

4-1

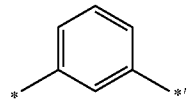

4-2

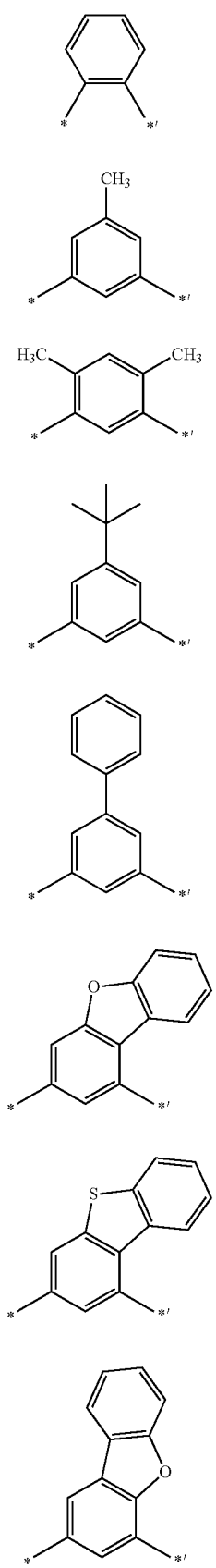
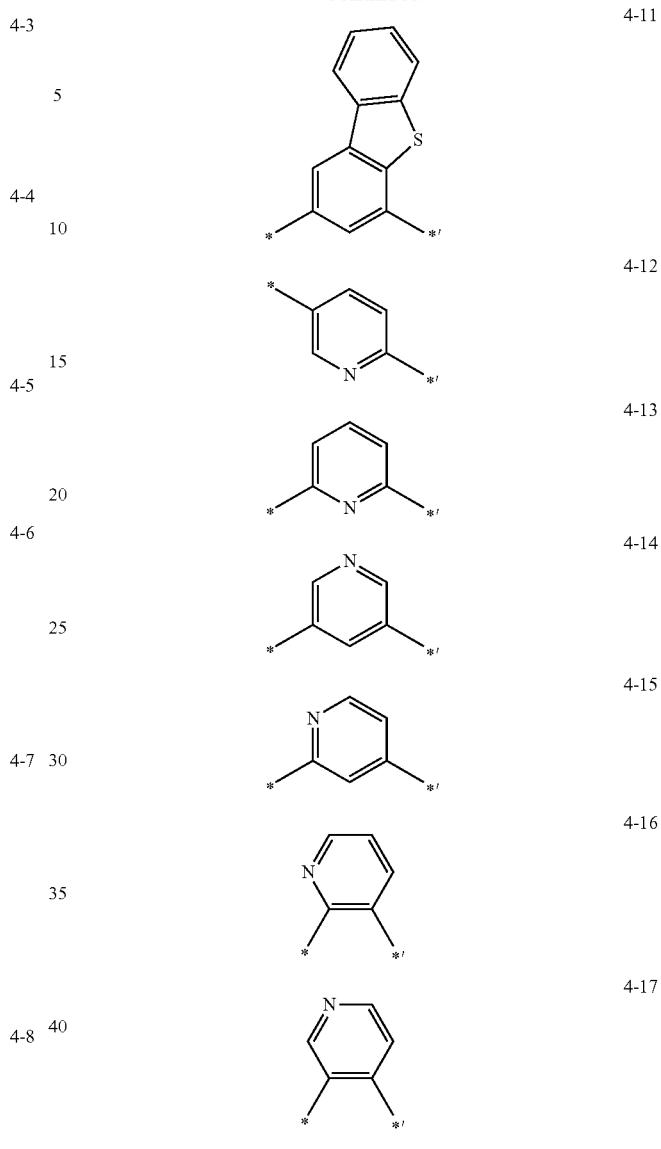

wherein in Formulae 4-1 to 4-17,
each of * and *' is a binding site to a neighboring atom.

9. The organometallic compound of claim 1, wherein $Y_{11}$ to $Y_{13}$ are each independently selected from a single bond, a double bond, —O—, —S—, —N(CH$_3$)—, —N(Ph)-, —CH$_2$—, —CH(CH$_3$)—, —C(CH$_3$)$_2$—, and —C(=O)—.

10. The organometallic compound of claim 1, wherein $Y_{14}$ and $Y_{15}$ are each independently selected from a single bond, a double bond, —CH$_2$—, =C(CH$_3$)—, =C(Ph)-, and —C(=O)—.

11. The organometallic compound of claim 1, wherein $L_{11}$ is selected from

I$^-$, Br$^-$, Cl$^-$, a sulfide, a nitrate, an azide, a hydroxide, a cyanate, an isocyanate, a thiocyanate, water, an acetonitrile, a pyridine, an ammonia, a carbon monoxide, P(Ph)$_3$, P(Ph)$_2$CH$_3$, PPh(CH$_3$)$_2$, and P(CH$_3$)$_3$; and an oxalate, an acetylacetonate, a picolinic acid, a 1,2-bis (diphenylphosphino)ethane, a 1,1-bis(diphenylphosphino)methane, a glycinate, and an ethylenediamine.

12. The organometallic compound of claim 1, wherein $R_{11}$ to $R_{13}$ are each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —CF$_3$, a methoxy group, an ethoxy group, a tert-butoxy group, a phenyl group, —C(=O))(Q$_1$), —Si(Q$_1$)(Q$_2$)(Q$_3$), and —N(Q$_1$)(Q$_2$);

wherein $Q_1$ to $Q_3$ are each independently selected from a methyl group, an ethyl group, an n-propyl group, an iso-propyl group, an n-butyl group, an iso-butyl group, a sec-butyl group, a tert-butyl group, and a phenyl group.

13. The organometallic compound of claim 1, wherein $R_{11}$ to $R_{13}$ are each independently selected from a hydrogen, —F, a cyano group, a methyl group, an iso-propyl group, a tert-butyl group, —CF$_3$, and —Si(CH$_3$)$_3$.

14. The organometallic compound of claim 1, wherein the organometallic compound is selected from groups represented by Formulae 1-1 to 1-3:

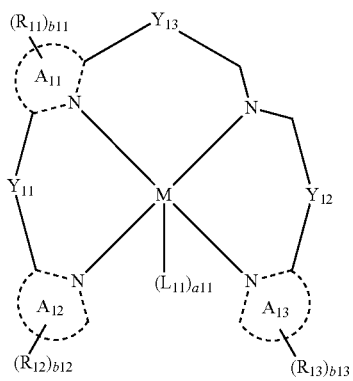

1-1

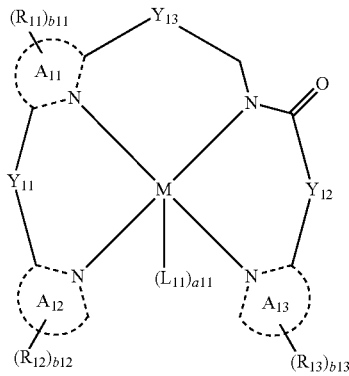

1-2

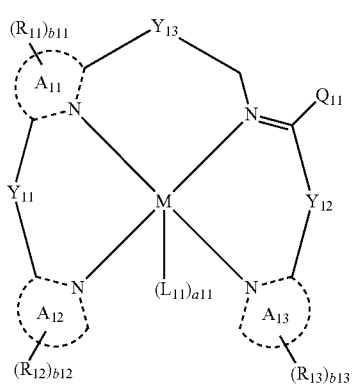

1-3 wherein in Formulae 1-1 to 1-3,

M, $A_{11}$ to $A_{13}$, $Y_{11}$ to $Y_{13}$, $L_{11}$, a11, $R_{11}$ to $R_{13}$, and b11 to b13 are the same as defined in Formula 1; and $Q_{11}$ is selected from a hydrogen, a deuterium, a $C_1$-$C_{60}$ alkyl group, a $C_6$-$C_{60}$ aryl group, and a $C_1$-$C_{60}$ heteroaryl group.

15. The organometallic compound of claim 1, wherein the organometallic compound is represented by Formulae 1-11, 1-13, or 1-15:

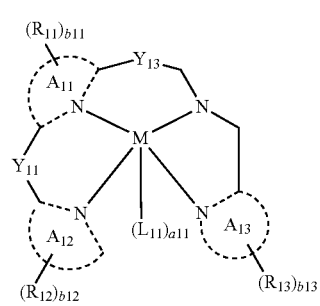

1-11

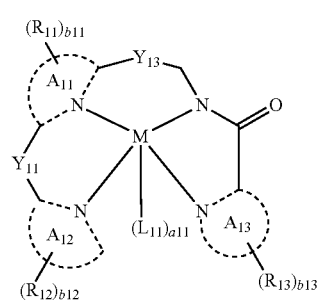

1-13

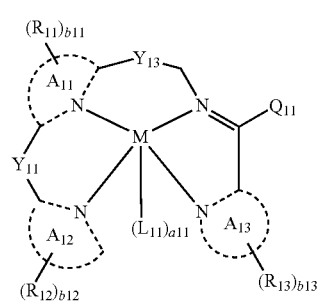

1-15 wherein in Formula 1-11, 1-13, and 1-15,

M, $A_{11}$ to $A_{13}$, $Y_{11}$, $Y_{13}$, $L_{11}$, a11, $R_{11}$ to $R_{13}$, and b11 to b13 are the same as defined in Formula 1; and $Q_{11}$ is selected from a hydrogen, a deuterium, a methyl group, an ethyl group, an n-propyl group, an iso-propyl group, an n-butyl group, an iso-butyl group, a tert-butyl group, and a phenyl group.

16. The organometallic compound of claim 1, wherein the organometallic compound is represented by Formulae 1-21, 1-22, 1-26 to 1-28, 1-32 to 1-34, or 1-38:

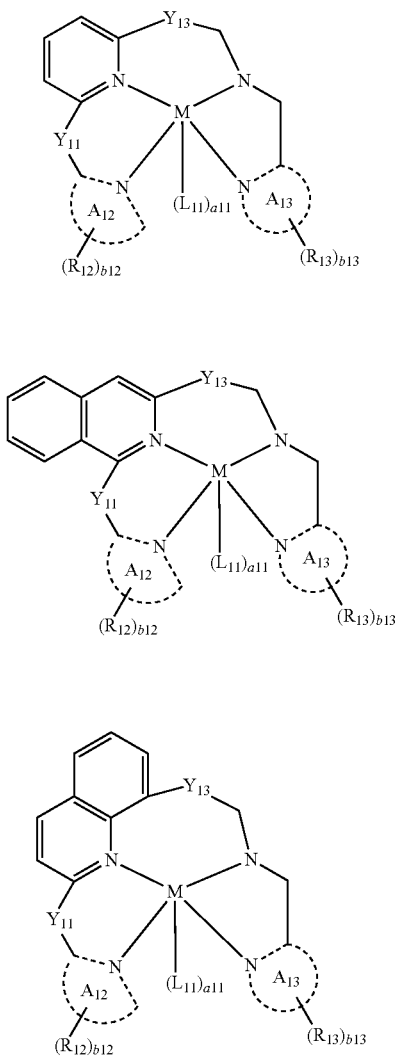
1-21
1-22
1-26
1-27
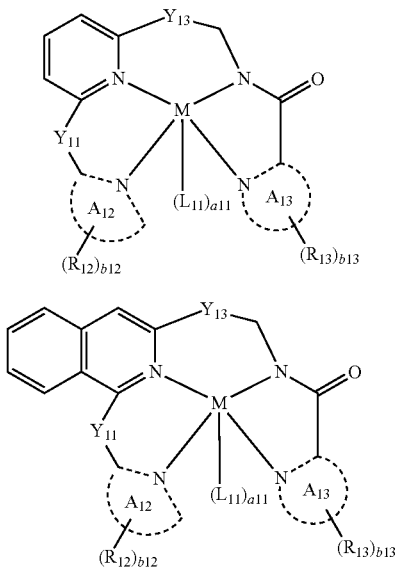
1-28
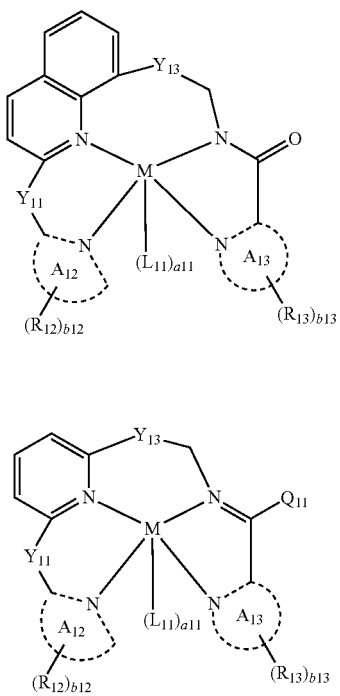
1-32
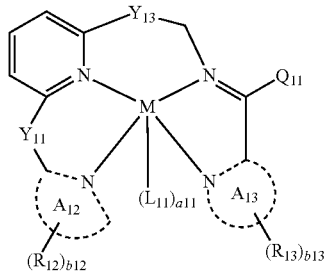
1-33
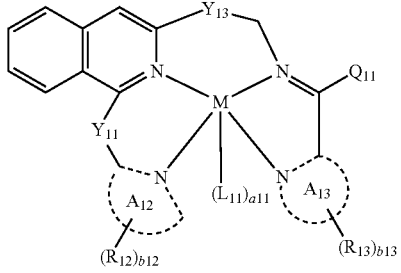
1-34
1-38
wherein in Formulae 1-21, 1-22, 1-26 to 1-28, 1-32 to 1-34, and 1-38,
M, A$_{l2}$, A$_{13}$, Y$_{11}$, Y$_{13}$, L$_{11}$, a11, R$_{12}$, R$_{13}$, b12, and b13 are the same as defined in Formula 1; and
Q$_{11}$ is selected from a hydrogen, a deuterium, a methyl group, an ethyl group, an n-propyl group, an iso-propyl group, an n-butyl group, an iso-butyl group, a tert-butyl group, and a phenyl group.

17. The organometallic compound of claim 1, wherein the organometallic compound is represented by Formulae 1-41, 1-42, 1-45, 1-46, 1-49, or 1-50:

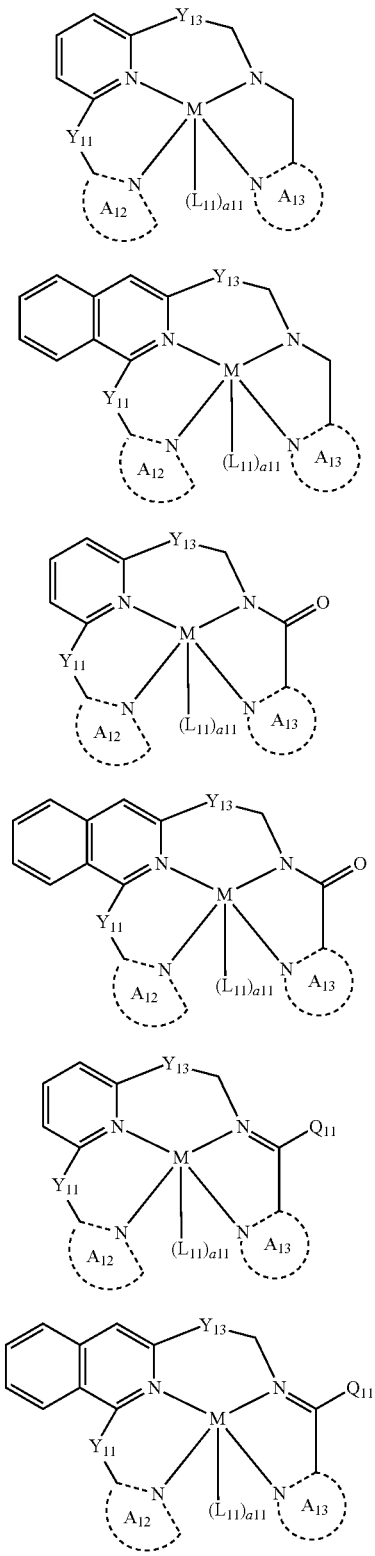

wherein in Formulae 1-41, 1-42, 1-45, 1-46, 1-49 and 1-50,

M, $Y_{11}$, $Y_{13}$, $L_{11}$, and a11 are the same as defined in Formula 1;

$Q_{11}$ is selected from a hydrogen, a deuterium, a methyl group, an ethyl group, an n-propyl group, an iso-propyl group, an n-butyl group, an iso-butyl group, a tert-butyl group, and a phenyl group; and $A_{l2}$ and $A_{13}$ are each independently selected from groups represented by Formulae 3-4 to 3-9;

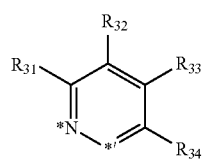

3-4

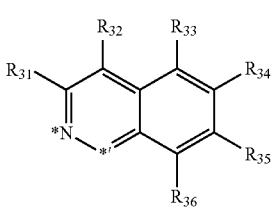

3-5

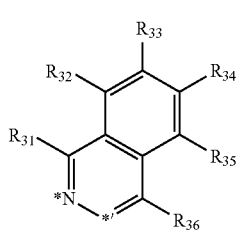

3-6

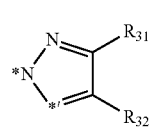

3-7

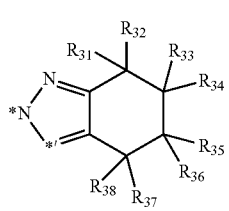

3-8

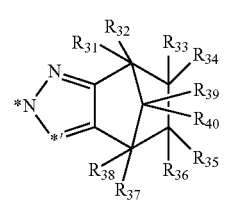

3-9 wherein in Formulae 3-4 to 3-9,

* is a binding site to M;

*' is a binding site to a neighboring atom; and $R_{31}$ to $R_{40}$ are each independently selected from a hydrogen, —F, a cyano group, a methyl group, an iso-propyl group, a tert-butyl group, —$CF_3$, and —$Si(CH_3)_3$.

18. The organometallic compound of claim 1, wherein the organometallic compound is selected from Compounds PD-1 to PD-6, PD-31 to PD-36, PD-46 to PD-48, and PD-51 to PD-64:

PD-1
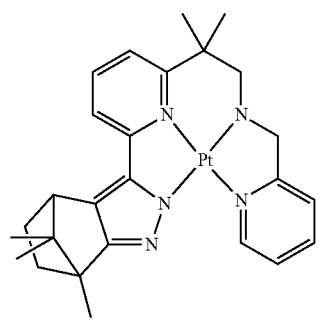
PD-2
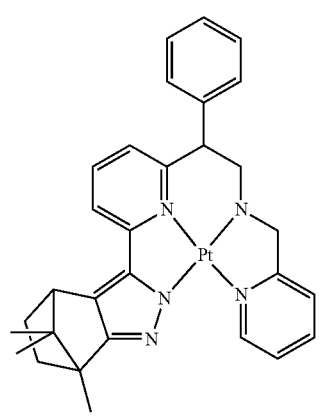
PD-3
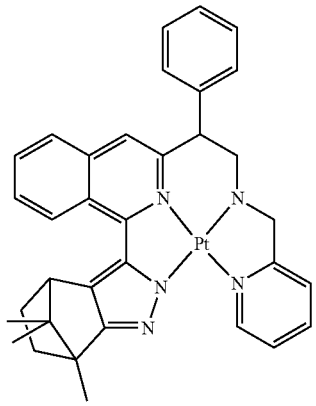
PD-4
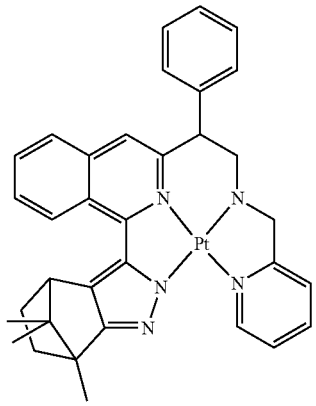
PD-5
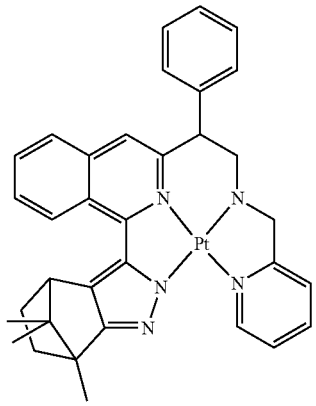
PD-6
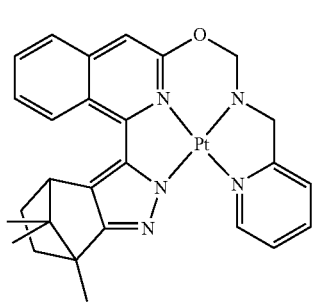
PD-31
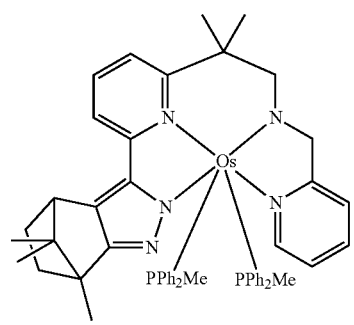
PD-32
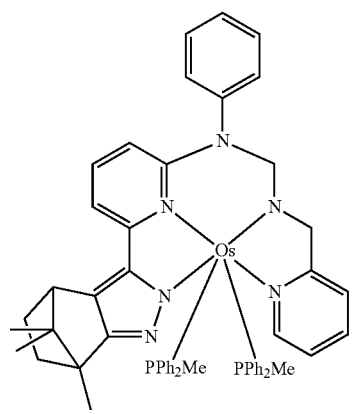

PD-33
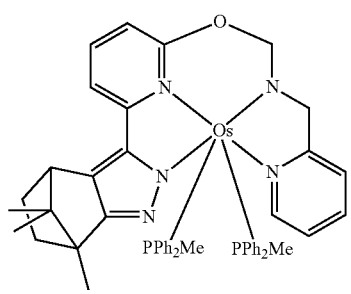
PD-34
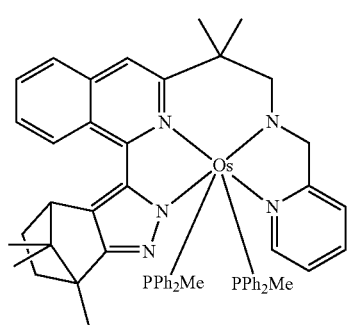
PD-35
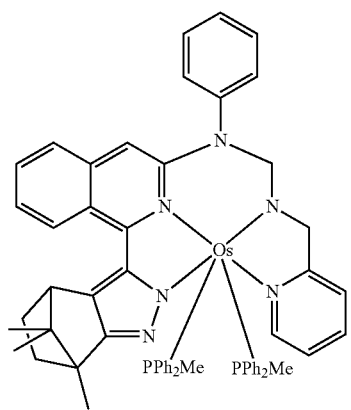
PD-36
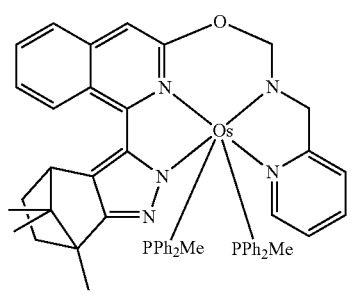
PD-46
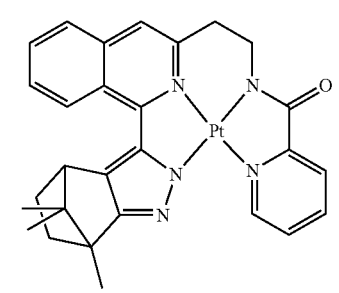
PD-47
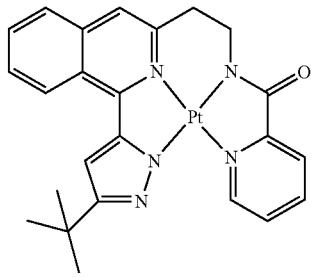
PD-48
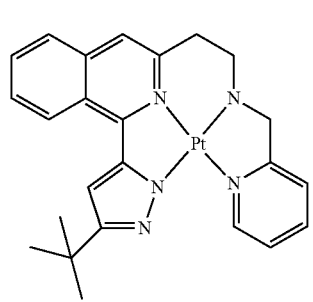
PD-51
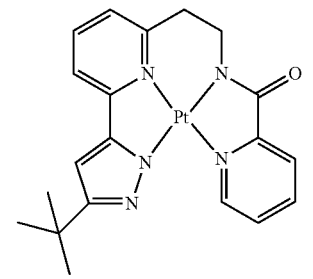
PD-52
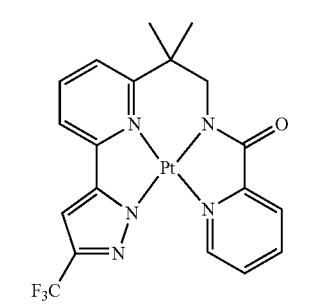
PD-53
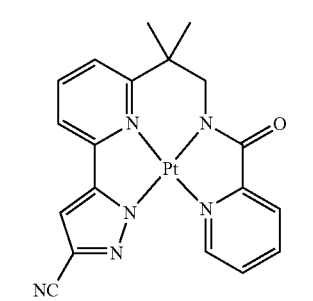

PD-54
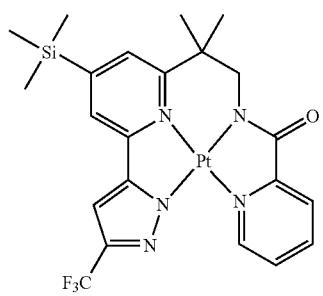
PD-55
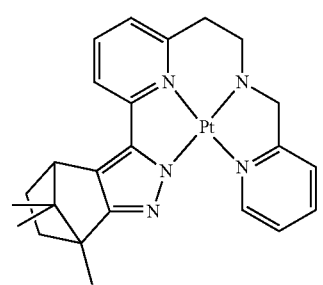
PD-56
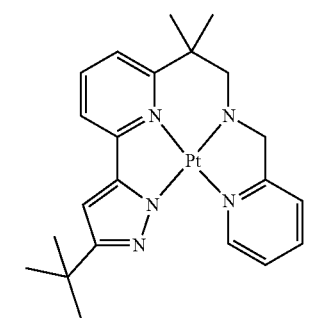
PD-57
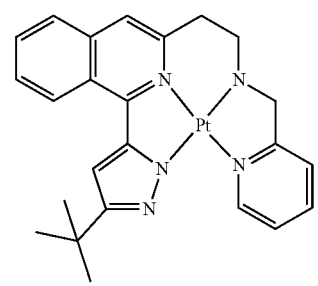
PD-58
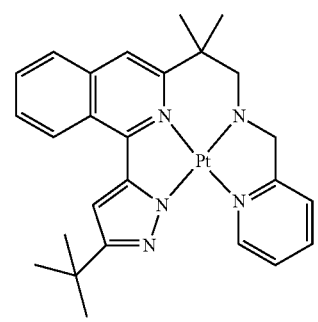
PD-59
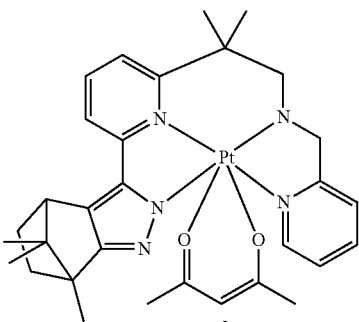
PD-60
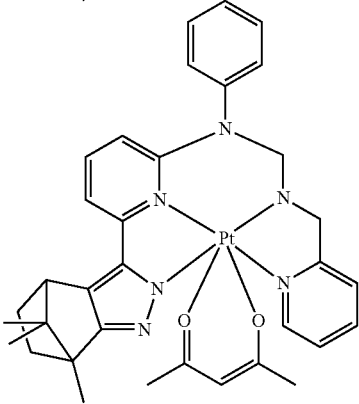
PD-61
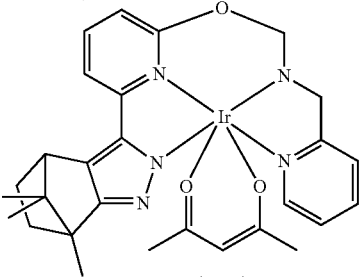
PD-62
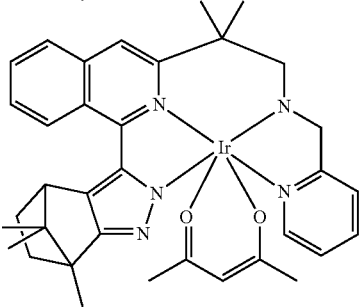
PD-63
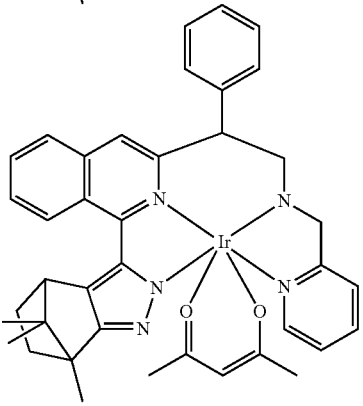

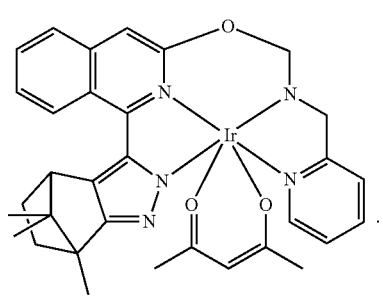

PD-64

19. An organic light-emitting device comprising:
a first electrode;
a second electrode; and
an organic layer disposed between the first electrode and the second electrode,
wherein the organic layer comprises an emission layer, and
wherein the organic layer comprises the organometallic compound of claim 1.

20. The organic light-emitting device of claim 1, wherein the emission layer comprises the organometallic compound of claim 1.

* * * * *